US009045731B2

(12) United States Patent
Li et al.

(10) Patent No.: US 9,045,731 B2
(45) Date of Patent: Jun. 2, 2015

(54) COMPOSITIONS AND METHODS FOR IMPROVING THE FUNCTIONAL EFFICACY OF STEM CELL-DERIVED CARDIOMYOCYTES

(75) Inventors: Ronald Li, Davis, CA (US);
Chung-wah Siu, Davis, CA (US);
Deborah K. Lieu, Davis, CA (US); Jing Liu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 365 days.

(21) Appl. No.: 12/677,790

(22) PCT Filed: Sep. 11, 2008
(Under 37 CFR 1.47)

(86) PCT No.: PCT/US2008/076084
§ 371 (c)(1),
(2), (4) Date: Nov. 29, 2010

(87) PCT Pub. No.: WO2009/036220
PCT Pub. Date: Mar. 19, 2009

(65) Prior Publication Data
US 2012/0014924 A1    Jan. 19, 2012

Related U.S. Application Data

(60) Provisional application No. 60/971,855, filed on Sep. 12, 2007.

(51) Int. Cl.
C12N 5/00       (2006.01)
C12N 5/0735    (2010.01)
C12N 5/077     (2010.01)
A61K 35/12      (2006.01)

(52) U.S. Cl.
CPC ............... *C12N 5/0606* (2013.01); *A61K 35/12* (2013.01); *C12N 5/0657* (2013.01); *C12N 2500/25* (2013.01); *C12N 2500/33* (2013.01); *C12N 2500/44* (2013.01); *C12N 2501/115* (2013.01); *C12N 2503/02* (2013.01); *C12N 2506/02* (2013.01); *C12N 2510/00* (2013.01); *C12N 2502/13* (2013.01)

(58) Field of Classification Search
CPC .................................................... C12N 5/0657
USPC ......................................................... 435/325
See application file for complete search history.

(56) References Cited

U.S. PATENT DOCUMENTS

| 5,733,761 | A  | 3/1998  | Treco et al.     |
|-----------|----|---------|------------------|
| 6,207,422 | B1 | 3/2001  | Brown et al.     |
| 6,214,620 | B1 | 4/2001  | Johns et al.     |
| 6,387,369 | B1 | 5/2002  | Pittenger et al. |
| 6,638,369 | B1 | 10/2003 | Tucker et al.    |
| 6,686,198 | B1 | 2/2004  | Melton et al.    |
| 7,202,080 | B2 | 4/2007  | Ramiya et al.    |
| 2004/0033943 | A1 | 2/2004  | Strijbos et al. |
| 2004/0254134 | A1 | 12/2004 | Marban et al.   |
| 2005/0042254 | A1 | 2/2005  | Freyman et al.  |
| 2005/0058633 | A1 | 3/2005  | Epstein et al.  |
| 2005/0244377 | A1 | 11/2005 | Sigg et al.     |
| 2006/0128647 | A1 | 6/2006  | Sigg et al.     |
| 2007/0025972 | A1 | 2/2007  | Rodriguez et al.|
| 2007/0161107 | A1 | 7/2007  | Mummery et al.  |

FOREIGN PATENT DOCUMENTS

| WO | WO 00/18903    | A2 | 4/2000  |
|----|----------------|----|---------|
| WO | WO 02/19966    | A2 | 3/2002  |
| WO | WO 02/087419   | A2 | 11/2002 |
| WO | WO 2006/017566 | A2 | 2/2006  |
| WO | WO 2006/017567 | A2 | 2/2006  |
| WO | WO 2009/152482 | A2 | 12/2009 |

OTHER PUBLICATIONS

Fu et al (FASEB, 20(1): 1-21, 2006).*
Terentyev et al (PNAS, 2003, 100(20): 11759-11764).*
Beqqali et al (Stem Cells, 24: 1956-1967, May 4, 2006).*
Kiriazis (Annual Review of Physiology vol. 62: 321-351 (Volume publication date Mar. 2000).*
Baharvand, H. et al. (2005) "The effect of extracellular matrix on embryonic stem cell-derived cardiomyocytes," Journal of Molecular and Cellular Cardiology 38:495-503.
Huber, I. et al. (2007) "Identification and selection of cardiomyocytes during human embryonic stem cell differentiation," The FASEB Journal 21:2551-2563.
Parton, R.G. et al. (1997) "Caveolin-3 Associates with Developing T-tubules during Muscle Differentiation," The Journal of Cell Biology 136(1):137-154.
Yang, H-T. et al. (2002) "The ryanodine receptor modulates the spontaneous beating rate of cardiomyocytes during development," PNAS 99(14):9225-9230.

(Continued)

*Primary Examiner* — Peter Paras, Jr.
*Assistant Examiner* — Magdalene Sgagias
(74) *Attorney, Agent, or Firm* — Foley & Lardner LLP; Antoinette F. Konski

(57) ABSTRACT

This invention provides an isolated stem cell that has been modified to provide, enhance or contain the functional characteristics of the sarcoplasmic reticulum (SR). The isolated stem cells are modified in one or more of the following manners: by expressing a calcium channel protein; by expressing a calcium pump protein such as the sarco/endoplasmic reticulum Ca2+-ATPase (SERCA) protein; by inhibiting or downregulating expression of the Na+/Ca+ exchanger (NCX) protein; by expressing a calcium handling protein; by expressing a transverse (t-tubule; and/or by expressing a transverse (t-tubule biogenic protein. After the cell has been modified, it may be expanded to a substantially homogenous population of these cells or alternatively, differentiated to a more mature cell type. Compositions containing these cells and population of cells are also provided by this invention. The cells and compositions can he used to regenerate cardiac tissue, improve cardiac function, restore action potential of cardiac tissue; and treat or prevent cardiac malfunction. These methods can be achieved by administering an effective amount of a cell or population of cells or tissue of this invention to a host in need thereof. The cells and population of cells can be used diagnostically to screen drug or other therapeutic candidates.

3 Claims, 13 Drawing Sheets

(56) References Cited

OTHER PUBLICATIONS

Koban, M.U. et al. (1998) "Expressional analysis of the cardiac Na—Ca exchanger in rat development and senescence," Cardiovascular Research 37:405-423.

Xue, T. et al. (2005) "Functional Integration of Electrically Active Cardiac Derivatives From Genetically Engineered Human Embryonic Stem Cells With Quiescent Recipient Ventricular Cardiomyocytes," Circulation 111:11-20.

Moore, J.C. et al. (2005) "Human embryonic stem cells: Genetic manipulation on the way to cardiac cell therapies," Reproductive Technology 20:377-391.

Miller, S.L.W. et al. (2005) "Effects of calsequestrin over-expression on excitation-contraction coupling in isolated rabbit cardiomyocytes," Cardiovascular Research 67:667-677.

Liu, J. et al. (2007) "Functional Sarcoplasmic Reticulum for Calcium Handling of Human Embryonic Stem Cell-Derived Cardiomyocytes: Insights for Driven Maturation," Stem Cells 25:3038-3044.

Sartiani, L. et al. (2007) "Developmental Changes in Cardiomyocytes Differentiated from Human Embryonic Stem Cells: A Molecular and Electrophysiological Approach," Stem Cells 25:1136-1144.

He, J-Q. et al. (2003) "Human Embryonic Stem Cells Develop Into Multiple Types of Cardiac Myocytes," Circ. Res. 93:32-39.

Mummery, C. et al. (2002) "Differentiation of Human Embryonic Stem Cells to Cardiomyocytes," Circulation 107:2733-2740.

Fu, J-D. et al. (2006) "Developmental regulation of intracellular calcium transients during cardiomyocyte differentiation of mouse embryonic stem cells," Acta Pharmacologica Sinica 27(7):901-910.

Satin, J. et al. (2004) "Mechanism of spontaneous excitability in human embryonic stem cell derived cardiomyocytes," J Physiol 559(2):479-496.

Sauer, H. et al. (2001) "Characteristics of calcium sparks in cardiomyocytes derived from embryonic stem cells," Am J Physiol Heart Cir Physiol 281:H411-H421.

Kolossov, E. et al. (1998) "Functional Characteristics of ES Cell-derived Cardiac Precursor Cells Identified by Tissue-specific Expression of the Green Fluorescent Protein," The Journal of Cell Biology 143(7):2045-2056.

Gorza, L. et al. (1993) "Inositol 1,4,5-Trisphosphate Receptor in Heart: Evidence for its Concentration in Purkinje Myocytes of the Conduction System," The Journal of Cell Biology 121(2):345-353.

Kapur, N. et al. (2007) "Inositol 1,4,5-trisphosphate-mediated spontaneous activity in mouse embryonic stem cell-derived cardiomyocytes," J Physiol 581(3):1113-1127.

International Search Report (ISA/US) for International Application No. PCT/US08/76084, mailed Feb. 19, 2009.

U.S. Appl. No. 11/864,755, filed Sep. 28, 2007, Li et al.

Abraham, M.R. et al. (2005) "Antiarrhythmic Engineering of Skeletal Myoblasts for Cardiac Transplantation," Circ. Res. 97(2):159-167.

Alseikhan, B.A. et al. (2002) "Engineered calmodulins reveal the unexpected eminence of $Ca^{2+}$ channel inactivation in controlling heart excitation," Proc. Natl. Acad. Sci. USA 99:17185-17190.

Accili, E.A. et al. (2002) "From Funny Current to HCN Channels: 20 Years of Excitation," News Physiol. Sci. 17:32-37.

Azene, E.M. et al. (2003) "Molecular basis of the effect of potassium on heterologously expressed pacemaker (HCN) channels," J. Physiol. 547:349-356.

Azene, E.M. et al. (2005) "Pore-to-gate coupling of HCN channels revealed by a pore variant that contributes to gating but not permeation," Biochem. Biophys. Res. Commun. 327:1131-1142.

Azene, E.M. et al. (2005) "Non-equilibrium behavior of HCN channels: Insights into the role of HCN channels in native and engineered pacemakers," Cardiovascular Research 67:263-273.

Baruscotti, M. et al. (2004) "Pacemaker Channels," Ann. N.Y. Acad. Sci. 1015:111-121.

Boheler, K.R. et al. (2002) "Differentiation of Pluripotent Embryonic Stem Cells Into Cardiomyocytes," Circulation Research 91:189-201.

Boyett, M.R. et al. (1998) "Regional differences in effects of 4-aminopyridine within the sinoatrial node," Am. J. Physiol. 275 (Heart Circ. Physiol. 44):H1158-H1168.

Boyett, M.R. et al. (1999) "Downward gradient in action potential duration along conduction path in and around the sinoatrial node," Am. J. Physiol. 276:H686-H698.

Boyett, M.R. et al. (2000) "The sinoatrial node, a heterogeneous pacemaker structure," Cardiovascular Research 47:658-687.

Brown, A.M. (1990) "Regulation of heartbeat by G protein-coupled ion channels," American Journal of Physiology, Heart and Circulatory Physiology 259(6):H1621-H1628.

Bucchi, A.B. et al. (2006) "Wild-type and mutant HCN channels in a tandem biological-electronic cardiac pacemaker," Circulation 114:992-999.

Cohen, I.S. et al. (2005) "The why, what, how and when of biological pacemakers," Nat. Clin. Pract. Cardiovasc. Med. 2(8):374-375.

Difrancesco, D. (1993) "Pacemaker mechanisms in cardiac tissue," Annu. Rev. Physiol. 55:455-472.

Dolnikov, K. et al. (2006) "Functional properties of human embryonic stem cell-derived cardiomyocytes: intracellular $Ca^{2+}$ handling and the role of sarcoplasmic reticulum in the contraction," Stem Cells 24:236-245.

Donahue, J.K. et al. (2000) "Focal modification of electrical conduction in the heart by viral gene transfer," Nature Medicine 6(12):1395-1398.

Donello, J.E. et al. (1998) "Woodchuck Hepatitis Virus Contains a Tripartite Posttranscriptional Regulatory Element," Journal of Virology 72(6):5085-5092.

Edelberg, J.M. et al. (1998) "Enhancement of Murine Cardiac Chronotropy by the Molecular Transfer of the Human β2 Andrenergic Receptor cDNA," J. Clin. Invest. 101(2):337-343.

El-Kholy, W. et al. (2007) "Hyperpolarizaton-Activated Cyclic Nucleotide-Gated Channels in Pancreatic β-Cells," Molecular Endocrinology 21(3):753-764.

Ennis, I.L. et al. (2002) "Dual gene therapy with SERCA1 and Kir2.1 abbreviates excitation without suppressing contractility," J. Clin. Invest. 109:393-400.

Er, F. et al. (2003) "Dominant-negative suppression of HCN channels markedly reduces the native pacemaker current $I_f$ and undermines spontaneous beating of neonatal cardiomyocytes," Circulation 107:485-489.

Feld, Y. et al. (2002) Electrophysiological Modulation of Cardiomyocytic Tissue by Transfected Fibroblasts Expressing Potassium Channels: A Novel Strategy to Manipulate Excitability, Circulation 105:522-529.

Fink, M. et al. (1996) "Dominant negative chimeras provide evidence for homo and heteromultimeric assembly of inward rectifier $K^+$ channel proteins via their N-terminal end," FEBS Letters 378:64-68.

Friedman, B. et al. (1999) "A Comparison of the Pharmacological Properties of Carbohydrate Remodeled Recombinant and Placental-Derived β-Glucocerebrosidase: Implications for Clinical Efficacy in Treatment of Gaucher Disease," Blood 93(9):2807-2816.

Gepstein, L. et al. (2004) "Somatic gene and cell therapy strategies for the treatment of cardiac arrhythmias," Am. J. Physiol. Heart and Circulatory Physiology 286(3):H815-H822.

Graziani, A.T. et al. (2006) "Mechanisms underlying overdrive suppression and overdrive excitation in guinea pig sino-atrial node," Journal of Biomedical Science 13:703-720.

Hamill, O.P. et al. (1981) "Improved patch-clamp techniques for high-resolution current recording from cells and cell-free membrane patches," Pflügers Arch. 391:85-100.

Harth, G. et al. (1999) "Export of Recombinant *Mycobacterium tuberculosis* Superoxide Dismutase Is Dependent upon Both Information in the Protein and Mycobacterial Export Machinery: A Model for Studying Export of Leaderless Proteins by Pathogenic Mycobacteria," The Journal of Biological Chemistry 274(7):4281-4292.

Henrikson, C.A. et al. (2003) "Identification of a surface charged residue in the S3-S4 linker of the pacemaker (HCN) channel that influences activation gating," The Journal of Biological Chemistry 278(16):13647-13654.

(56) References Cited

OTHER PUBLICATIONS

Hoppe, U.C. et al. (2000) "Adenovirus-mediated inducible gene expression in vivo by a hybrid ecdysone receptor," Molecular Therapy 1(2):159-164.
Ibarra, J. et al. (1991) "Dynamics of the inward rectifier $K^+$ current during the action potential of guinea pig ventricular myocytes," Biophys. J. 60:1534-1539.
Kaplitt, M.G. et al. (1994) "Long-term gene expression and phenotypic correction using adeno-associated virus vectors in the mammalian brain," Nature Genetics 8:148-154.
Kehat, I. et al. (2001) "Human embryonic stem cells can differentiate into myocytes with structural and functional properties of cardiomyocytes," J. Clin. Invest. 108:407-414.
Klein, R.L. et al. (1998) "Neuron-Specific Transduction in the Rat Septohippocampal or Nigrostriatal Pathway by Recombinant Adeno-associated Virus Vectors," Experimental Neurology 150:183-194.
Kodama, I. et al. (1985) "Regional differences in the electrical activity of the rabbit sinus node," Pflügers Arch. 404:214-226.
Kodama, I. et al. (1997) "Regional differences in the role of the $Ca^{2+}$ and $Na^{30}$ currents in pacemaker activity in the sinoatrial node," Am. J. Physiol. 272 (Heart Circ. Physiol. 41):H2793-H2806.
Kumar, D. et al. (2005) "Embryonic stem cells: differentiation into cardiomyocytes and potential for heart repair and regeneration," Coronary Artery Disease 16(2):111-116.
Kurata, Y. et al. (2002) "Dynamical description of sinoatrial node pacemaking: improved mathematical model for primary pacemaker cell," Am. J. Physiol. Heart Circ. Physiol. 283:H2074-H2101.
Lesso, H. et al. (2003) "Helical secondary structure of the external S3-S4 linker of pacemaker (HCN) channels revealed by site-dependent perturbations of activation phenotype," The Journal of Biological Chemistry 278(25):22290-22297.
Li, R.K. et al. (1997) "Natural history of fetal rat cardiomyocytes transplanted into adult rat myocardial scar tissue," Circulation 96(9):II-179-186; discussion 186-187.
Li, R.A. et al. (2005) "Human embryonic stem cell-derived cardiomyocytes: therapeutic potentials and limitations," Journal of Stem Cells 1(2):109-124.
Liu, G.X. et al. (2001) "Comparison of cloned Kir2 channels with native inward rectifier $K^+$ channels from guinea-pig cardiomyocytes," Journal of Physiology 532.1:115-126.
Lopatin, A.N. et al. (2000) "Modulation of potassium channels in the hearts of transgenic and mutant mice with altered polyamine biosynthesis," J. Mol. Cell Cardiol. 32:2007-2024.
Lopatin, A.N. (2002) "Inward rectification and Cardiac Excitability," Biologicheskie Membrany 19(1):57-65.
Lubas, W.A. et al. (2000) "Functional Expression of O-linked GlcNAc Transferase," The Journal of Biological Chemistry 275(15):10983-10988.
Mandel, R.J. et al. (1998) " Characterization of Intrastriatal Recombinant Adeno-Associated Virus-Mediated Gene Transfer of Human Tyrosine Hydroxylase and Human GTP-Cyclohydrolase I in a Rat Model of Parkinson's Disease," The Journal of Neuroscience 18(11):4271-4284.
Miake, J. et al. (2002) "Biological pacemaker created by gene transfer," Nature 419:132-133.
Miake, J. et al. (2003) "Functional role of inward rectifier current in heart probed by Kir2.1 overexpression and dominant-negative suppression," J. Clin. Invest. 111(10):1529-1536.
Mitra, R. et al. (1986) "Two types of calcium channels in guinea pig ventricular myocytes," Proc. Natl. Acad. Sci. USA 83:5340-5344.
Miyazaki, J. et al. (1989) "Expression vector system based on the chicken β-actin promoter directs efficient production of interleukin-5," Gene 79(2):269-277.
Nakamura, T.Y. et al. (1998) "Inhibition of rat ventricular $I_{K1}$ with antisense oligonucleotides targeted to Kir2.1 mRNA," Am. J. Physiol. 274 (Heart Circ. Physiol. 43):H892-H900.
National Center for Biotechnology Information [online], GenBank Entrez Protein Accession No. AAA36771 [retrieved on Sep. 3, 2008] Retrieved from the internet:: http://www.ncbi.nlm.nih.gov/entrez/viewer.fcgi?db=protein&id=339944.
National Center for Biotechnology Information [online], GenBank Entrez Protein Accession No. AAA59855 [retrieved on Sep. 3, 2008] Retrieved from the internet:: http://www.ncbi.nlm.nih.gov/entrez/viewer.fcgi?db=protein&id=188594.
National Center for Biotechnology Information [online], GenBank Entrez Protein Accession No. AAA59891 [retrieved on Sep. 3, 2008] Retrieved from the internet:: http://www.ncbi.nlm.nih.gov/entrez/viewer.fcgi?db=protein&id=189015.
National Center for Biotechnology Information [online], GenBank Entrez Protein Accession No. AAA59895 [retrieved on Sep. 3, 2008] Retrieved from the internet:: http://www.ncbi.nlm.nih.gov/entrez/viewer.fcgi?db=protein&id=189027.
National Center for Biotechnology Information [online], GenBank Entrez Protein Accession No. AAB59509 [retrieved on Sep. 3, 2008] Retrieved from the internet:: http://www.ncbi.nlm.nih.gov/entrez/viewer.fcgi?db=protein&id=339731.
National Center for Biotechnology Information [online], GenBank Entrez Protein Accession No. AAB91993 [retrieved on Sep. 3, 2008] Retrieved from the internet:: http://www.ncbi.nlm.nih.gov/entrez/viewer.fcgi?db=protein&id=2460247.
National Center for Biotechnology Information [online], GenBank Entrez Protein Accession No. AAD29948 [retrieved on Sep. 3, 2008] Retrieved from the internet: http://www.ncbi.nlm.nih.gov/entrez/viewer.fcgi?db=protein&id=4808809.
National Center for Biotechnology Information [online], GenBank Entrez Protein Accession No. AAF01045 [retrieved on Sep. 3, 2008] Retrieved from the internet: http://www.ncbi.nlm.nih.gov/entrez/viewer.fcgi?db=protein&id=6007797.
National Center for Biotechnology Information [online], GenBank Entrez Protein Accession No. AAF73241 [retrieved on Sep. 3, 2008] Retrieved from the internet: http://www.ncbi.nlm.nih.gov/entrez/viewer.fcgi?db=protein&id=8132297.
National Center for Biotechnology Information [online], GenBank Entrez Protein Accession No. AAF73242 [retrieved on Sep. 3, 2008] Retrieved from the internet: http://www.ncbi.nlm.nih.gov/entrez/viewer.fcgi?db=protein&id=8132301.
National Center for Biotechnology Information [online], GenBank Entrez Protein Accession No. AAF97619 [retrieved on Sep. 3, 2008] Retrieved from the internet: http://www.ncbi.nlm.nih.gov/entrez/viewer.fcgi?db=protein&id=9719054.
National Center for Biotechnology Information [online], GenBank Entrez Protein Accession No. AAH31006 [retrieved on Sep. 3, 2008] Retrieved from the internet: http://www.ncbi.nlm.nih.gov/entrez/viewer.fcgi?db=protein&id=21411329.
National Center for Biotechnology Information [online], GenBank Entrez Protein Accession No. AAH89439 [retrieved on Sep. 3, 2008] Retrieved from the internet: http://www.ncbi.nlm.nih.gov/entrez/viewer.fcgi?db=protein&id=58477274.
National Center for Biotechnology Information [online], GenBank Entrez Protein Accession No. AAI07534 [retrieved on Sep. 3, 2008] Retrieved from the internet: http://www.ncbi.nlm.nih.gov/entrez/viewer.fcgi?db=protein&id=77567675.
National Center for Biotechnology Information [online], GenBank Entrez Protein Accession No. AAL89708 [retrieved on Sep. 3, 2008] Retrieved from the internet: http://www.ncbi.nlm.nih.gov/entrez/viewer.fcgi?db=protein&id=19526414.
National Center for Biotechnology Information [online], GenBank Entrez Protein Accession No. AAO49469 [retrieved on Sep. 3, 2008] Retrieved from the internet: http://www.ncbi.nlm.nih.gov/entrez/viewer.fcgi?db=protein&id=28629106.
National Center for Biotechnology Information [online], GenBank Entrez Protein Accession No. AAO49470 [retrieved on Sep. 3, 2008] Retrieved from the internet: http://www.ncbi.nlm.nih.gov/entrez/viewer.fcgi?db=protein&id=28629108.
National Center for Biotechnology Information [online], GenBank Entrez Protein Accession No. AAY53910 [retrieved on Sep. 3, 2008] Retrieved from the internet: http://www.ncbi.nlm.nih.gov/entrez/viewer.fcgi?db=protein&id=66735456.
National Center for Biotechnology Information [online], GenBank Entrez CoreNucleotide Accession No. AB074970 [retrieved on Sep. 3, 2008] Retrieved from the internet: http://www.ncbi.nlm.nih.gov/entrez/viewer.fcgi?db=nuccore&id=21693121.

(56) References Cited

OTHER PUBLICATIONS

National Center for Biotechnology Information [online], GenBank Entrez CoreNucleotide Accession No. AB182123 [retrieved on Sep. 3, 2008] Retrieved from the internet: http://www.ncbi.nlm.nih.gov/entrez/viewer.fcgi?db=nuccore&id=48927625.
National Center for Biotechnology Information [online], GenBank Entrez Protein Accession No. ABC84220 [retrieved on Sep. 3, 2008] Retrieved from the internet: http://www.ncbi.nlm.nih.gov/entrez/viewer.fcgi?db=protein&id=85812161.
National Center for Biotechnology Information [online], GenBank Entrez Protein Accession No. ABR18779 [retrieved on Sep. 3, 2008] Retrieved from the internet: http://www.ncbi.nlm.nih.gov/entrez/viewer.fcgi?db=protein&id=148913210.
National Center for Biotechnology Information [online], GenBank Entrez Protein Accession No. ABV24476 [retrieved on Sep. 3, 2008] Retrieved from the internet: http://www.ncbi.nlm.nih.gov/entrez/viewer.fcgi?db=protein&id=157142988.
National Center for Biotechnology Information [online], GenBank Entrez CoreNucleotide Accession No. AF153819 [retrieved on Sep. 3, 2008] Retrieved from the internet: http://www.ncbi.nlm.nih.gov/entrez/viewer.fcgi?db=nuccore&id=8132300.
National Center for Biotechnology Information [online], GenBank Entrez CoreNucleotide Accession No. AF181988 [retrieved on Sep. 3, 2008] Retrieved from the internet: http://www.ncbi.nlm.nih.gov/entrez/viewer.fcgi?db=nuccore&id=9719053.
National Center for Biotechnology Information [online], GenBank Entrez CoreNucleotide Accession No. AF187964 [retrieved on Sep. 3, 2008] Retrieved from the internet: http://www.ncbi.nlm.nih.gov/entrez/viewer.fcgi?db=nuccore&id=6007796.
National Center for Biotechnology Information [online], GenBank Entrez CoreNucleotide Accession No. AF482710 [retrieved on Sep. 3, 2008] Retrieved from the internet: http://www.ncbi.nlm.nih.gov/entrez/viewer.fcgi?db=nuccore&id=19526413.
National Center for Biotechnology Information [online], GenBank Entrez CoreNucleotide Accession No. AF488549 [retrieved on Sep. 3, 2008] Retrieved from the internet: http://www.ncbi.nlm.nih.gov/entrez/viewer.fcgi?db=nuccore&id=28629105.
National Center for Biotechnology Information [online], GenBank Entrez CoreNucleotide Accession No. AF488550 [retrieved on Sep. 3, 2008] Retrieved from the internet: http://www.ncbi.nlm.nih.gov/entrez/viewer.fcgi?db=nuccore&id=28629107.
National Center for Biotechnology Information [online], GenBank Entrez CoreNucleotide Accession No. AJ010969 [retrieved on Sep. 3, 2008] Retrieved from the internet: http://www.ncbi.nlm.nih.gov/entrez/viewer.fcgi?db=nuccore&id=6006516.
National Center for Biotechnology Information [online], GenBank Entrez CoreNucleotide Accession No. AJ310887 [retrieved on Sep. 3, 2008] Retrieved from the internet: http://www.ncbi.nlm.nih.gov/entrez/viewer.fcgi?db=nuccore&id=18073678.
National Center for Biotechnology Information [online], GenBank Entrez Protein Accession No. BAC02718 [retrieved on Sep. 3, 2008] Retrieved from the internet: http://www.ncbi.nlm.nih.gov/entrez/viewer.fcgi?db=protein&id=21693122.
National Center for Biotechnology Information [online], GenBank Entrez Protein Accession No. BAD23901 [retrieved on Sep. 3, 2008] Retrieved from the internet: http://www.ncbi.nlm.nih.gov/entrez/viewer.fcgi?db=protein&id=48927626.
National Center for Biotechnology Information [online], GenBank Entrez CoreNucleotide Accession No. BC089439 [retrieved on Sep. 3, 2008] Retrieved from the internet: http://www.ncbi.nlm.nih.gov/entrez/viewer.fcgi?db=nuccore&id=58477273.
National Center for Biotechnology Information [online], GenBank Entrez Protein Accession No. CAA29119 [retrieved on Sep. 3, 2008] Retrieved from the internet: http://www.ncbi.nlm.nih.gov/entrez/viewer.fcgi?db=protein&id=34644.
National Center for Biotechnology Information [online], GenBank Entrez Protein Accession No. CAA37068 [retrieved on Sep. 3, 2008] Retrieved from the internet: http://www.ncbi.nlm.nih.gov/entrez/viewer.fcgi?db=protein&id=29727.
National Center for Biotechnology Information [online], GenBank Entrez Protein Accession No. CAA56622 [retrieved on Sep. 3, 2008] Retrieved from the internet: http://www.ncbi.nlm.nih.gov/entrez/viewer.fcgi?db=protein&id=550389.
National Center for Biotechnology Information [online], GenBank Entrez Protein Accession No. CAA73478 [retrieved on Sep. 3, 2008] Retrieved from the internet: http://www.ncbi.nlm.nih.gov/entrez/viewer.fcgi?db=protein&id=2463215.
National Center for Biotechnology Information [online], GenBank Entrez Protein Accession No. CAB56841 [retrieved on Sep. 3, 2008] Retrieved from the internet: http://www.ncbi.nlm.nih.gov/entrez/viewer.fcgi?db=protein&id=6006517.
National Center for Biotechnology Information [online], GenBank Entrez Protein Accession No. CAC70712 [retrieved on Sep. 3, 2008] Retrieved from the internet: http://www.ncbi.nlm.nih.gov/entrez/viewer.fcgi?db=protein&id=20338988.
National Center for Biotechnology Information [online], GenBank Entrez Protein Accession No. CAC70714 [retrieved on Sep. 3, 2008] Retrieved from the internet: http://www.ncbi.nlm.nih.gov/entrez/viewer.fcgi?db=protein&id=20338989.
National Center for Biotechnology Information [online], GenBank Entrez Protein Accession No. CAC84530 [retrieved on Sep. 3, 2008] Retrieved from the internet: http://www.ncbi.nlm.nih.gov/entrez/viewer.fcgi?db=protein&id=18073679.
National Center for Biotechnology Information [online], GenBank Entrez CoreNucleotide Accession No. CH471051 [retrieved on Sep. 3, 2008] Retrieved from the internet: http://www.ncbi.nlm.nih.gov/entrez/viewer.fcgi?db=nuccore&id=74230054.
National Center for Biotechnology Information [online], GenBank Entrez CoreNucleotide Accession No. CH474029 [retrieved on Sep. 3, 2008] Retrieved from the internet: http://www.ncbi.nlm.nih.gov/entrez/viewer.fcgi?db=nuccore&id=71679471.
National Center for Biotechnology Information [online], GenBank Entrez CoreNucleotide Accession No. DQ023214 [retrieved on Sep. 3, 2008] Retrieved from the internet: http://www.ncbi.nlm.nih.gov/entrez/viewer.fcgi?db=nuccore&id=66735455.
National Center for Biotechnology Information [online], GenBank Entrez Protein Accession No. EAW48537 [retrieved on Sep. 3, 2008] Retrieved from the internet: http://www.ncbi.nlm.nih.gov/entrez/viewer.fcgi?db=protein&id=119568922.
National Center for Biotechnology Information [online], GenBank Entrez Protein Accession No. EDL89402 [retrieved on Sep. 3, 2008] Retrieved from the internet: http://www.ncbi.nlm.nih.gov/entrez/viewer.fcgi?db=protein&id=149034665.
National Center for Biotechnology Information [online], GenBank Entrez CoreNucleotide Accession No. EU107280 [retrieved on Sep. 3, 2008] Retrieved from the internet: http://www.ncbi.nlm.nih.gov/entrez/viewer.fcgi?db=nuccore&id=157142987.
National Center for Biotechnology Information [online], GenBank Entrez CoreNucleotide Accession No. NM_000165 [retrieved on Sep. 3, 2008] Retrieved from the internet: http://www.ncbi.nlm.nih.gov/entrez/viewer.fcgi?db=nuccore&id=122939163.
National Center for Biotechnology Information [online], GenBank Entrez CoreNucleotide Accession No. NM_000166 [retrieved on Sep. 3, 2008] Retrieved from the internet: http://www.ncbi.nlm.nih.gov/entrez/viewer.fcgi?db=nuccore&id=195222738.
National Center for Biotechnology Information [online], GenBank Entrez CoreNucleotide Accession No. NM_000218 [retrieved on Sep. 3, 2008] Retrieved from the internet: http://www.ncbi.nlm.nih.gov/entrez/viewer.fcgi?db=nuccore&id=32479526.
National Center for Biotechnology Information [online], GenBank Entrez CoreNucleotide Accession No. NM_000363 [retrieved on Sep. 3, 2008] Retrieved from the internet: http://www.ncbi.nlm.nih.gov/entrez/viewer.fcgi?db=nuccore&id=151101269.
National Center for Biotechnology Information [online], GenBank Entrez CoreNucleotide Accession No. NM_000432 [retrieved on Sep. 3, 2008] Retrieved from the internet: http://www.ncbi.nlm.nih.gov/entrez/viewer.fcgi?db=nuccore&id=190358510.
National Center for Biotechnology Information [online], GenBank Entrez CoreNucleotide Accession No. NM_000719 [retrieved on Sep. 3, 2008] Retrieved from the internet: http://www.ncbi.nlm.nih.gov/entrez/viewer.fcgi?db=nuccore&id=193788716.

(56) References Cited

OTHER PUBLICATIONS

National Center for Biotechnology Information [online], GenBank Entrez CoreNucleotide Accession No. NM_000891 [retrieved on Sep. 3, 2008] Retrieved from the internet: http://www.ncbi.nlm.nih.gov/entrez/viewer.fcgi?db=nuccore&id=22095339.
National Center for Biotechnology Information [online], GenBank Entrez CoreNucleotide Accession No. NM_001001787 [retrieved on Sep. 3, 2008] Retrieved from the internet: http://www.ncbi.nlm.nih.gov/entrez/viewer.fcgi?db=nuccore&id=49574488.
National Center for Biotechnology Information [online], GenBank Entrez CoreNucleotide Accession No. NM_001018007 [retrieved on Sep. 3, 2008] Retrieved from the internet: http://www.ncbi.nlm.nih.gov/entrez/viewer.fcgi?db=nuccore&id=63252901.
National Center for Biotechnology Information [online], GenBank Entrez CoreNucleotide Accession No. NM_001024690 [retrieved on Sep. 3, 2008] Retrieved from the internet: http://www.ncbi.nlm.nih.gov/entrez/viewer.fcgi?db=nuccore&id=125991763.
National Center for Biotechnology Information [online], GenBank Entrez CoreNucleotide Accession No. NM_001039321 [retrieved on Sep. 3, 2008] Retrieved from the internet: http://www.ncbi.nlm.nih.gov/entrez/viewer.fcgi?db=nuccore&id=86129553.
National Center for Biotechnology Information [online], GenBank Entrez CoreNucleotide Accession No. NM_001102 [retrieved on Sep. 3, 2008] Retrieved from the internet: http://www.ncbi.nlm.nih.gov/entrez/viewer.fcgi?db=nuccore&id=194097348.
National Center for Biotechnology Information [online], GenBank Entrez CoreNucleotide Accession No. NM_001103 [retrieved on Sep. 3, 2008] Retrieved from the internet: http://www.ncbi.nlm.nih.gov/entrez/viewer.fcgi?db=nuccore&id=161377421.
National Center for Biotechnology Information [online], GenBank Entrez CoreNucleotide Accession No. NM_001194 [retrieved on Sep. 3, 2008] Retrieved from the internet: http://www.ncbi.nlm.nih.gov/entrez/viewer.fcgi?db=nuccore&id=156071469.
National Center for Biotechnology Information [online], GenBank Entrez CoreNucleotide Accession No. NM_002472 [retrieved on Sep. 3, 2008] Retrieved from the internet: http://www.ncbi.nlm.nih.gov/entrez/viewer.fcgi?db=nuccore&id=153945789.
National Center for Biotechnology Information [online], GenBank Entrez CoreNucleotide Accession No. NM_004004 [retrieved on Sep. 3, 2008] Retrieved from the internet: http://www.ncbi.nlm.nih.gov/entrez/viewer.fcgi?db=nuccore&id=195539329.
National Center for Biotechnology Information [online], GenBank Entrez CoreNucleotide Accession No. NM_004924 [retrieved on Sep. 3, 2008] Retrieved from the internet: http://www.ncbi.nlm.nih.gov/entrez/viewer.fcgi?db=nuccore&id=34452697.
National Center for Biotechnology Information [online], GenBank Entrez CoreNucleotide Accession No. NM_004981 [retrieved on Sep. 3, 2008] Retrieved from the internet: http://www.ncbi.nlm.nih.gov/entrez/viewer.fcgi?db=nuccore&id=4826797.
National Center for Biotechnology Information [online], GenBank Entrez CoreNucleotide Accession No. NM_005267 [retrieved on Sep. 3, 2008] Retrieved from the internet: http://www.ncbi.nlm.nih.gov/entrez/viewer.fcgi?db=nuccore&id=55953075.
National Center for Biotechnology Information [online], GenBank Entrez CoreNucleotide Accession No. NM_005268 [retrieved on Sep. 3, 2008] Retrieved from the internet: http://www.ncbi.nlm.nih.gov/entrez/viewer.fcgi?db=nuccore&id=31542847.
National Center for Biotechnology Information [online], GenBank Entrez CoreNucleotide Accession No. NM_005477 [retrieved on Sep. 3, 2008] Retrieved from the internet: http://www.ncbi.nlm.nih.gov/entrez/viewer.fcgi?db=nuccore&id=4885406.
National Center for Biotechnology Information [online], GenBank Entrez CoreNucleotide Accession No. NM_005497 [retrieved on Sep. 3, 2008] Retrieved from the internet: http://www.ncbi.nlm.nih.gov/entrez/viewer.fcgi?db=nuccore&id=122939170.
National Center for Biotechnology Information [online], GenBank Entrez CoreNucleotide Accession No. NM_006783 [retrieved on Sep. 3, 2008] Retrieved from the internet: http://www.ncbi.nlm.nih.gov/entrez/viewer.fcgi?db=nuccore&id=194306613.
National Center for Biotechnology Information [online], GenBank Entrez CoreNucleotide Accession No. NM_010408 [retrieved on Sep. 3, 2008] Retrieved from the internet: http://www.ncbi.nlm.nih.gov/entrez/viewer.fcgi?db=nuccore&id=6754167.
National Center for Biotechnology Information [online], GenBank Entrez CoreNucleotide Accession No. NM_020660 [retrieved on Sep. 3, 2008] Retrieved from the internet: http://www.ncbi.nlm.nih.gov/entrez/viewer.fcgi?db=nuccore&id=10190697.
National Center for Biotechnology Information [online], GenBank Entrez CoreNucleotide Accession No. NM_020897 [retrieved on Sep. 3, 2008] Retrieved from the internet: http://www.ncbi.nlm.nih.gov/entrez/viewer.fcgi?db=nuccore&id=38327036.
National Center for Biotechnology Information [online], GenBank Entrez CoreNucleotide Accession No. NM_021012 [retrieved on Sep. 3, 2008] Retrieved from the internet: http://www.ncbi.nlm.nih.gov/entrez/viewer.fcgi?db=nuccore&id=118582281.
National Center for Biotechnology Information [online], GenBank Entrez CoreNucleotide Accession No. NM_021954 [retrieved on Sep. 3, 2008] Retrieved from the internet: http://www.ncbi.nlm.nih.gov/entrez/viewer.fcgi?db=nuccore&id=115392136.
National Center for Biotechnology Information [online], GenBank Entrez CoreNucleotide Accession No. NM_030772 [retrieved on Sep. 3, 2008] Retrieved from the internet: http://www.ncbi.nlm.nih.gov/entrez/viewer.fcgi?db=nuccore&id=62079290.
National Center for Biotechnology Information [online], GenBank Entrez CoreNucleotide Accession No. NM_053684 [retrieved on Sep. 3, 2008] Retrieved from the internet: http://www.ncbi.nlm.nih.gov/entrez/viewer.fcgi?db=nuccore&id=50878266.
National Center for Biotechnology Information [online], GenBank Entrez CoreNucleotide Accession No. NM_133497 [retrieved on Sep. 3, 2008] Retrieved from the internet: http://www.ncbi.nlm.nih.gov/entrez/viewer.fcgi?db=nuccore&id=28329446.
National Center for Biotechnology Information [online], GenBank Entrez CoreNucleotide Accession No. NM_152219 [retrieved on Sep. 3, 2008] Retrieved from the internet: http://www.ncbi.nlm.nih.gov/entrez/viewer.fcgi?db=nuccore&id=148839377.
National Center for Biotechnology Information [online], GenBank Entrez CoreNucleotide Accession No. NM_152263 [retrieved on Sep. 3, 2008] Retrieved from the internet: http://www.ncbi.nlm.nih.gov/entrez/viewer.fcgi?db=nuccore&id=114155139.
National Center for Biotechnology Information [online], GenBank Entrez CoreNucleotide Accession No. NM_152868 [retrieved on Sep. 3, 2008] Retrieved from the internet: http://www.ncbi.nlm.nih.gov/entrez/viewer.fcgi?db=nuccore&id=23110983.
National Center for Biotechnology Information [online], GenBank Entrez CoreNucleotide Accession No. NM_153212 [retrieved on Sep. 3, 2008] Retrieved from the internet: http://www.ncbi.nlm.nih.gov/entrez/viewer.fcgi?db=nuccore&id=23397463.
National Center for Biotechnology Information [online], GenBank Entrez CoreNucleotide Accession No. NM_153368 [retrieved on Sep. 3, 2008] Retrieved from the internet: http://www.ncbi.nlm.nih.gov/entrez/viewer.fcgi?db=nuccore&id=145699104.
National Center for Biotechnology Information [online], GenBank Entrez CoreNucleotide Accession No. NM_170720 [retrieved on Sep. 3, 2008] Retrieved from the internet: http://www.ncbi.nlm.nih.gov/entrez/viewer.fcgi?db=nuccore&id=25777634.
National Center for Biotechnology Information [online], GenBank Entrez CoreNucleotide Accession No. NM_181538 [retrieved on Sep. 3, 2008] Retrieved from the internet: http://www.ncbi.nlm.nih.gov/entrez/viewer.fcgi?db=nuccore&id=31559820.
National Center for Biotechnology Information [online], GenBank Entrez CoreNucleotide Accession No. NM_198568 [retrieved on Sep. 3, 2008] Retrieved from the internet: http://www.ncbi.nlm.nih.gov/entrez/viewer.fcgi?db=nuccore&id=38348411.
National Center for Biotechnology Information [online], GenBank Entrez Protein Accession No. NP_000156 [retrieved on Sep. 3, 2008] Retrieved from the internet: http://www.ncbi.nlm.nih.gov/entrez/viewer.fcgi?db=protein&id=4504001.
National Center for Biotechnology Information [online], GenBank Entrez Protein Accession No. NP_000157 [retrieved on Sep. 3, 2008] Retrieved from the internet: http://www.ncbi.nlm.nih.gov/entrez/viewer.fcgi?db=protein&id=4504005.

(56) References Cited

OTHER PUBLICATIONS

National Center for Biotechnology Information [online], GenBank Entrez Protein Accession No. NP_000209 [retrieved on Sep. 3, 2008] Retrieved from the internet: http://www.ncbi.nlm.nih.gov/entrez/viewer.fcgi?db=protein&id=32479527.

National Center for Biotechnology Information [online], GenBank Entrez Protein Accession No. NP_000248 [retrieved on Sep. 3, 2008] Retrieved from the internet: http://www.ncbi.nlm.nih.gov/entrez/viewer.fcgi?db=protein&id=115496169.

National Center for Biotechnology Information [online], GenBank Entrez CoreNucleotide Accession No. NP_000354 [retrieved on Sep. 3, 2008] Retrieved from the internet: http://www.ncbi.nlm.nih.gov/entrez/viewer.fcgi?db=protein&id=151101270.

National Center for Biotechnology Information [online], GenBank Entrez Protein Accession No. NP_000423 [retrieved on Sep. 3, 2008] Retrieved from the internet: http://www.ncbi.nlm.nih.gov/entrez/viewer.fcgi?db=protein&id=94981553.

National Center for Biotechnology Information [online], GenBank Entrez Protein Accession No. NP_000710 [retrieved on Sep. 3, 2008] Retrieved from the internet: http://www.ncbi.nlm.nih.gov/entrez/viewer.fcgi?db=protein&id=120433602.

National Center for Biotechnology Information [online], GenBank Entrez Protein Accession No. NP_000882 [retrieved on Sep. 3, 2008] Retrieved from the internet: http://www.ncbi.nlm.nih.gov/entrez/viewer.fcgi?db=protein&id=4504835.

National Center for Biotechnology Information [online], GenBank Entrez Protein Accession No. NP_001001430 [retrieved on Sep. 3, 2008] Retrieved from the internet: http://www.ncbi.nlm.nih.gov/entrez/viewer.fcgi?db=protein&id=48255879.

National Center for Biotechnology Information [online], GenBank Entrez Protein Accession No. NP_001001787 [retrieved on Sep. 3, 2008] Retrieved from the internet: http://www.ncbi.nlm.nih.gov/entrez/viewer.fcgi?db=protein&id=49574489.

National Center for Biotechnology Information [online], GenBank Entrez Protein Accession No. NP_001005752 [retrieved on Sep. 3, 2008] Retrieved from the internet: http://www.ncbi.nlm.nih.gov/entrez/viewer.fcgi?db=protein&id=54607056.

National Center for Biotechnology Information [online], GenBank Entrez Protein Accession No. NP_001018007 [retrieved on Sep. 3, 2008] Retrieved from the internet: http://www.ncbi.nlm.nih.gov/entrez/viewer.fcgi?db=protein&id=63252902.

National Center for Biotechnology Information [online], GenBank Entrez Protein Accession No. NP_001019861 [retrieved on Sep. 3, 2008] Retrieved from the internet: http://www.ncbi.nlm.nih.gov/entrez/viewer.fcgi?db=protein&id=125991764.

National Center for Biotechnology Information [online], GenBank Entrez Protein Accession No. NP_001029807 [retrieved on Sep. 3, 2008] Retrieved from the internet: http://www.ncbi.nlm.nih.gov/entrez/viewer.fcgi?db=protein&id=77736221.

National Center for Biotechnology Information [online], GenBank Entrez Protein Accession No. NP_001034410 [retrieved on Sep. 3, 2008] Retrieved from the internet: http://www.ncbi.nlm.nih.gov/entrez/viewer.fcgi?db=protein&id=86129554.

National Center for Biotechnology Information [online], GenBank Entrez Protein Accession No. NP_001093 [retrieved on Sep. 3, 2008] Retrieved from the internet: http://www.ncbi.nlm.nih.gov/entrez/viewer.fcgi?db=protein&id=4501891.

National Center for Biotechnology Information [online], GenBank Entrez Protein Accession No. NP_001094 [retrieved on Sep. 3, 2008] Retrieved from the internet: http://www.ncbi.nlm.nih.gov/entrez/viewer.fcgi?db=protein&id=4501893.

National Center for Biotechnology Information [online], GenBank Entrez Protein Accession No. NP_001095 [retrieved on Sep. 3, 2008] Retrieved from the internet: http://www.ncbi.nlm.nih.gov/entrez/viewer.fcgi?db=protein&id=4557241.

National Center for Biotechnology Information [online], GenBank Entrez Protein Accession No. NP_001185 [retrieved on Sep. 3, 2008] Retrieved from the internet: http://www.ncbi.nlm.nih.gov/entrez/viewer.fcgi?db=protein&id=156071470.

National Center for Biotechnology Information [online], GenBank Entrez Protein Accession No. NP_003272 [retrieved on Sep. 3, 2008] Retrieved from the internet: http://www.ncbi.nlm.nih.gov/entrez/viewer.fcgi?db=protein&id=56682969.

National Center for Biotechnology Information [online], GenBank Entrez Protein Accession No. NP_003995 [retrieved on Sep. 3, 2008] Retrieved from the internet: http://www.ncbi.nlm.nih.gov/entrez/viewer.fcgi?db=protein&id=42558283.

National Center for Biotechnology Information [online], GenBank Entrez Protein Accession No. NP_004915 [retrieved on Sep. 3, 2008] Retrieved from the internet: http://www.ncbi.nlm.nih.gov/entrez/viewer.fcgi?db=protein&id=12025678.

National Center for Biotechnology Information [online], GenBank Entrez Protein Accession No. NP_004972 [retrieved on Sep. 3, 2008] Retrieved from the internet: http://www.ncbi.nlm.nih.gov/entrez/viewer.fcgi?db=protein&id=4826798.

National Center for Biotechnology Information [online], GenBank Entrez Protein Accession No. NP_005258 [retrieved on Sep. 3, 2008] Retrieved from the internet: http://www.ncbi.nlm.nih.gov/entrez/viewer.fcgi?db=protein&id=55953076.

National Center for Biotechnology Information [online], GenBank Entrez Protein Accession No. NP_005259 [retrieved on Sep. 3, 2008] Retrieved from the internet: http://www.ncbi.nlm.nih.gov/entrez/viewer.fcgi?db=protein&id=10835079.

National Center for Biotechnology Information [online], GenBank Entrez Protein Accession No. NP_005468 [retrieved on Sep. 3, 2008] Retrieved from the internet: http://www.ncbi.nlm.nih.gov/entrez/viewer.fcgi?db=protein&id=4885407.

National Center for Biotechnology Information [online], GenBank Entrez Protein Accession No. NP_005488 [retrieved on Sep. 3, 2008] Retrieved from the internet: http://www.ncbi.nlm.nih.gov/entrez/viewer.fcgi?db=protein&id=69122473.

National Center for Biotechnology Information [online], GenBank Entrez Protein Accession No. NP_006774 [retrieved on Sep. 3, 2008] Retrieved from the internet: http://www.ncbi.nlm.nih.gov/entrez/viewer.fcgi?db=protein&id=40254837.

National Center for Biotechnology Information [online], GenBank Entrez Protein Accession No. NP_065711 [retrieved on Sep. 3, 2008] Retrieved from the internet: http://www.ncbi.nlm.nih.gov/entrez/viewer.fcgi?db=protein&id=10190698.

National Center for Biotechnology Information [online], GenBank Entrez Protein Accession No. NP_065948 [retrieved on Sep. 3, 2008] Retrieved from the internet: http://www.ncbi.nlm.nih.gov/entrez/viewer.fcgi?db=protein&id=38327037.

National Center for Biotechnology Information [online], GenBank Entrez Protein Accession No. NP_066292 [retrieved on Sep. 3, 2008] Retrieved from the internet: http://www.ncbi.nlm.nih.gov/entrez/viewer.fcgi?db=protein&id=23110982.

National Center for Biotechnology Information [online], GenBank Entrez CoreNucleotide Accession No. NP_066550 [retrieved on Sep. 3, 2008] Retrieved from the internet: http://www.ncbi.nlm.nih.gov/entrez/viewer.fcgi?db=protein&id=116325989.

National Center for Biotechnology Information [online], GenBank Entrez Protein Accession No. NP_068773 [retrieved on Sep. 3, 2008] Retrieved from the internet: http://www.ncbi.nlm.nih.gov/entrez/viewer.fcgi?db=protein&id=22779877.

National Center for Biotechnology Information [online], GenBank Entrez Protein Accession No. NP_110399 [retrieved on Sep. 3, 2008] Retrieved from the internet: http://www.ncbi.nlm.nih.gov/entrez/viewer.fcgi?db=protein&id=31542845.

National Center for Biotechnology Information [online], GenBank Entrez Protein Accession No. NP_112267 [retrieved on Sep. 3, 2008] Retrieved from the internet: http://www.ncbi.nlm.nih.gov/entrez/viewer.fcgi?db=protein&id=13591902.

National Center for Biotechnology Information [online], GenBank Entrez Protein Accession No. NP_445827 [retrieved on Sep. 3, 2008] Retrieved from the internet: http://www.ncbi.nlm.nih.gov/entrez/viewer.fcgi?db=protein&id=16758108.

National Center for Biotechnology Information [online], GenBank Entrez Protein Accession No. NP_446136 [retrieved on Sep. 3, 2008] Retrieved from the internet: http://www.ncbi.nlm.nih.gov/entrez/viewer.fcgi?db=protein&id=50878267.

(56) References Cited

OTHER PUBLICATIONS

National Center for Biotechnology Information [online], GenBank Entrez Protein Accession No. NP_598004 [retrieved on Sep. 3, 2008] Retrieved from the internet: http://www.ncbi.nlm.nih.gov/entrez/viewer.fcgi?db=protein&id=19424136.

National Center for Biotechnology Information [online], GenBank Entrez Protein Accession No. NP_598917 [retrieved on Sep. 3, 2008] Retrieved from the internet: http://www.ncbi.nlm.nih.gov/entrez/viewer.fcgi?db=protein&id=61097906.

National Center for Biotechnology Information [online], GenBank Entrez Protein Accession No. NP_609903 [retrieved on Sep. 3, 2008] Retrieved from the internet: http://www.ncbi.nlm.nih.gov/entrez/viewer.fcgi?db=protein&id=62484243.

National Center for Biotechnology Information [online], GenBank Entrez Protein Accession No. NP_689343 [retrieved on Sep. 3, 2008] Retrieved from the internet: http://www.ncbi.nlm.nih.gov/entrez/viewer.fcgi?db=protein&id=148839378.

National Center for Biotechnology Information [online], GenBank Entrez Protein Accession No. NP_690607 [retrieved on Sep. 3, 2008] Retrieved from the internet: http://www.ncbi.nlm.nih.gov/entrez/viewer.fcgi?db=protein&id=23110984.

National Center for Biotechnology Information [online], GenBank Entrez Protein Accession No. NP_694944 [retrieved on Sep. 3, 2008] Retrieved from the internet: http://www.ncbi.nlm.nih.gov/entrez/viewer.fcgi?db=protein&id=23397464.

National Center for Biotechnology Information [online], GenBank Entrez Protein Accession No. NP_699199 [retrieved on Sep. 3, 2008] Retrieved from the internet: http://www.ncbi.nlm.nih.gov/entrez/viewer.fcgi?db=protein&id=145699105.

National Center for Biotechnology Information [online], GenBank Entrez Protein Accession No. NP_733838 [retrieved on Sep. 3, 2008] Retrieved from the internet: http://www.ncbi.nlm.nih.gov/entrez/viewer.fcgi?db=protein&id=25777635.

National Center for Biotechnology Information [online], GenBank Entrez Protein Accession No. NP_853516 [retrieved on Sep. 3, 2008] Retrieved from the internet: http://www.ncbi.nlm.nih.gov/entrez/viewer.fcgi?db=protein&id=31559821.

National Center for Biotechnology Information [online], GenBank Entrez Protein Accession No. NP_940970 [retrieved on Sep. 3, 2008] Retrieved from the internet: http://www.ncbi.nlm.nih.gov/entrez/viewer.fcgi?db=protein&id=38348412.

National Center for Biotechnology Information [online], GenBank Entrez Protein Accession No. O18839 [retrieved on Sep. 3, 2008] Retrieved from the internet: http://www.ncbi.nlm.nih.gov/entrez/viewer.fcgi?db=protein&id=3024031.

National Center for Biotechnology Information [online], GenBank Entrez Protein Accession No. O19182 [retrieved on Sep. 3, 2008] Retrieved from the internet: http://www.ncbi.nlm.nih.gov/entrez/viewer.fcgi?db=protein&id=9910716.

National Center for Biotechnology Information [online], GenBank Entrez Protein Accession No. O70596 [retrieved on Sep. 3, 2008] Retrieved from the internet: http://www.ncbi.nlm.nih.gov/entrez/viewer.fcgi?db=protein&id=54036089.

National Center for Biotechnology Information [online], GenBank Entrez Protein Accession No. O75712 [retrieved on Sep. 3, 2008] Retrieved from the internet: http://www.ncbi.nlm.nih.gov/entrez/viewer.fcgi?db=protein&id=6014758.

National Center for Biotechnology Information [online], GenBank Entrez Protein Accession No. P08034 [retrieved on Sep. 3, 2008] Retrieved from the internet: http://www.ncbi.nlm.nih.gov/entrez/viewer.fcgi?db=protein&id=117688.

National Center for Biotechnology Information [online], GenBank Entrez Protein Accession No. P12883 [retrieved on Sep. 3, 2008] Retrieved from the internet: http://www.ncbi.nlm.nih.gov/entrez/viewer.fcgi?db=protein&id=83304912.

National Center for Biotechnology Information [online], GenBank Entrez Protein Accession No. P13533 [retrieved on Sep. 3, 2008] Retrieved from the internet: http://www.ncbi.nlm.nih.gov/entrez/viewer.fcgi?db=protein&id=3041706.

National Center for Biotechnology Information [online], GenBank Entrez Protein Accession No. P19429 [retrieved on Sep. 3, 2008] Retrieved from the internet: http://www.ncbi.nlm.nih.gov/entrez/viewer.fcgi?db=protein&id=136213.

National Center for Biotechnology Information [online], GenBank Entrez Protein Accession No. P35561 [retrieved on Sep. 3, 2008] Retrieved from the internet: http://www.ncbi.nlm.nih.gov/entrez/viewer.fcgi?db=protein&id=547735.

National Center for Biotechnology Information [online], GenBank Entrez Protein Accession No. P35609 [retrieved on Sep. 3, 2008] Retrieved from the internet: http://www.ncbi.nlm.nih.gov/entrez/viewer.fcgi?db=protein&id=543742.

National Center for Biotechnology Information [online], GenBank Entrez Protein Accession No. P49656 [retrieved on Sep. 3, 2008] Retrieved from the internet: http://www.ncbi.nlm.nih.gov/entrez/viewer.fcgi?db=protein&id=1352481.

National Center for Biotechnology Information [online], GenBank Entrez Protein Accession No. P52185 [retrieved on Sep. 3, 2008] Retrieved from the internet: http://www.ncbi.nlm.nih.gov/entrez/viewer.fcgi?db=protein&id=1708549.

National Center for Biotechnology Information [online], GenBank Entrez Protein Accession No. P52187 [retrieved on Sep. 3, 2008] Retrieved from the internet: http://www.ncbi.nlm.nih.gov/entrez/viewer.fcgi?db=protein&id=1708554.

National Center for Biotechnology Information [online], GenBank Entrez Protein Accession No. P52188 [retrieved on Sep. 3, 2008] Retrieved from the internet: http://www.ncbi.nlm.nih.gov/entrez/viewer.fcgi?db=protein&id=1708555.

National Center for Biotechnology Information [online], GenBank Entrez Protein Accession No. P52189 [retrieved on Sep. 3, 2008] Retrieved from the internet: http://www.ncbi.nlm.nih.gov/entrez/viewer.fcgi?db=protein&id=1708551.

National Center for Biotechnology Information [online], GenBank Entrez Protein Accession No. P52190 [retrieved on Sep. 3, 2008] Retrieved from the internet: http://www.ncbi.nlm.nih.gov/entrez/viewer.fcgi?db=protein&id=1708552.

National Center for Biotechnology Information [online], GenBank Entrez Protein Accession No. P63252 [retrieved on Sep. 3, 2008] Retrieved from the internet: http://www.ncbi.nlm.nih.gov/entrez/viewer.fcgi?db=protein&id=54037433.

National Center for Biotechnology Information [online], GenBank Entrez Protein Accession No. Q14500 [retrieved on Sep. 3, 2008] Retrieved from the internet: http://www.ncbi.nlm.nih.gov/entrez/viewer.fcgi?db=protein&id=77416868.

National Center for Biotechnology Information [online], GenBank Entrez Protein Accession No. Q5T442 [retrieved on Sep. 3, 2008] Retrieved from the internet: http://www.ncbi.nlm.nih.gov/entrez/viewer.fcgi?db=protein&id=74744875.

National Center for Biotechnology Information [online], GenBank Entrez Protein Accession No. Q64198 [retrieved on Sep. 3, 2008] Retrieved from the internet: http://www.ncbi.nlm.nih.gov/entrez/viewer.fcgi?db=protein&id=2493598.

National Center for Biotechnology Information [online], GenBank Entrez Protein Accession No. Q64273 [retrieved on Sep. 3, 2008] Retrieved from the internet: http://www.ncbi.nlm.nih.gov/entrez/viewer.fcgi?db=protein&id=2493597.

National Center for Biotechnology Information [online], GenBank Entrez Protein Accession No. Q6PEY0 [retrieved on Sep. 3, 2008] Retrieved from the internet: http://www.ncbi.nlm.nih.gov/entrez/viewer.fcgi?db=protein&id=74749171.

National Center for Biotechnology Information [online], GenBank Entrez Protein Accession No. Q8JZN3 [retrieved on Sep. 3, 2008] Retrieved from the internet: http://www.ncbi.nlm.nih.gov/entrez/viewer.fcgi?db=protein&id=54036145.

National Center for Biotechnology Information [online], GenBank Entrez Protein Accession No. Q9UL51 [retrieved on Sep. 3, 2008] Retrieved from the internet: http://www.ncbi.nlm.nih.gov/entrez/viewer.fcgi?db=protein&id=108935843.

National Center for Biotechnology Information [online], GenBank Entrez CoreNucleotide Accession No. X80417 [retrieved on Sep. 3, 2008] Retrieved from the internet: http://www.ncbi.nlm.nih.gov/entrez/viewer.fcgi?db=nuccore&id=550388.

(56) References Cited

OTHER PUBLICATIONS

National Center for Biotechnology Information [online], GenBank Entrez CoreNucleotide Accession No. Y13033 [retrieved on Sep. 3, 2008] Retrieved from the internet: http://www.ncbi.nlm.nih.gov/entrez/viewer.fcgi?db=nuccore&id=2463214.
Plaster, N.M. et al. (2001) "Mutations in Kir2.1 Cause the Developmental and Episodic Electrical Phenotypes of Andersen's Syndrome," Cell 105:511-519.
Proenza, C. et al. (2002) "Pacemaker Channels Produce an Instantaneous Current," The Journal of Biological Chemistry 277(7):5101-5109.
Qu, J. et al. (2001) "HCN2 Overexpression in Newborn and Adult Ventricular Myocytes: Distinct Effects on Gating and Excitability," Circulation Research 89:e8-e14.
Qu, J. et al. (2003) "Expression and Function of a Biological Pacemaker in Canine Heart," Circulation 107:1106-1109.
Satoh, H. (2003) "Sino-Atrial Nodal Cells of Mammalian Hearts: Ionic Currents and Gene Expression of Pacemaker Ionic Channels," J. Smooth Muscle Res. 39(5):175-193.
Schram, G. et al. (2002) "Differential Distribution of Cardiac Ion Channel Expression as a Basis for Regional Specialization in Electrical Function," Circulation Research 90:939-950.
Shi, W. et al. (1999) "Distribution and Prevalence of Hyperpolarization-Activated Cation Channel (HCN) mRNA Expression in Cardiac Tissues," Circulation Research 85:e1-e6.
Shipley, J.M. et al. (1991) "Analysis of the 5' Flanking Region of the Human β-Glucuronidase Gene," Genomics 10:1009-1018.
Siu, C.W. et al. (2006) "HCN-Encoded Pacemaker Channels: From Physiology and Biophysics to Bioengineering," J. Membrane Biol. 214(3):115-122.
Siu, C.W. et al. (2007) "Human Embryonic Stem Cell-Derived Cardiomyocytes for Heart Therapies," Cardiovascular & Haematological Disorders-Drug Targets 7(2):145-152.
Smits, P.C. (2004) "Myocardial repair with autologous skeletal myoblasts: a review of the clinical studies and problems," Minerva Cardioangiol. 52:525-535.
Sobey, C.G. et al. (2000) "Knockout Blow for Channel Identity Crisis, Vasodilation to Potassium Is Mediated via Kir2.1," Circulation Research 87:83-84.
Tomita, Y. et al. (2007) "Application of mesenchymal stem cell-derived cardiomyocytes as bio-pacemakers: current status and problems to be solved," Med. Bio. Eng. Comput. 45:209-220.
Tsang, S.Y. et al. (2004) "Critical intra-linker interactions of HCN1-encoded pacemaker channels revealed by interchange of S3-S4 determinants," Biochem. Biophys. Res. Commun. 322:652-658.
Tsang, S.Y. et al. (2004) "Dissecting the Structural and Functional Roles of the S3-S4 Linker of Pacemaker (HCN) Channels by Systematic Length Alterations," The Journal of Biological Chemistry 279(42):43752-43759.
Tse, H-F. et al. (2006) "Bioartificial Sinus Node Constructed via In Vivo Gene Transfer of an Engineered Pacemaker HCN Channel Reduces the Dependence on Electronic Pacemaker in a Sick-Sinus Syndrome Model," Circulation 114:1000-1011.
Vinogradova, T.M. et al. (2005) "Rhythmic $Ca^{2+}$ Oscillations Drive Sinoatrial Nodal Cell Pacemaker Function to Make the Heart Tick," Ann. N.Y. Acad. Sci. 1047:138-156.
Wainger, B.J. et al. (2001) "Molecular mechanism of cAMP modulation of HCN pacemaker channels," Nature 411:805-810.
Wang, K.W. et al. (2005) "Electrophysiological Properties of Pluripotent Human and Mouse Embryonic Stem Cells," Stem Cells 23(10):1526-1534.
Watanabe, E-I. et al. (1996) "Inactivation of the calcium current is involved in overdrive suppression of rabbit sinoatrial node cells," Am. J. Physiol. Heart Circ. Physiol. 271 (Heart Circ. Physiol. 40):H2097-H2107.
Wellner-Kienitz, M-C. et al. (2004) "Voltage dependence of ATP-dependent $K^+$ current in rat cardiac myocytes is affected by $I_{Ki1}$ and $I_{K(Ach)}$," J. Physiol. 561(2):459-469.
Wilson, J.M. et al. (1990) "Expression of human adenosine deaminase in mice reconstituted with retrovirus-transduced hematopoietic stem cells," Proc. Natl. Acad. Sci. USA 87:439-443.
Wobus, A.M. et al. (2002) "Embryonic stem cells as a model to study cardiac, skeletal muscle, and vascular smooth muscle cell differentiation," Methods in Molecular Biology 185:127-156.
Xu, R. et al. (2001) "Quantitative comparison of expression with adeno-associated virus (AAV-2) brain-specific gene cassettes," Gene Therapy 8:1323-1332.
Xu, C. et al. (2002) "Characterization and Enrichment of Cardiomyocytes Derived From Human Embryonic Stem Cells," Circulation Research 91:501-508.
Xue, T. et al. (2002) "Dominant-Negative Suppression of HCN1- and HCN2-Encoded Pacemaker Currents by an Engineered HCN1 Construct: Insights Into Structure-Function Relationships and Multimerization," Circulation Research 90:1267-1273.
Xue, T. et al. (2002) "An external determinant in the S5-P linker of the pacemaker (HCN) channel identified by sulfhydryl modification," The Journal of Biological Chemistry 277(48):46233-46242.
Xue, T. et al. (2007) "Mechanistic role of $I_f$ revealed by induction of ventricular automaticity by somatic gene transfer of gating-engineered pacemaker (HCN) channels," Circulation 115:1839-1850.
Yu, H. et al. (1993) "Pacemaker Current Exists in Ventricular Myocytes," Circulation Research 72:232-236.
Zaritsky, J.J. et al. (2000) "Targeted Disruption of Kir2.1 and Kir2.2 Genes Reveals the Essential Role of the Inwardly Rectifying K+ Current in K+-Mediated Vasodilation," Circulation Research 87:160-166.
Zaritsky, J.J. et al. (2001) "The consequences of disrupting cardiac inwardly rectifying $K^+$ current ($I_{K1}$) as revealed by the targeted deletion of the murine Kir2.1 and Kir2.2 genes," Journal of Physiology 533.3:697-710.
Zhang, Y.M. et al. (2002) "Stem cell-derived cardiomyocytes demonstrate arrhythmic potential," Circulation 106:1294-1299.

* cited by examiner

US 9,045,731 B2

COMPOSITIONS AND METHODS FOR IMPROVING THE FUNCTIONAL EFFICACY OF STEM CELL-DERIVED CARDIOMYOCYTES

CROSS-REFERENCE TO RELATED APPLICATIONS

The present application is a national stage application under 35 U.S.C. §371 of International Application No. PCT/US2008/076084, filed Sep. 11, 2008, which in turn claims the benefit under 35 U.S.C. §119(e) of U.S. Provisional Serial No. 60/971,855, filed Sep. 12, 2007, the contents of each of which are hereby incorporated by reference in their entirety into the present disclosure.

STATEMENT OF GOVERNMENT SUPPORT

This invention was made with government support under Contract No. RO1 HL72857 awarded by the National Institutes of Health. The government has certain rights in the invention.

BACKGROUND OF THE INVENTION

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

Congestive heart failure has been recognized as an emerging epidemic in developed countries. In the United States, it is estimated that 4.9 million people suffer from heart failure with an annual incidence of 550,000. Since cardiomyocytes possess very limited regenerating capability, survivors of myocardial infarction, the most common cause of heart failure, often progress to heart failure due to massive myocardial loss. Heart transplantation is currently the last resort for end-stage heart failure, but this is hampered by a severe shortage of donor organs and immune rejection. Thus, cell-based therapies have emerged as promising alternatives.

Human embryonic stem cells (hESCs) possessing the ability to self-renewal and to differentiate essentially into all cell types of our bodies (pluripotency) including highly specialized cells such as cardiomyocytes, hold the promise to replenish/repair cellular functions through cellular transplantation. Prior studies have demonstrated that cellular transplantation of hESC-derived cardiomyocytes to damaged myocardium can improve ventricular contractile function and thus improving congestive heart failure (1-4).

Indeed, hESC-derived CMs (hESC-CMs) display structural and functional properties of early-stage cardiomyocytes (CM), and can functionally integrate with or even electrically pace the recipient heart after transplantation in vivo. Thus, hESCs have the potential to act as an unlimited ex vivo source of cells for transplantation and cell-based therapies of otherwise incurable heart diseases.

However, any cell or tissue utilized for heart tissue reconstitution or transplantation must produce electrically excitable heart tissue with viable calcium handling and contractile functions to mechanically pump blood throughout the body. It has been reported that spontaneously beating hESC-CMs do not have the capacity to mimic a mature cardiomyocyte because they lack functional sarcoplasmic reticulum (SR). The SR is a specialized organelle of cells typically found in smooth and striated muscle. It is a type of smooth endoplasmic reticulum and is defined by its function to store and pump calcium ($Ca^{2+}$) ions. The sarcoplasmic reticulum contains large stores of calcium, which it sequesters and then releases when the cell is depolarized thus triggering muscle contraction.

During an action potential of adult CMs, $Ca^{2+}$ entry into the cytosol through sarcolemmal L-type $Ca^{2+}$ channels triggers the release of $Ca^{2+}$ from the intracellular $Ca^{2+}$ stores (a.k.a. SR) via the ryanodine receptor (RyR). This process, the so-called $Ca^{2+}$-induced $Ca^{2+}$ release (CICR), escalates the cytosolic $Ca^{2+}$ ($[Ca^{2+}]_i$) to activate the contractile apparatus for contraction. In mature ventricular CMs, efficiency of CICR is further improved due to the presence of transverse (t)-tubules or invaginations in the sarcolemma that brings the L-type $Ca^{2+}$ channels closer to RyRs, therefore, decreasing the diffusion distance for $Ca^{2+}$ enabling faster and synchronized activation of CICR across the cell. For relaxation, elevated $[Ca^{2+}]_i$ is pumped back into the SR by the sarco/endoplasmic reticulum $Ca^{2+}$-ATPase (SERCA) and extruded out of the cell by the $Na^+$—$Ca^{2+}$ exchanger (NCX) to return to the resting $[Ca^{2+}]_i$ level. Such a rise and subsequent decay of $[Ca^{2+}]_i$ is known as $Ca^{2+}$ transient. Given the central importance of CICR in cardiac excitation-contraction (EC) coupling, proper $Ca^{2+}$ handling properties of hESC-CMs are therefore crucial for their successful functional integration with the recipient heart after transplantation. Indeed, abnormal $Ca^{2+}$ handling, as in the case of heart failure, can even be arrhythmogenic (e.g. delayed after depolarization). Furthermore, integration of immature hESC-CMs with weaker contractile force relative to the mature CMs in vivo can lead to heterogeneous strain in recipient heart, leading to progression of cardiac hypertrophy and/or arrhythmias.

Thus, it would be beneficial to understand the properties of hESC-CMs with the goal of designing effective strategies or protocols for improving safety and efficiency of hESC-CM transplantation. This invention satisfies this need and provides related advantages as well.

DISCLOSURE OF THE INVENTION

This invention provides compositions and methods to achieve one or more of: maturing and/or enhancing the functions of sarcoplasmic reticulum (SR) in stem cells and/or cardiomyocytes that lack functional SR by, in one aspect, expressing $Ca^{2+}$ handling proteins, such as calsequestrin (CSQ), junctin, triadin, and phospholamban; improving the temporal and spatial synchronization of CICR through development of t-tubules by the expression of proteins involved in t-tubule biogenesis, such as caveolin 3 and amphiphysin 2 or by other means (e.g., electrical and/or mechanical stimulations); promoting functional integration of these cells with the recipient heart after transplantation; and providing therapeutic benefit such as to reduce the arrhythmogenicity of stem cells and/or cardiomyocytes due to immature or improper $Ca^{2+}$ handling properties.

Thus, in one aspect, this invention provides an isolated stem cell or its derivative that has been modified to provide or contain the functional characteristics of the SR and/or t-tubules. The isolated stem cells or their derivatives are modified in one or more of the following manners: by expressing a calcium channel protein; by expressing a calcium pump protein such as the sarcro/endoplasmic reticulum $Ca^{2+}$-ATPase (SERCA) protein; by inhibiting or downregulating expression of the $Na^+/Ca^{2+}$ exchanger (NCX) protein; by expressing a calcium handling protein; by expressing a trasverse (t)-tubule; and/or by expressing a transverse (t)-tubule biogenic protein(s) and/or via other biological or physical means (electrical and/or mechanical stimulations). After the cell has been modified, it may be expanded to a substantially homogenous population (e.g., a clonal population) of these cells or alternatively, differentiated to a more mature cell type. Compositions containing these cells and population of cells are also provided by this invention.

These cells and compositions have therapeutic and diagnostic uses. Non-limiting therapeutic uses include regenerating cardiac tissue, improving cardiac function, restoring electrical homogeneity or action potential of cardiac tissue; and treating or preventing cardiac malfunction such as cardiotoxicity or arrythmogenicity. These methods can be achieved by administering an effective amount of a cell or population of cells or tissue to a host in need thereof. The cells and population of cells can be used diagnostically to screen drug or other therapeutic candidates.

Thus, in one aspect, this invention provides a method of identifying an agent that modulates the transport of calcium ($Ca^{2+}$) ions to and/or from the sarcoplasmic reticulum (SR) in a cell by contacting the cell with an amount of a test agent under conditions effective to modulate the SR's ability to store or pump $Ca^{2+}$ ions, and then measuring any change in $Ca^{2+}$ transient, wherein a change in transit is a measureable feature of the $Ca^{2+}$ transients such as, but not limited to, basal $Ca^{2+}$ levels, amplitude, Vmax upstroke or Vmax decay, identify the test agent as an agent that modulates the transport of $Ca^{2+}$ ions to/from the SR in a cell. The cells useful in this method include, but are not limited to any one of more of a cardiac cell, the isolated stem cells or derivatives thereof, the substantially homogeneous population of stem cells or the derivatives thereof, or the compositions as described herein. In one aspect, the test agent is an oligonucleotide, a polynucleotide, a peptide, a protein, an antibody or an antibody fragment. In yet another aspect, the test agent is an organic molecule, an inorganic molecule or a mixture of an organic or inorganic molecule.

The cells and compositions of the present invention can be used in the manufacture of medicaments and for the treatment of humans and other animals.

BRIEF DESCRIPTION OF THE DRAWINGS

FIG. 8, panels A to C, shows $Ca^{2+}$ transients induced by caffeine and recovery of transients induced by electrical stimulation. A) shows representative tracings and B) shows amplitude of caffeine-induced $Ca^{2+}$ transients. n=20, 12 and 14 for Ad-GFP, Ad-CSQ and Ad-CSQΔ, respectively. C) shows recovery of $Ca^{2+}$ transient amplitude after caffeine application. Data were analyzed at 0 seconds, 16 seconds and 32 seconds after the depletion of SR by caffeine (n=9). Values are expressed as mean±SEM; * $P<0.05$ vs. Ad-CSQ. Overall, CSQ expression facilitates maturation by increasing transient amplitude, hastening the $Ca^{2+}$ transient kinetics, rendering them more adult-like.

FIG. 9, panels A to E, shows electrically induced $Ca^{2+}$ transients. A) Representative tracings of electrically induced $Ca^{2+}$ transients in Ad-GFP, Ad-CSQ and Ad-CSQΔ. Bar graphs summarizing B) basal $Ca^{2+}$, C) amplitude, D) maximum upstroke velocity ($V_{max,\ upstroke}$) and E) maximum decay velocity ($V_{max,\ decay}$) of transients. Values are expressed as mean±SEM; n=20, 13 and 15 for Ad-GFP, Ad-CSQ and Ad-CSQΔ, respectively. * $P<0.05$, ** $P<0.01$ vs. Ad-CSQ. Overall, CSQ expression facilitates maturation by hastening the $Ca^{2+}$ transient kinetics, rendering them more adult-like.

MODES FOR CARRYING OUT THE INVENTION

Definitions

Figure 1:
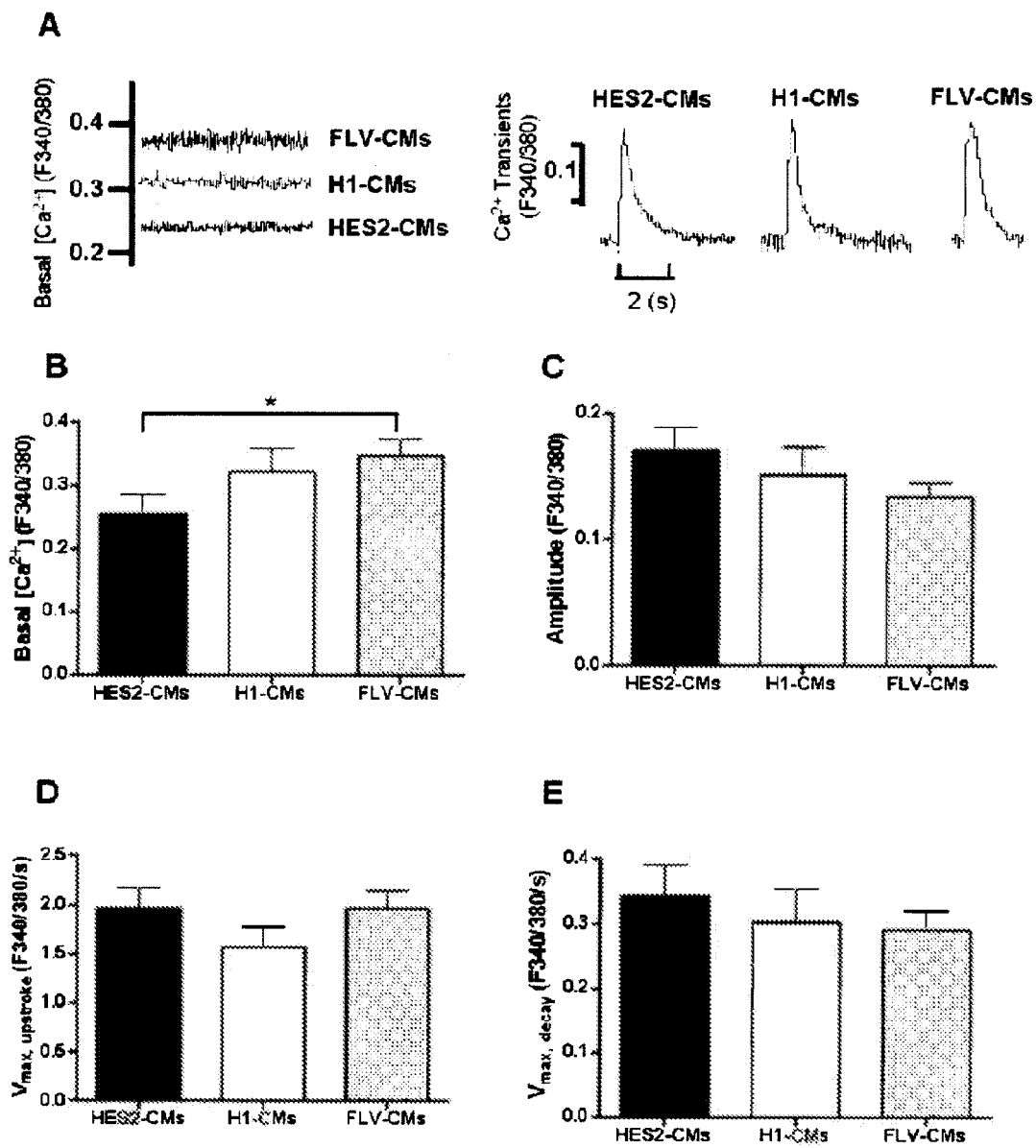
FIG. 1, panels A to E, illustrates the electrically induced $Ca^{2+}$ transients. A) Representative tracings of basal $Ca^{2+}$ and electrically induced $Ca^{2+}$ transients in the human embryonic stem cell lines HES2-, H1- and human fetal left ventrical cardiomyocytes ("FLV-CMs"). Bar graphs summarizing B) basal $Ca^{2+}$, C) amplitude, D) maximum upstroke velocity ($V_{max,\ upstroke}$) and E) maximum decay velocity ($V_{max,\ decay}$) of transients. Values are expressed as mean±SEM; n=17, 18 and 15 for HES2-, H1- and FLV-CMs (obtained from 5 hearts), respectively. * $P<0.05$ vs. FLV-CMs.

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis, Molecular Cloning: A Laboratory Manual, $2^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, a Laboratory Manual; and Animal Cell Culture (R. I. Freshney, ed. (1987)).

All numerical designations, e.g., pH, temperature, time, concentration, and molecular weight, including ranges, are approximations which are varied (+) or (-) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell. "Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to overexpression that is 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher (i.e., and therefore overexpressed) or lower than the expression level detected in a control sample. The term "differentially expressed" also refers to nucleotide sequences in a cell or tissue which are expressed where silent in a control cell or not expressed where expressed in a control cell. A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides;

polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells or cardiomyocytes.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'—OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A Practical Approach" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10× SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated form tissue or cells of dissimilar phenotype or genotype.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. Non-limiting examples of embryonic stem cells are the HES2 (also known as ES02) cell line available from ESI, Singapore and the H1 (also know as WA01) cell line available from WiCells, Madison, Wis. Pluripotent embryonic stem cells can be distinguished from other types of cells by the use of marker including, but not limited to, Oct-4, alkaline phosphatase, CD30, TDGF-1, GCTM-2, Genesis, Germ cell nuclear factor, SSEA1, SSEA3, and SSEA4. A clone is a line of cells that is genetically identical to the originating cell; in this case, a stem cell. In another aspect, a stem cell is cardiac resident stem cells or a stem cell type that possess cardiogenic potential as described in Torella et al. (2006) Nature Clinical Practice Cardiovascular Medicine 3:S8-S13.

The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue. In yet another embodiment, the tissue is comprised of cardiomyocytes.

The term "culturing" refers to the in vitro propagation of cells or organisms on or in media of various kinds It is understood that the descendants of a cell grown in culture may not be completely identical (i.e., morphologically, genetically, or phenotypically) to the parent cell. By "expanded" is meant any proliferation or division of cells.

"Clonal proliferation" refers to the growth of a population of cells by the continuous division of single cells into two identical daughter cells and/or population of identical cells.

As used herein, the "lineage" of a cell defines the heredity of the cell, i.e. its predecessors and progeny. The lineage of a cell places the cell within a hereditary scheme of development and differentiation.

A derivative of a cell or population of cells is a daughter cell of the isolated cell or population of cells. Derivatives include the expanded clonal cells or differentiated cells cultured and propagated from the isolated stem cell or population of stem cells. Derivatives also include already derived stem cells or population of stem cells, such as, but not limited to, stem cell derived cardiomyocytes.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

Examples of cells that differentiate into endodermal lineage include, but are not limited to pleurogenic cells, and hepatogenic cells, cell that give rise to the lining of the intestine, and cells that give rise to pancreogenic and splanchogenic cells.

As used herein, a "pluripotent cell" defines a less differentiated cell that can give rise to at least two distinct (genotypically and/or phenotypically) further differentiated progeny cells. In another aspect, a "pluripotent cell" includes a Induced Pluripotent Stem Cell (iPSC) which is an artificially derived stem cell from a non-pluripotent cell, typically an adult somatic cell, produced by inducing expression of one or more stem cell specific genes. Such stem cell specific genes include, but are not limited to, the family of octamer transcription factors, i.e. Oct-3/4; the family of Sox genes, i.e. Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e. OCT4, NANOG and REX1; or LIN28. Examples of iPSCs are described in Takahashi K. et al. (2007) Cell advance online publication 20 Nov. 2007; Takahashi K. & Yamanaka S. (2006) Cell 126: 663-76; Okita K. et al. (2007) Nature 448: 260-262; Yu, J. et al. (2007) Science advance online publication 20 Nov. 2007; and Nakagawa, M. et al. (2007) Nat. Biotechnol. Advance online publication 30 Nov. 2007.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

A "ryanodine receptor" or (RyR) is a receptor that mediates the release of calcium ($Ca^{2+}$) from the sarcoplasmic reticulum. In skeletal muscle, it is believed that activation occurs via a physical coupling to the L-type calcium channel, while in cardiac muscle, the primary mechanism is calcium-induced calcium release. There are multiple isoforms of ryanodine: RyR1 primarily expressed in skeletal muscle; RyR2 primarily expressed in the myocardium; RyR3 is more widely expressed, but is especially in the brain; and and a fourth form found only in fish. These proteins have been sequenced and characterized, see for example GenBank Accession Nos. CAA01501, AAP29981, NP_001001534, NP_001095188, NP_001076231, BAA08309, AAB29457, Q92736, AAH59061, P30957, Q15413, AAI16743, NP_996757, CAA69029, and AAB58117. The gene for this protein has also been sequenced and characterized, see for example GenBank Accession Nos. NM_000540, NM_001035, NM_023868, NM_001001534, NM_177652. The above GenBank Accession Nos. were last accessed on Sep. 12, 2007.

A "Sarco/Endoplasmid Reticulum $Ca^{2+}$-ATPase" or (SERCA) is a 110-kDA transmembrane calcium pump which transfers $Ca^{2+}$ from the cytosol of the cell to the lumen of the sarcoplasmic reticulum at the expense of ATP hydrolysis during muscle relaxation. There are five isoforms of SERCA genes and the cardiac/slow skeletal muscle type splicing variant of the SERCA2a gene is the predominant SERCA isotype expressed in both normal and failing hearts. These proteins have been sequenced and characterized, see for example GenBank Accession Nos. NP_777617, NP_777615, NP_777614, NP_004311, NP_777618, NP_777613, NP_775293, CAB38029, CAA76764, BAD73969, BAD73967, AAB82290, NP_031530, NP_058025, NP_478120, AAB08097, NP_990850, NP_001672, NP_733765, and NP_001003214. The gene for this protein has also been sequenced and characterized, see for example GenBank Accession Nos. NM_001001396, NM_001684, NM_004320, and NM_174955. The above GenBank Accession Nos. were last accessed on Sep. 12, 2007.

A "$Na^+/Ca^{2+}$ exchanger" or (NCX) is a transmembrane protein and member of the cation/$Ca^{2+}$ antiporter family which plays a key role in maintaining cellular $Ca^{2+}$ homeostasis in a variety of cell types. These proteins have been sequenced and characterized, see for example GenBank Accession Nos. BAA83463, AAB50166, P70414, NP_524423, NP_732576, NP_732577, AAP37041, AAF06363, AAB46708, and NP_573484. The gene for this protein has also been sequenced and characterized, see for example GenBank Accession Nos. NM_170665, NM_001681, NM_001037102, NM_011406, NM_080440, NM_176632, and NM_012652. The above GenBank Accession Nos. were last accessed on Sep. 12, 2007.

A "cardiomyocyte or cardiac myocyte" is a specialized muscle cell which primarily forms the myocardium of the heart. Cardiamyocytes have five major components: 1. cell membrane (sarcolemma) and t-tubules, for impulse conduction, 2. sarcoplasmic reticulum, a calcium reservoir needed for contraction, 3. contractile elements, 4. mitochondria, and 5. a nucleus. Stem cells can be propagated to mimic the physiological functions of cardiomyocytes or alternatively, differentiate into cardiomyocytes. This differentiation can be detected by the use markers selected from, but not limited to, myosin heavy chain, myosin light chain, actinin, troponin, and tropomyosin.

The regulatory protein "Junctin" is a 26-kDa integral membrane protein, which forms a quaternary protein complex with the ryanodine receptor, calsequestrin and triadin at the junctional sarcoplasmic reticulum membrane in cardiac and skeletal muscles. Junctin is believed to work in conjunction with triadin as calsequestrin-anchoring proteins that couple calsequestrin to RyR and facilitate $Ca^{2+}$ release. These proteins have been sequenced and characterized, see for example GenBank Accession Nos. AAF82246, AAG16983, AAF82247, 2206415A, AAF37204, AAK00614, AAN87550, AAN87549, AAL09319, AAL09320, and AAL09321. The above GenBank Accession Nos. were last accessed on Sep. 12, 2007. The gene for this protein has also been sequenced and characterized, see for example Wetzel et al. (2000) Mol Genet. Metab. 69(3):252-258.

The regulatory protein "Triadin" is a 95 kDa integral membrane protein, which forms a quaternary protein complex with the ryanodine receptor (RyR), calsequestrin and junctin as described above. Triadin has also been shown to interact with dihydropyridine receptors (DHPR's). Triadin has been shown to co-localize with both DHPR and RyR at the junctional face of the terminal cisternae. These proteins have been sequenced and characterized, see for example GenBank Accession Nos. NP_006064, CAC44894, Q28820, NP_001076212, NP_001003154, CAD33526, AAA75315, CAI41045, CAI19636, AAC48496, AAC48497, AAC48498, AAL33878, AAL33877, and AAL33876. The gene for this protein has also been sequenced and characterized, see for example GenBank Accession Nos. NM_006073, NM_001003154, and BC139910. The above GenBank Accession Nos. were last accessed on Sep. 12, 2007.

The protein "Calsequestrin" ("CSQ") is the major calcium storage protein of the SR. Intraluminar $Ca^{2+}$ binds to calsequestrin during diastole to prevent $Ca^{2+}$ precipitation and to lower its free ionic concentration to facilitate efficient storage. Calsequestrin forms part of a large quaternary complex with the ryanodine receptor, triadin, and junctin as described above. These proteins have been sequenced and characterized, see for example GenBank Accession Nos. NP_001222, NP_001223, BAA23494, CAI23373, CAI14532, CAI15276, EAW52736, AAH22289, AAA48674, CAA45609, NP_001095161, AAB87570, AAC69472, AAI05186, BAF34916, and AAI33410. The gene for this protein has also been sequenced and characterized, see for example GenBank Accession Nos. NM_001232 and NM_001231. The above GenBank Accession Nos. were last accessed on Sep. 12, 2007.

The protein "Phospholamban" is a 52 amino acid integral membrane protein that regulates the $Ca^{2+}$ pump in cardiac muscle cells. Dephosphorylated phospholamban interacts with the $Ca^{2+}$ ATPase pump SERCA to lower its activity and sensitivity to $Ca^{+2}$, thus decreasing $Ca^{2+}$ uptake into the sarcoplasmic reticulum. Thus, when phospholamban is phosphorylated, its interact with SERCA is reduced, resulting in an increase in $Ca^{2+}$ transport into the sarcoplasmic reticulum. This protein has been sequenced and characterized, see for example GenBank Accession Nos. NP_002658, NP_073198, NP_075618, NP_001003332, NP_999378, NP_001076090, NP_990741, and P61012. The gene for this protein has also been sequenced and characterized, see for example GenBank Accession Nos. NM_214213, NM_002667, NM_023129 and NM_001003332. The above GenBank Accession Nos. were last accessed on Sep. 12, 2007.

The cardiomyocyte marker "myosin heavy chain" and "myosin light chain" are part of a large family of motor proteins found in muscle cells responsible for producing contractile force. These proteins have been sequenced and characterized, see for example GenBank Accession Nos. AAD29948, CAC70714, CAC70712, CAA29119, P12883, NP_000248, P13533, CAA37068, ABR18779, AAA59895, AAA59891, AAA59855, AAB91993, AAH31006, NP_000423, and ABC84220. The genes for these proteins has also been sequenced and characterized, see for example GenBank Accession Nos. NM_002472 and NM_000432. The above GenBank Accession Nos. were last accessed on Sep. 12, 2007.

The cardiomyocyte marker "actinin" is a mircrofilament protein which are the thinnest filaments of the cytoskeleton found in the cytoplasm of all eukaryotic cells. Actin polymers also play a role in actomyosin-driven contractile processes and serve as platforms for myosin's ATP hydrolysis-dependent pulling action in muscle contraction. This protein has been sequenced and characterized, see for example GenBank Accession Nos. NP_001093, NP_001095, NP_001094, NP_004915, P35609, NP_598917, NP_112267, AAI07534, and NP_001029807. The gene for this protein has also been sequenced and characterized, see for example GenBank Accession Nos. NM_001102, NM_004924, and NM_001103. The above GenBank Accession Nos. were last accessed on Sep. 12, 2007.

The cardiomyocyte marker "troponin" is a complex of three proteins that is intergral to muscle contraction in skeletal and cardiac muscle. Troponin is attached to the protein "tropomyosin" and lies within the groove between actin filaments in muscle tissue. Tropomyosin can be used as a cardiomyocite marker. These proteins have been sequenced and characterized, see for example GenBank Accession Nos. NP_000354, NP_003272, P19429, NP_001001430, AAB59509, AAA36771, and NP_001018007. The gene for this protein has also been sequenced and characterized, see for example GenBank Accession Nos. NM_000363, NM_152263, and NM_001018007. The above GenBank Accession Nos. were last accessed on Sep. 12, 2007.

The protein "caveolin 3" is a 151 amino acid (~20-kDA) protein shown to be associated with the caveolar plasma membranes and is a muscle specific form of the caveolin family. Caveolins in general are believed to act as scaffolding proteins within caveolar membranes. This protein has been sequenced and characterized, see for example GenBank Accession Nos. NP_203123, NP_001225, P56539, NP_062028, NP_031643, and Q2KI43. The gene for this protein has also been sequenced and characterized, see for example GenBank Accession Nos. NM_019155 and Z18951. The above GenBank Accession Nos. were last accessed on Sep. 12, 2007.

The protein "amphiphysin 2"(also known as Bin1) have a putative role in membrane deformation at endocytic sites. An isoform of amphiphysin 2 concentrated at t-tubules induces tubular plasma membrane invaginations when expressed in nonmuscle cells. In developing myotubes, amphiphysin 2 and caveolin 3 segregate in tubular and vesicular portions of the t-tubules system, respectively. These proteins have been sequenced and characterized, see for example GenBank Accession Nos. NP_647477, CAA57197, P49418, NP_778172, and CAA73807. The gene for this protein has also been sequenced and characterized, see for example GenBank Accession Nos. NM_009668, NM_139343, NM_139344, NM_139346, NM_139347, NM_139349, NM_139345, NM_139348, NM_004305, NM_139350, and NM_139351. The above GenBank Accession Nos. were last accessed on Sep. 12, 2007.

In one aspect, an "electrophysiological phenotype" of a cell or tissue is the measurement of a cell or tissue's action potential. An action potential is a spike of electrical discharge that travels along the membrane of a cell. The properties of action potentials differ depending on the cell type or tissue. For example, cardiac action potentials are significantly different from the action potentials of most neuronal cells. In one embodiment, the action potential is a cardiac action potential. The "cardiac action potential" is a specialized action potential in the heart, with unique properties necessary for function of the electrical conduction system of the heart. The cardiac action potential has 5 phases; phase 4 (resting membrane potential), phase 0 (rapid depolarization), phase 1 (inactivation of the fast $Na^+$ channels causing a small downward deflection of the action potential), phase 2 (a.k.a. the plateau phase, is the sustained balance between inward movement of $Ca^{2+}$ and outward movement of $K^+$), phase 3 (cell repolarization), and back to phase 4. The cardiac action potentials of cells comprising the different portions of the heart have unique features and patterns specific to those cells including, atrial, ventricular, and pacemaker action potentials. This action potential is a unique property of SA nodal cells and most importantly the spontaneous depolarization (a.k.a. automaticity) necessary for SA node's pacemaker activity. The normal activity of SA nodal cells of the heart is to spontaneously depolarize at regular rhythm, thus generating a normal heart rate. Another embodiment of the invention is the electrophysiological phenotype of an adult cardiac ventricular or atrial muscle cell that have normally electrically silent-yet-excitable properties.

"$I_{K1}$ activity" is the activity of a cell which results in the inward rectifier current of the cell. It is contemplated that the $I_{K1}$ activity is a stabilizer of a cell's resting membrane potential. This activity is controlled by a family of proteins termed the inward-rectifier potassium ion channels (Kir channels). There are seven subfamilies of Kir channels (Kir1, Kir2, Kir3, Kir4, Kir5, Kir6, and Kir7). Each subfamily has multiple members (e.g. Kir2.1, Kir2.2, Kir2.3, etc). The Kir2 subclass has four members, Kir2.1, Kir2.2, Kir2.3, and Kir2.4. The active Kir channels are formed from homotetrameric membrane proteins. Additionally, heterotetramers can form between members of the same subfamily (e.g. Kir2.1 and Kir2.3) when the channels are overexpressed. The proteins Kir2.1, Kir2.2, Kir2.3, and Kir2.4 are also know as IRK1, IRK2, IRK3, and IRK4, respectively. These proteins have been sequenced and characterized, see for example GenBank Accession Nos. AAF73241, AAF73242, BAC02718, NP_000882, BAD23901, NP_066292, AAL89708, P63252, P52185, P52190, O19182, O18839, Q64273, P49656, P35561, CAA56622, AAY53910, Q14500, P52188, P52187, NP_001019861, NP_690607, NP_609903, Q64198, P52189, NP_004972, AAF97619, NP_733838, Q8JZN3 and O70596, last accessed on Sep. 28, 2007. The genes for these proteins have been sequenced and characterized, see for example GenBank Accession Nos. AB074970, AF153819, NM_000891, AB182123, NM_021012, AF482710, X80417, DQ023214, NM_001024690, NM_152868, NM_004981, AF181988, and NM_170720, last accessed on Sep. 28, 2007.

"$I_f$ activity" is the activity of a cell which results in the "funny" or pacemaker current of the cell. It is contemplated that this current functionally modulates pacing of cells which compose the heart (specifically the cells which compose the SA node). The $I_f$ activity is a mixed $Na^+/K^+$ inward current activated by hyperpolarization and modulated by the autonomic nervous system.

Atrial Natriuretic Factor (ANF) is a short (approximately 28 amino acids) peptide that is produced, stored and released by cardiac myocytes of the atria of the heart. It is released in response to atrial stretch and a variety of other signals. The amino acid and putative gene for an ANF precursor is known in the art, for example at GenBank Accession No. X01471, last accessed on Sep. 10, 2008. A synthetic ANF gene and its translation product is reported at GenBank Accession No. X08077, last accessed on Sep. 10, 2008.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker, e.g. myosin or actin or the expression of a gene or protein, e.g. a calcium handling protein, a t-tubule protein or alternatively, a calcium pump protein. In another aspects, the substantially homogenous population have a decreased (e.g., less than about 95%, or alternatively less than about 90%, or alternatively less than about 80%, or alternatively less than about 75%, or alternatively less than about 70%, or alternatively less than about 65%, or alternatively less than about 60%, or alternatively less than about 55%, or alternatively less than about 50%) of the normal level of expression than the wild-type counterpart cell or tissue.

A "biocompatible scaffold" refers to a scaffold or matrix for tissue-engineering purposes with the ability to perform as a substrate that will support the appropriate cellular activity to generate the desired tissue, including the facilitation of molecular and mechanical signaling systems, without eliciting any undesirable effect in those cells or inducing any undesirable local or systemic responses in the eventual host. In other embodiments, a biocompatible scaffold is a precursor to an implantable devise which has the ability to perform its intended function, with the desired degree of incorporation in the host, without eliciting an undesirable local or systemic effects in the host. Biocompatible scaffolds are described in U.S. Pat. No. 6,638,369.

A "composition" is intended to mean a combination of active agent, cell or population of cells and another compound or composition, inert (for example, a detectable agent or label) or active, such as a biocompatible scaffold.

A "pharmaceutical composition" is intended to include the combination of an active agent with a carrier, inert or active such as a biocompatible scaffold, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, Remington's Pharm. Sci., 15th Ed. (Mack Publ. Co., Easton (1975)).

An "effective amount" is an amount sufficient to effect beneficial or desired results. An effective amount can be administered in one or more administrations, applications or dosages.

A "subject," "individual" or "patient" is used interchangeably herein, and refers to a vertebrate, preferably a mammal, more preferably a human. Mammals include, but are not limited to, murines, rats, simians, bovines, canines, humans, farm animals, sport animals and pets.

A "cell" is intended to include any individual cell or cell culture which can be or have been recipients for vectors or the incorporation of exogenous polynucleotides, polypeptides and/or proteins or compounds or compositions that upregulate, down-regulate, turn-on or turn-off the expression of a gene or protein. Unmodified cells are referred to as "source cells" or "source stem cells". The cells may be prokaryotic or eukaryotic, and include but are not limited to bacterial cells, yeast cells, plant cells, insect cells, animal cells, and mammalian cells, e.g., murines, rats, simians, bovines, canines and humans.

A "control" is an alternative subject or sample used in an experiment for comparison purpose. A control can be "positive" or "negative". For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype).

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., cardia arrythmia. As is understood by those skilled in the art, "treatment" can include systemic amelioration of the symptoms associated with the pathology and/or a delay in onset of symptoms such as chest pain. Clinical and sub-clinical evidence of "treatment" will vary with the pathology, the individual and the treatment.

Embodiments
Modified Cells and Populations of Cells

One embodiment of the invention is an isolated stem cell that has been modified to provide electrically active cells having the functions of a mature sarcoplasmic reticulum (SR). Functionally mature SR will result in the isolated stem cell possessing $Ca^{2+}$ handling properties more similar to mature or adult cardiomyocytes. Examples of stem cells that can be modified include, but are not limited to embryonic stem cells, progenitor cells and adult stem cells that posses the ability to further differentiate into cells of a desired lineage. The cells can be isolated from a host or can be obtained from an established cell culture. Methods to isolate and culture ESC are known in the art and described in Xue et al. (2005) Circulation 111:11-20, Thomson et al. (1998) Science 282: 1145-1147, Moore et al. (2005) Reproductive Toxicology 20:377-391, and Wang et al. (2005) Stem Cells 23:1526-1534. Available sources of these cells include, for example, from the NIH Human Embryonic Stem Cell Registry.

The cells can be from any suitable source, e.g., an animal or vertebrate. Non-limiting examples include murine, rat, porcine, canine, simian and human.

Functional SR is obtained by modifying the genotype and/or phenotype of the stem cell. In one aspect, the stem cell or its derivative is modified by expressing one or more of a calcium channel protein that is necessary to perform physiological functions of mature cardiomyocytes. Examples of calcium channel proteins include, but are not limited to ryanodine receptor (RyR) protein. In another aspect, the stem cell is modified to express a calcium handling protein. Examples of calcium handling proteins include, but are not limited to calsequestrin, junctin, triadin, and phospholamban.

Functional SR can also be obtained by modifying the stem cell to express a calcium pump protein such as a sarco/endoplasmic reticulum $Ca^{2+}$-ATPase (SERCA) protein. The expression of either one or both of the calcium channel and calcium pump proteins will result in a cell providing functionally mature SR.

In another aspect, functional SR is provided by reducing expression of the $Na^+/Ca^{2+}$ exchanger (NCX) protein in the stem cell. A reduction in the expression of this protein results in a functionally mature SR by modifying the ratio of NCX to other calcium channel or pump proteins similar to those found in mature cardiomyocytes.

SR functions can be obtained or enhanced by modifying the stem cell or its derivative to enhance expression of a membrane structure transverse (t)-tubule biogenic protein(s). Examples of such include, but are not limited to caveolin 3 and amphiphysin 2.

In a yet further aspect, t-tubule formation can be promoted by other means such as, but not limited to, physical, electrical and/or mechanical stimulations.

This invention also provides a stem cell that has been modified as described above, wherein the cell further expresses a cardiomyocyte cell marker selected from, but not limited to, myosin heavy chain, myosin light chain, actinin, troponin and tropomyosin. Other markers that can be used are cell surface markers, which are well known to those skilled in the art.

This invention also provides a substantially homogeneous population of stem cells that have been modified as described above. One embodiment of the invention is a substantially homogeneous population of stem cells that expresses a calcium channel protein such as a ryanodine receptor (RyR) protein. Another embodiment of the invention is a substantially homogeneous population of stem cells that expresses a calcium pump protein such as a sarco/endoplasmic reticulum $Ca^{2+}$-ATPase (SERCA) protein. A further embodiment of the invention is a substantially homogeneous population of stem cells that comprises a reduced expression of the $Na^+/Ca^{2+}$ exchanger (NCX) protein. A yet further embodiment of the invention is a substantially homogeneous population of stem cells that have been modified to contain a functional SR or enhanced expression of a calcium channel protein and further expresses a calcium handling protein selected from, but not limited to, calsequestrin, junctin, triadin, and phospholamban. Another embodiment of the invention is a substantially homogeneous population of stem cells that have been modified to contain a functional SR or enhanced expression of a calcium channel protein and further contains the membrane structure transverse (t)-tubule. An alternate embodiment of the invention is a substantially homogeneous population of stem cells that have been modified to contain a functional SR or enhanced expression of a calcium channel protein and further expresses a t-tubule biogenic protein that is, but not limited to caveolin 3 or amphiphysin 2.

In another aspect, the substantially homogeneous population of stem cells contain a modified genotype or phenotype as described above and further express a cardiomyocyte marker selected from, but not limited to, myosin heavy chain, myosin light chain, actinin, troponin and tropomyosin.

In one aspect of the invention including all of the above embodiments, the substantially homogeneous population of stem cells are comprised of embryonic stem cells or pluipotent stem cells. In another aspect of the invention including all of the above embodiments, the substantially homogeneous population of stem cells are comprised of mammalian cells. In a further embodiment, the mammalian cells are human cells. Compositions and methods to differentiate stem cells to cardiac cells are known in the art, e.g., U.S. Pat. No. 6,387,369 and U.S. Patent Publication No. 2007/0025972A1.

Yet another embodiment of the invention is a composition of a substantially homogeneous population of stem cells that have been propagated to contain a functional SR or enhanced expression of a calcium channel protein and a carrier. In another further embodiment, the carrier is, but not limited to, a biocompatible scaffold or a pharmaceutically acceptable carrier. In a further aspect, a composition containing cells differentiated from the modified stem cells are provided in combination with a carrier.

Further provided by this invention are any one or more combinations of the above-noted independent modifications. Thus, Applicant's invention includes any one or more combination of the independently described modifications. The preferred modification or combination of modifications will be determined by the use of the modified cells and in some aspects, the patient to be treated with the modified cell or population of cells.

Also provided by this invention is a population of differentiated cells produced by propagating the above-noted isolated cell(s) or substantially homogeneous population of cells. In one aspect, the cells and/or populations are propagated under conditions that produce immature or mature cardiomyocytes. These methods are known to those skilled in the art and are described, for example in Xue et al. (2005) Circulation 111:11-20, Moore et al. (2005) Reproductive Toxicology 20:377-391, and Wang et al. (2005) Stem Cells 23:1526-1534. In another aspect, they are propagated under conditions that produce clonal populations of substantially identical or identical cells.

Methods to Produce Modified Cells and Populations of Cells

Also provided by this invention are methods to produce the isolated modified stem cells as described herein. The methods require the genetic modification of the source stem cell by modulation of the expression of one or more genes described above. In one aspect, such modification is achieved by inserting a polynucleotide encoding the gene into the source cell by any suitable method. For example, the polynucleotide of interest is inserted into a vector such as a viral vector which is then contacted with the cell under conditions that facilitate transfer of the vector and polynucleotide into the cell. The recipient cell is grown or propagated under suitable conditions to express the inserted gene. In other aspects, the cell is modified to enhance expression of the endogenous gene of interest. In further aspects, the genes are overexpressed as compared to a wild-type counterpart cell by inserting numerous copies of the polynucleotide or alternatively, enhancing expression of the endogenous gene of interest. In the embodiment where the modification is reduced expression, for example the reduced expression of the NCX protein, compositions and methods to reduce or block endogenous expression are utilized.

Applicant has provided herein the protein and/or polynucleotide sequences for use in gene transfer and expression techniques described below. It should be understood, although not always explicitly stated that the sequences provided herein can be used to provide the expression product as well as substantially identical sequences that produce a protein that has the same biological produce. These "biologically equivalent" polypeptides can hybridize under moderate or stringent conditions to the sequences provided herein or the complement. They also are at least 80%, or alternatively at least 85%, or alternatively at least 90%, or alternatively at least 95% or alternatively at least 98%, identical to the reference polynucleotide when compared using sequence identify methods run under default conditions.

Gene Expression and Nucleic Acids

In order to express the proteins described herein, delivery of nucleic acid sequences encoding the gene on interest can be delivered by several techniques. Examples of which include viral technologies (e.g. retroviral vectors, adenovirus vectors, adeno-associated virus vectors, alphavirus vectors and the like) and non-viral technologies (e.g. DNA/liposome complexes, and targeted viral protein-DNA complexes). Once inside the cell of interest, expression of the transgene can be under the control of ubiquitous promoters (e.g. EF-1α) or tissue specific promoters (e.g. the muscle specific promoter α-actin). Alternatively expression levels may controlled by use of an inducible promoter system (e.g. Tet on/off promoter). The genes described herein include RyR, SERCA, NCX, calsequestrin, junctin, triadin, phospholamban, caveolin 3, and amphiphysin 2. GenBank accession nos. for the above are describe above.

This invention also provides genetically modified cells that produce enhanced expression of the genes of described herein or their equivalents. The genetically modified cells can be produced by insertion of upstream regulatory sequences such as promoters or gene activators (see, U.S. Pat. No. 5,733,761).

Non-limiting examples of promoters include, but are not limited to, the cytomegalovirus (CMV) promoter (Kaplitt et al. (1994) Nat. Genet. 8:148-154), CMV/human β3-globin promoter (Mandel et al. (1998) J. Neurosci. 18:4271-4284), GFAP promoter (Xu et al. (2001) Gene Ther., 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277) and the β-glucuronidase (GUSB) promoter (Shipley et al. (1991) Genetics 10:1009-1018), the human serum albumin promoter, the alpha-1-antitrypsin promoter. To improve expression, other regulatory elements may additionally be operably linked to the transgene, such as, e.g., the Woodchuck Hepatitis Virus Post-Regulatory Element (WPRE) (Donello et al. (1998) J. Virol. 72: 5085-5092) or the bovine growth hormone (BGH) polyadenylation site.

Additional promoters which are suitable for the present invention may be any strong constitutive or tissue (cardiac)-specific promoter which is capable of promoting expression of an associated coding DNA sequence in cardiac muscle or cardiomyocytes. Such strong constitutive promoters include the human and murine cytomegalovirus promoter, truncated CMV promoters, human serum albumin promoter [HSA], the alpha-1-antitrypsin promoter and myosin light chain promoter.

In addition to the expression of genes described herein, the down regulation of presently existing genes within the cell can be utilized. "Reducing expression" or "down regulating expression" is a process resulting in the decreased gene and corresponding protein expression. For example, when a cell is overly stimulated by a neurotransmitter, hormone or drug for a prolonged period of time and the expression of the receptor protein is decreased in order to protect the cell. Reducing expression of a gene described herein can be done by a variety of method known in the art. Examples of which include the use of oligonucleotide-based strategies including interfering RNA technology, micro-RNA, siRNA, and vector based technologies including insertional mutagenesis, Cre-Lox deletion technology, double-stranded nucleic acid RNA/RNA, DNA/DNA, RNA/DNA and the like.

Polynucleotides useful for the methods of this invention can be replicated using PCR. PCR technology is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein.

Detection

One can determine if the required expression, overexpression or underexpression of the polynucleotide of interest has been achieved by using methods known in the art, e.g., by traditional hydridization techniques, immunohistochemistry or PCR. Specific examples include hybridization to DNA microarrays, in situ hybridization, PCR, RNase protection assays and Northern blot analysis. Alternatively expression of the encoded polypeptide can be detected using antibodies that specifically recognize and bind the polypeptide or protein. Such antibodies are useful for visualizing cells that express the polypeptide using techniques such as immunohistology, ELISA, and Western blotting.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

One can also determine if the modified cell has functional SR activity by testing the action potential, electrical activity and/or $Ca^{2+}$ handling of the modified cell. These physiological methods include but are not limited to a spectrofluorometric method such as fura and indo ratiometric calcium indicators or using mechanical measurement of electrical fields. These methods are described in the patent and technical literature for example, U.S. Pat. No. 7,084,641 and Grynkiewicz et al. (1985) J. Biol. Chem. 260(6):3440-3450.

Compositions

This invention also provides compositions containing the cells, population of cells and/or differentiated cells in combination with a carrier, such as a biocompatible scaffold or a pharmaceutically acceptable carrier. In one embodiment, the composition is intended for therapeutic use and therefore, an effective amount of the modified cell, population of cells or differentiated cells are provided in the composition.

Uses of the Cells and Cell Populations

Yet another embodiment of the invention is a method for restoring cardiac function in a tissue or host in need thereof. This and other therapeutic uses are described herein.

In one embodiment, the invention provides methods for regenerating cardiac muscle tissue by growing an effective amount of the modified cell or population of cells described above. Yet another embodiment of the invention is a method for regenerating cardiac muscle tissue by growing an effective amount of a substantially homogeneous population of stem cells described above. After culturing of the cells, an effective amount of the cells and/or populations comprising the cells can be transplanted into a host in need thereof to restore cardiac function in the host.

Yet another embodiment of the invention is a method for regenerating cardiac muscle tissue in a suitable host by administering to the host an effective amount of the isolated stem cell or population of cells as described above.

A further embodiment of the invention is the host is a mammalian patient and the isolated stem cell is mammalian. In another embodiment, the host is a human patient and the isolated stem cell is human. In another embodiment, the stem cells and/or substantially homogeneous population of stem cells can be transplanted or administered into a tissue to populate or differentiate into cardiomyocytes of the host.

Another embodiment of the invention is a method for regenerating cardiac muscle tissue in a suitable host by administering to the host an effective amount of a substantially homogeneous population of stem cells that have been propagated to contain a functionally mature SR or enhanced expression of a calcium channel protein. In a further embodiment the host is a mammalian patient and the isolated stem cell is mammalian. In another embodiment, the host is a human patient and the isolated stem cell is human.

Another embodiment of the invention is a method for differentiating an isolated stem cell to have a functionally mature SR by enhancing the expression of a calcium handling protein selected from, but not limited to, calsequestrin, junctin, triadin, or phospholamban.

Another embodiment of the invention is a method for differentiating an isolated stem cell to have a mature SR function by enhancing the expression of a transverse (t)-tubule biogenic protein selected from, but not limited to, caveolin 3 or amphiphysin 2.

Another embodiment of the invention is a method for differentiating an isolated embryonic stem cell to have a functionally mature SR by enhancing the expression of both a calcium handling protein and a transverse (t)-tubule biogenic protein selected from, but not limited to, calsequestrin, junctin, triadin, or phospholamban and caveolin 3 or amphiphysin 2, respectively.

Another embodiment of the invention is a method of improving cardiac function in a patient in need thereof by the administration of an effective amount of the isolated stem cell that has been propagated to mature the functions of the SR or enhanced expression of a calcium channel protein. The patients of this embodiment are suffering from a disease or disorder associated with cardiac malfunction including, but not limited to, sick sinus syndrome, congestive heart failure, isolated diastolic heart failure, myocardial infarction, and cardiac arrhythmia. There are several forms of cardiac arrhythmia that can be treated including, but not limited to, bradyarrhythmia, abnormal sinus node function, atrioventricular block, and atrial and ventricular tachyarrhythmia.

Another embodiment of the invention is a method of improving cardiac function in a patient in need thereof by the administration of an effective amount of substantially homogeneous population of stem cells that has been propagated to mature the functions of the SR or enhanced expression of a calcium channel protein. The patients of this embodiment are suffering from a disease or disorder associated with cardiac malfunction including, but not limited to, sick sinus syndrome, congestive heart failure, isolated diastolic heart failure, myocardial infarction, and cardiac arrhythmia. There are several forms of cardiac arrhythmia that can be treated including, but not limited to, bradyarrhythmia, abnormal sinus node function, atrioventricular block, atrial and ventricular tachyarrhythmia.

Administration of the cells or compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art.

The cells and populations of cell are administered to the host using methods known in the art and described, for example, in U.S. Pat. No. 6,638,369.

Screening Assays

The present invention provides methods for screening various agents that modulate the expression of a polynucleotide of the invention or the function of a protein product encoded by the polynucleotide of interest in a cell. For the purposes of this invention, an "agent" is intended to include, but not be limited to a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

One aspect of the invention is a method for screening small molecules capable of interacting with the protein or polynucleotide of the invention. For the purpose of this invention, "small molecules" are molecules having low molecular weights (MW) that are, in one embodiment, capable of binding to a protein of interest thereby altering the function of the protein. Preferably, the MW of a small molecule is no more than 1,000. Methods for screening small molecules capable of altering protein and/or polynucleotide function are known in the art. For example, a miniaturized arrayed assay for detecting small molecule-protein interactions in cells is discussed by You et al. (1997) Chem. Biol. 4:961-968.

To practice the screening method in vitro, suitable cell cultures or tissue cultures containing the modified cell(s) are first provided. When the agent is a composition other than a DNA or RNA, such as a small molecule as described above, the agent can be directly added to the cell culture or added to culture medium for addition. As is apparent to those skilled in the art, an "effective" amount must be added which can be empirically determined. When agent is a polynucleotide, it can be directly added by use of a gene gun or electroporation. Alternatively, it can be inserted into the cell using a gene delivery vehicle or other method as described above. Positive and negative controls can be assayed to confirm the purported activity of the drug or other agent.

In another aspect, this invention provides a method of identifying an agent that modulates the transport of calcium ($Ca^{2+}$) ions to and/or from the sarcoplasmic reticulum (SR) in a cell comprising contacting the cell with an amount of a test agent under conditions effective to modulate the SR's ability to store or pump $Ca^{2+}$ ions, measuring a change in $Ca^{2+}$ transients wherein a change in a measureable feature of the $Ca^{2+}$ transients such as, but not limited to, basal $Ca^{2+}$ levels, amplitude, Vmax upstroke or Vmax decay identifies the test agent as an agent that modulated the transport of $Ca^{2+}$ ions from the SR in a cell. In a further aspect, the transport of calcium ($Ca^{2+}$) ions comprises $Ca^{2+}$ induced $Ca^{2+}$ release (CICR). In yet a further aspect, the change in $Ca^{2+}$ transients indicates toxicity of the test agent to the cell, which include, but are not limited to, cardiotoxicity or arrhythmogenicity.

In one embodiment of the invention, the cell useful for this method is an isolated stem cell, substantially homogeneous population of stem cells or derivatives of each thereof, or a composition described herein modified to provide functions of the sarcoplasmic reticulum (SR). In another aspect the isolated stem cell, substantially homogeneous population of stem cells or derivatives thereof or composition as described herein expresses a calcium channel protein that is necessary to perform physiological functions. In a further aspect, the calcium channel protein is a ryanodine receptor (RyR) protein. In another aspect, the isolated stem cell, substantially homogeneous population of stem cells or composition described herein further expresses a calcium pump protein that is necessary to perform physiological functions. In a further aspect, the calcium pump protein is a sarco/endoplasmic reticulum $Ca^{2+}$-ATPase (SERCA) protein. In yet another aspect, the isolated stem cell, substantially homogeneous population of stem cells or composition described herein further comprises reduced expression of the $Na^+/Ca^{2+}$ exchanger (NCX) protein. In yet another aspect, the isolated stem cell, substantially homogeneous population of stem cells or derivative thereof or composition described herein further expresses a calcium handling protein, wherein the protein is selected from the group consisting of calsequestrin, junctin, triadin and phospholamban. In yet another aspect, the isolated stem cell, substantially homogeneous population of stem cells or composition described herein further comprises the membrane structure transverse (t)-tubule. In yet another aspect, the isolated stem cell, substantially homogeneous population of stem cells or composition described herein further expresses a transverse (t)-tubules biogenic protein that is caveolin 3 or amphiphysin 2.

In another embodiment of the invention, the isolated stem cell, substantially homogeneous population of stem cells or composition described herein expresses a cardiomyocyte marker selected from the group consisting of myosin heavy chain, myosin light chain, actinin, troponin and tropomyosin. In one aspect the isolated stem cell, substantially homogeneous population of stem cells or composition described herein is an embryonic stem cell or a pluripotent stem cell. In one aspect, the cell can be a mammalian cell. In a further aspect, the mammalian cell is a human cell.

The following examples are intended to illustrate and not limit the inventions as provided herein.

EXAMPLE 1

By way of background, it is known that the primary function of our heart is to mechanically pump blood throughout the body. However, cardiomyocytes (CMs) are non-regenerative. As a result, transplantation is the last resort for end-stage heart failure patients but this is hampered by the severe shortage of donor organs (1-2). Human (h) embryonic stem cells (ESC), derived from the inner cell mass of human blastocysts, can self-renew while maintaining their pluripotency (3). Upon in vitro induction, hESCs can differentiate into spontaneously beating CMs (4-8). Indeed, hESC-derived CMs (hESC-CMs) display structural and functional properties of early-stage cardiomyocytes, (7) and can functionally integrate with (4, 9) or even electrically pace the recipient heart after transplantation in vivo (4).

During an action potential of adult CMs, $Ca^{2+}$ entry into the cytosol through sarcolemmal L-type $Ca^{2+}$ channels triggers the release of $Ca^{2+}$ from the intracellular $Ca^{2+}$ stores (a.k.a. sarcoplasmic reticulum or SR) via the ryanodine receptor (RyR). This process, the so-called $Ca^{2+}$-induced $Ca^{2+}$ release (CICR), (10) escalates the intracellular $Ca^{2+}$ ($[Ca^{2+}]_i$) to activate the contractile apparatus for contraction. For relaxation, elevated $[Ca^{2+}]_i$ is pumped back into the SR by the sarco/endoplasmic reticulum $Ca^{2+}$-ATPase (SERCA) and extruded by the $Na^+$—$Ca^{2+}$ exchanger (NCX) to return to the resting $[Ca^{2+}]_i$ level. Such a rise and subsequent decay of $[Ca^{2+}]_i$ is known as $Ca^{2+}$ transient (11). Given the central importance of CICR in cardiac excitation-contraction (EC) coupling, proper $Ca^{2+}$ handling properties of hESC-CMs are therefore crucial for their successful functional integration with the recipient heart after transplantation. Indeed, abnormal $Ca^{2+}$ handling, as in the case of heart failure, can even be arrhythmogenic (e.g. delayed after depolarization) (10, 12).

In mouse (m) ESC-CMs, both the SR load and RyR are essential for regulating contractions even at very early developmental stages (13). By contrast, it has been reported that spontaneously beating hESC-CMs (derived from the H9.2 and 13 hESC lines) do not have functional SRs and that their contractions result from trans-sarcolemmal $Ca^{2+}$ influx rather than $Ca^{2+}$ release from the SR (14). To better define the poorly known $Ca^{2+}$ handling properties of hESC-CMs, experiments performed herein are a comprehensive analysis of $Ca^{2+}$ transients recorded from CMs differentiated from the H1 (H1-CMs) and HES2 (HES2-CMs) hESC lines and compared their properties to those of human fetal left ventricular CMs (FLV-CMs, 16-18 weeks) under different electrophysiological and pharmacological conditions. Human FLV-CMs, which have been suggested as a choice for myocardial repair, (15) were chosen for comparison because they are developing yet functional CMs. Furthermore, the electrical phenotypes of hESC-CMs have been reported to exhibit fetal-like properties, (5,6) but a detailed comparison of their $Ca^{2+}$ handling properties has not been performed. Experimental evidence shows that both H1- and HES2-CMs do express functional SRs. A better understanding of these fundamental properties of hESC-CMs is crucial for designing effective strategies or protocols for improving both their safety and functional efficacy (e.g. facilitated or driven maturation of $Ca^{2+}$ handling properties for enhanced contractile functions).

hESC Culturing and Differentiation

The HES2 (ESI, Singapore) and H1 (WiCells, Madison, Wis.) hESC lines (NIH codes are ES02 and WA01, respectively) chosen for this study were cultured and differentiated as previously described (4, 16, 17).

Briefly, HES2 cells were grown on mitomycin C- (Sigma; St Louis, Mo., USA) inactivated mouse embryonic fibroblasts (mEFs). Culture medium consisted of DMEM (Invitrogen, Carlsbad, Calif.) containing 2 mM L-glutamine, insulin-transferrin-selenium, non-essential amino acids, 90 μM β-mercaptoethanol, and 20% FBS (Hyclone, Logan, Utah). HES2 cells were passaged manually ("cut-and-paste"), by cutting colony into pieces and removing them from the mEFs using dispase (8 mg/mL, Invitrogen, Carlsbad, Calif.). For cardiac differentiation, HES2 cells were removed from the mEFs, resuspended and broken into pieces, followed by co-culturing with the immortalized endoderm-like END2 cells at 100% confluence (6).

H1 cells were grown on irradiated mEFs from 13.5-day embryos of CF-1 mice and propagated as previously described (3). The culture medium consisted of 80% Dulbecco's modified Eagle's medium, 20% knockout serum replacement, 4 ng/ml basic fibroblast growth factor, 1 mmol/L glutamine, 0.1 mmol/L β-mercaptoethanol, and 1% nonessential amino acid solution (all from Gibco-BRL, Gaithersburg, Md.). To induce the formation of embryoid bodies (EBs), hESCs were detached using 1 mg/mL type IV collagenase (Gibco-BRL) and transferred to Petri dishes containing 80% Dulbecco's modified Eagle's medium, 20% fetal bovine serum defined (HyClone, Logan, Utah), 1 mmol/L glutamine, and 1% nonessential amino acid stock in the absence of β-FGF. The aggregates were cultured in suspension for 7 days, followed by plating on gelatin-coated (0.1%; Sigma-Aldrich, St. Louis) 6-well plates to form hESC-CMs.

Isolation of hESC-CMs

For isolating hESC-CMs, beating outgrowths were microsurgically dissected from H1- (7+11 to 17 or 18-24 days) and HES2- (18-24 days) derived EBs by a glass knife, (4) followed by incubation in collagenase II (1 mg/mL) at 37° C. for 30 min. The isolated cells were incubated with KB solution containing (mM): 85 KCl, 30 $K_2HPO_4$, 5 $MgSO_4$, 1 EGTA, 2 $Na_2$-ATP, 5 pyruvic acid, 5 creatine, 20 taurine, 20 d-glucose, at room temperature for 30 min. After the cells were plated on laminin-coated glass coverslips for 1 hr at 37° C., regular culture media was added. Same as previous reports, (6, 18) sarcomeres were displayed in these derived CMs as shown after myosin heavy chain, α-actinin and tropomyosin staining although much less evident and defined than those in adult CMs. Calcium recordings from cell clusters containing 10-15 cells were performed within 48 hrs after plating.

Isolation of Human Fetal and Adult Left Ventricular Cardiomyocytes

Human FLV-CMs and adult-CMs were isolated and experimented according to protocols approved by the UC Davis IUPAC and IRB (Protocol #200614787-1 and # 200614594-1). Briefly, fetal human hearts (16-18 weeks, Advanced Bioscience Resources, INC. Alameda, Calif.) and adult human hearts (18+ years, National Disease Research Interchange, Philadelphia, Pa.) were perfused with enzymatic solutions using a customized Langendorff apparatus as previously described (19). FLV-CMs were cultured on laminin-coated glass coverslips in 24-well dishes with a density of ~5×10$^5$ cells/well in a water-jacket incubator at 37° C. with media containing: 5 mM carnitine, 5 mM creatine, 5 mM taurine, 100 µg ml$^{-1}$ penicillin-streptomyocin and 10% fetal bovine serum in Medium 199 (Sigma-Aldrich Corp. St. Louis, Mo.). Adult-CMs were stored at −80° C. for Western blotting.

Measurements of Cytosolic $Ca^{2+}$

A spectrofluorometric method with Fura-2/AM as the $Ca^{2+}$ indicator was used for measuring $[Ca^{2+}]_i$. FLV- or hESC-CMs were incubated with 5 µM Fura-2/AM and 0.2% pluronic F-127 for 30 min at 37° C. Fluorescent signals obtained upon excitation at 340 nm (F340) and 380 nm (F380) were recorded from cells perfused with Tyrode solution containing (mM): 140 NaCl, 5.0 KCl, 1.0 $CaCl_2$, 1.0 $MaCl_2$, 10.0 glucose and 10 HEPES (pH 7.4) unless otherwise indicated. Data were analyzed using the Ionwizard software (Version 5, IonOptix) to generate the Ca transient parameters reported in this study. The F340/F380 ratio was used to represent cytosolic $[Ca^{2+}]_i$. To induce cytoplasmic $Ca^{2+}$ transients, CMs were stimulated by electrically pulsing from 0.1 to 0.5 Hz or by caffeine application as indicated. For electrical stimulations, $Ca^{2+}$ transients were recorded and analyzed after a series of depolarizations that enabled each transient to fully decay so as to establish a steady-state SR content.

Immunostaining

Cells were fixed for 15 min at room temperature with 4% paraformaldehyde in PBS. After washing with PBS, cells were permeabilized in PBS containing 0.2% Triton-100. Primary mouse anti-RyR monoclonal antibody (MA3-925, ABR) was diluted with 10% goat serum at 1:100. Alexa Fluor 488 anti-mouse IgG (A-11029, Invitrogen) was the second antibody used for fluorescence imaging. Hoechst 33342 (H3570, Invitrogen) was used to stain the nuclei. Coverslips were mounted onto glass slides in Prolong Gold antifade reagent (Invitrogen). Samples were imaged on a confocal laser scanning microscope (Clsi, Nikon, Japan).

Western Blot

Proteins (12 µg) were loaded in SDS-polyacrylamide (10%) gel and separated by electrophoresis at 150 V for 2 h. The separated proteins were transferred electrophoretically from the gel onto nitrocellulose membrane at 100 V in 4° C. for 1 h in a buffer containing 25 mM Tris-base, 192 mM glycine and 20% methanol. After the membranes were washed in a buffer (TBS pH 7.4, containing 0.1% Tween-20 and 5% skimmed milk power) for 60 min at room temperature to block non-specific binding, they were probed at 4° C. overnight with anti-SERCA2a (ab2861, abcam), anti-NCX1 (ab2869, abcam), anti-calsequestrin (ab3516, abcam), anti-triadin (sc-33391, Santa cruz), anti-junctin (sc-33367) or anti-calreticulin (ab22683, abcam), respectively. After washing for 30 min with TBS (0.1% Tween-20 solution), the membranes were then incubated for 1 h with a secondary antibody solution conjugated to horseradish peroxidase-conjugated rabbit anti-mouse at 1:2000 dilution. Then the membranes were washed for 30 min with TBS. Detection was performed with an ECL Plus western blotting detection system.

Statistical Analysis

All data were expressed as means±SEM. One-way ANOVA followed by Newman-Keuls multiple comparison tests or paired t test was carried out to test for differences between the mean values within the same study. A difference of $P<0.05$ was considered significant.

Results

Electrically Evoked $Ca^{2+}$ Transients of hESC- and FLV-CMs had Similar Properties.

FIG. 1A-B shows that the basal cytosolic $Ca^{2+}$, an index of $Ca^{2+}$ homeostasis regulated by various $Ca^{2+}$-handling proteins (such as the RyR, SERCA2a, etc), was significantly lower in HES2-CMs (n=17) than that of FLV-CMs (n=15). However, no detectable significant difference was observed between H1- (n=18) and FLV-CMs (p>0.05). Upon electrical stimulations, all of HES2-, H1- and FLV-CMs examined similarly generated $Ca^{2+}$ transients with statistically identical amplitude, maximum upstroke velocity ($V_{max,\ upstroke}$) and maximum decay velocity ($V_{max,\ decay}$) (p>0.05; FIG. 1C-E). The experiments that follow were designed to further explore the basis of and any latent differences in the $Ca^{2+}$ handling properties of HES2-, H1- and FLV-CMs.

Differential Responses of hESC- and FLV-CMs to Caffeine

Figure 2:
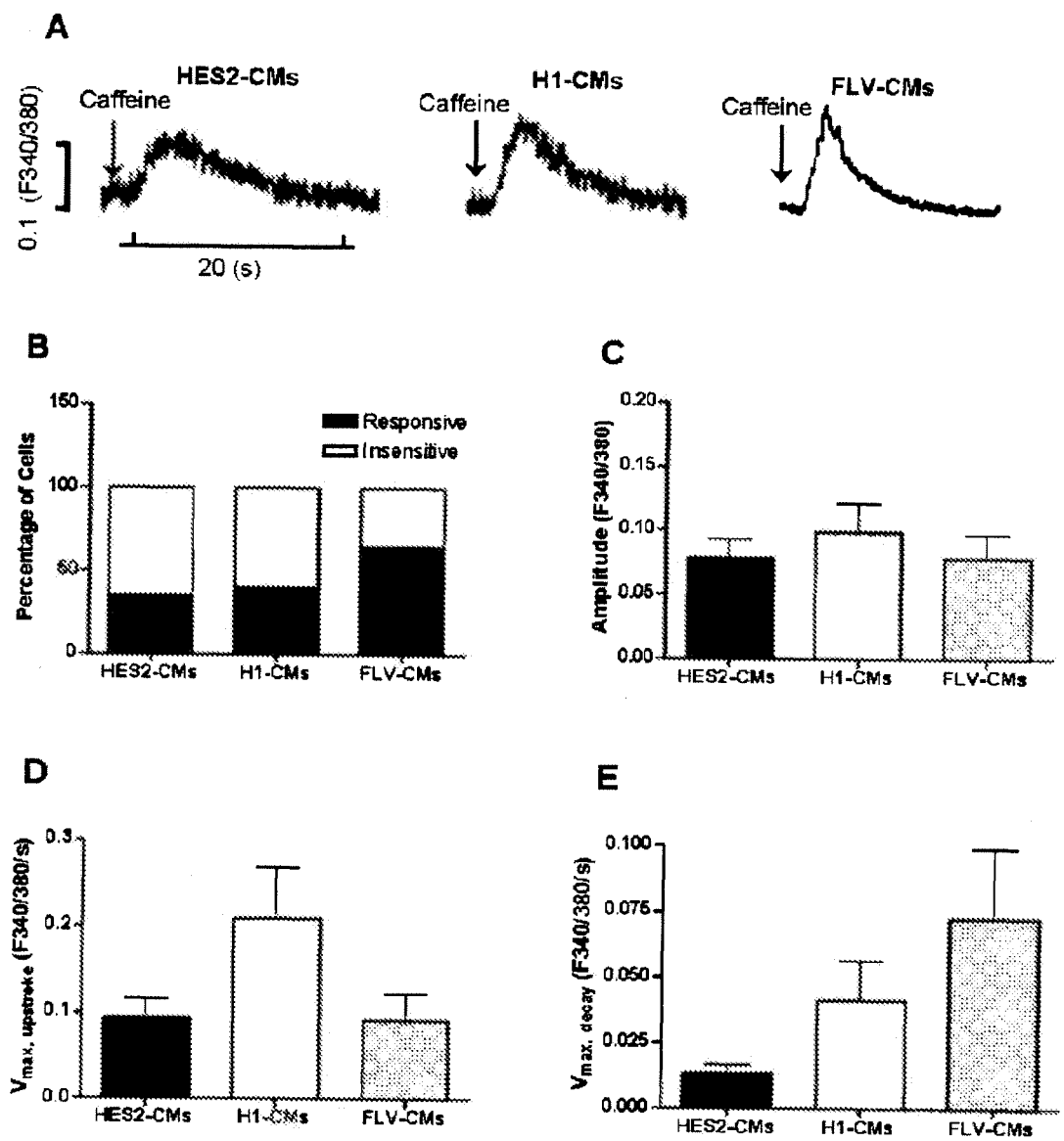
FIG. 2, panels A to D, shows the effect of caffeine on $Ca^{2+}$ transients of HES2-, H1- and FLV-CMs. A) Representative tracings of $Ca^{2+}$ transients induced by caffeine. B) Percentages of caffeine-responsive and -insensitive cells. Total cell numbers were 20, 20 and 17 for HES2-, H1- and FLV-CMs, respectively. C) Amplitude, D) maximum upstroke velocity ($V_{max,\ upstroke}$) and E) maximum decay velocity ($V_{max,\ decay}$) of caffeine-induced transients. Values are expressed as mean±SEM; n32 7, 6 and 9 for HES2-, H1- and FLV-CMs (obtained from 5 hearts), respectively.

To investigate whether functional SRs are indeed expressed in HES2-, H1- and FLV-CMs and their $Ca^{2+}$ contents, studied were conducted to ascertain the effect of caffeine, an activator of RyR, on cytosolic $Ca^{2+}$. To exclude the contribution of trans-sarcolemmal $Ca^{2+}$ influx via voltage-gated $Ca^{2+}$ channels that have been shown to express in hESC-CMs[6], the experiments were performed in the absence of $Ca^{2+}$ in the extracellular bath. FIG. 2A-B shows that a brief exposure to caffeine (10 mM) induced a rise in cytosolic $Ca^{2+}$ that subsequently decayed back to the baseline in 65% of FLV-CMs (n=11 of 17). By contrast, only 35% (n=7 of 20) and 40% (n=8 of 20), respectively, of H1- and HES2-CMs that generated $Ca^{2+}$ transients upon electrical stimulation (cf. FIG. 1), also elicited caffeine-induced $Ca^{2+}$ transients. Despite the lower percentages of caffeine-responsive HES2- and H1-CMs relative to FLV-CMs, the caffeine-induced $Ca^{2+}$ transient amplitudes were not different among themselves (p>0.05; FIG. 2C). Thus, caffeine-responsive hESC-CMs had developed SR loads similar to that of FLV-CMs. Kinetically, H1-CMs displayed the highest $V_{max,\ upstroke}$ (FIG. 2D) but those of HES2- and FLV-CMs were comparable. As for the decay, FLV-CMs were most rapid followed by H- then HES2-CMs (FIG. 2E). These functional differences were further explored below.

Effects of Ryanodine and Thapsigargin on $Ca^{2+}$ Transients of hESC-CMs.

Figure 3:
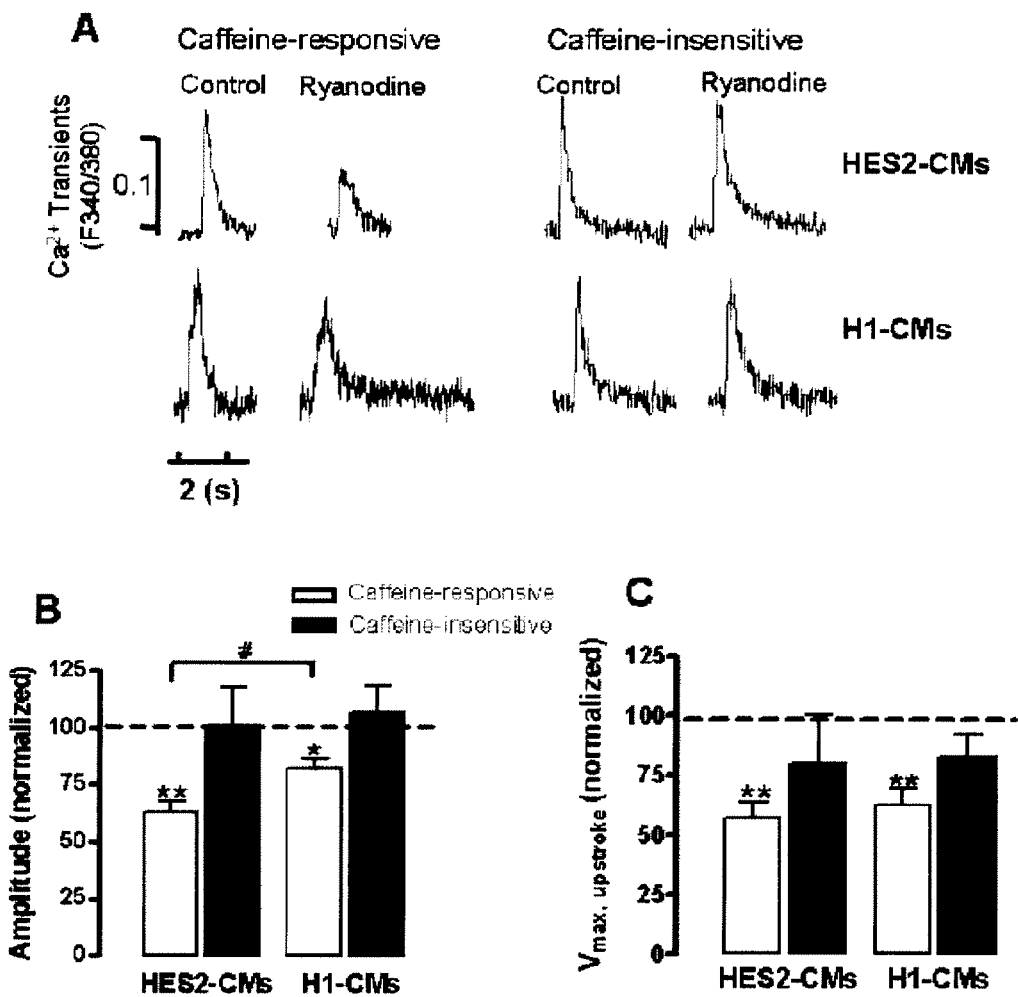
FIG. 3, panels A to C, shows the effect of ryanodine (10 μM) on electrically induced $Ca^{2+}$ transients of caffeine-responsive and -insensitive HES2- and H2-CMs. A) Representative tracings of $Ca^{2+}$ transients in HES2- and H1-CMs before and after incubation with ryanodine for 30 min. B) Amplitude and C) $V_{max,\ upstroke}$ after ryanodine application normalized to values recorded under control ryanodine-free conditions (dashed line i.e. 100%). n=4-6 for caffeine-responsive groups; n=6-7 for caffeine-insensitive groups. * $P<0.05$, ** $P<0.01$ vs. dashed line; # $P<0.05$ HES2- vs. H1-CMs.

The caffeine experiments presented above clearly demonstrate that SRs in HES2- and H1-CMs were indeed expressed and operable. To relate the SR function of HES2- and H1-CMs to $Ca^{2+}$ handling proteins such as RyR and SERCA2a, the effects of their specific inhibitors ryanodine (20) and thapsigargin (21), respectively, on electrically evoked $Ca^{2+}$ transients was examined. FIG. 3A-B shows that after application of 10 µM ryanodine for 30 min, the electrically evoked $Ca^{2+}$ transient amplitudes of caffeine-responsive HES2- and H1-CMs were significantly reduced by 37±4.8 and 18±4.3%, respectively (p<0.05; FIG. 3B, open bars). However, the amplitudes of caffeine-insensitive HES2- and H1-CMs were not affected by ryanodine (FIG. 3B, solid bars). Ryanodine also significantly slowed the $V_{max,\ upstroke}$ of caffeine-responsive but not -insensitive cells (FIG. 3C). Taken collectively, the above observations were consistent with the notion that functional RyRs were present only in caffeine-responsive cells.

Figure 4:
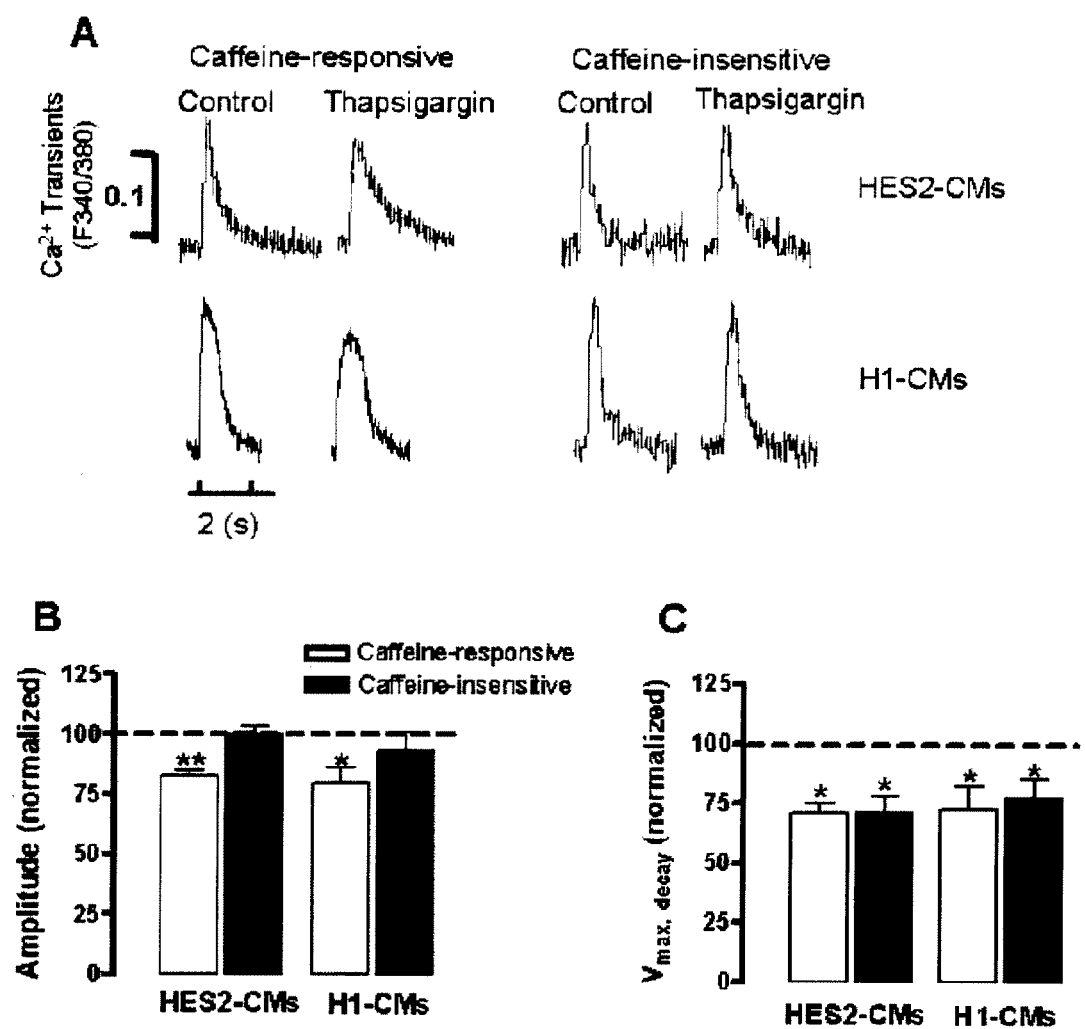
FIG. 4, panels A to C, shows the effect of thapsigargin on the B) amplitude and C) maximum decay velocity ($V_{max,\ decay}$) of electrically induced $Ca^{2+}$ transients in HES2- and H1-CMs. A) Representative tracings of $Ca^{2+}$ transients in HES2- and H1-CMs before and after incubation with thapsigargin for 15 min. Values are normalized to values recorded under control thapsigargin-free conditions (dashed line i.e. 100%); n=4-5 for caffeine-responsive groups; n=6-7 for caffeine-insensitive groups. * $P<0.05$, ** $P<0.01$ vs. dashed line.

In adult human CMs, SERCA2a is responsible for ~70% of $Ca^{2+}$ uptake from the cytoplasm back into the SR (10). FIG. 4A-B shows that thapsigargin application (0.5 µM, 15 min)

significantly reduced the electrically evoked $Ca^{2+}$ transient amplitude of caffeine-responsive HES2- and H1-CMs. This was probably due to inhibited SR $Ca^{2+}$ re-load as a result of SERCA2a blockade by thapsigargin. In accordance with this notion, $V_{max,\ decay}$ of both HES2- and H1-CMs was significantly slowed by thapsigargin (FIG. 4C).

$Ca^{2+}$ Handling Proteins in hESC-, FLV- and ALV-CMs.

Figure 5:
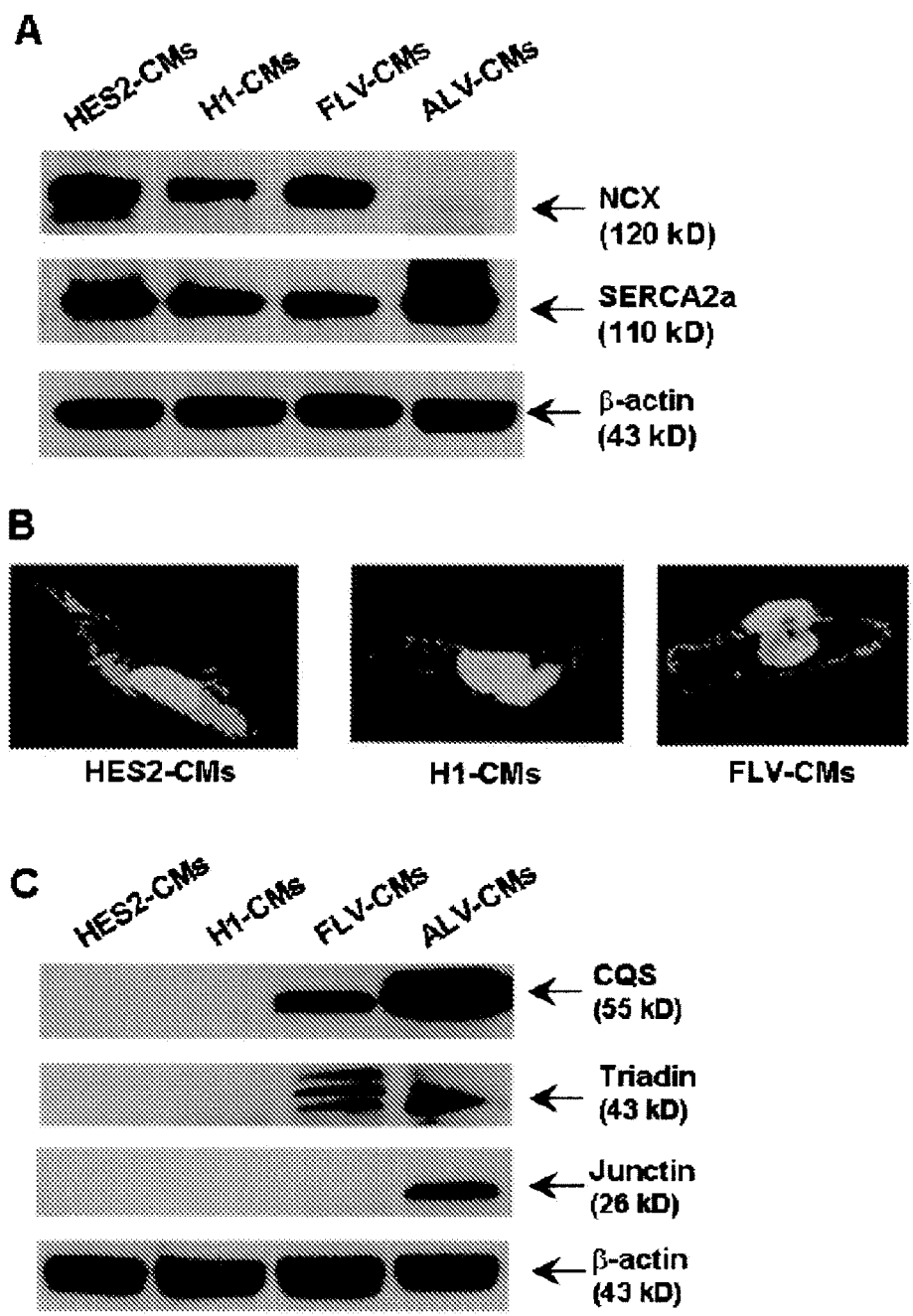
FIG. 5, panels A to D, confirms the expression of various $Ca^{2+}$-handling proteins in HES2-, H1-, FLV- and ALV-CMs. A) A representative Western blot of SERCA2a and NCX. B) Representative confocal images of HES2-, H1- and FLV-CMs after immunostaining for RyR (green, 60×). C) A representative Western blot of junctin, triadin, calsequestrin and D) calreticulin. β-actin was used as the loading control. At least three different experiments were repeated for each of the proteins examined.

FIG. 5A shows a representative Western Blot analysis of SERCA2a and NCX in HES2-, H1-, FLV- as well as human adult left ventricular (ALV-) CMs. All of H1-, HES2- and FLV-CMs expressed comparably high levels of SERCA2a, consistent with the responses of their $Ca^{2+}$ transients to thapsigargin. As anticipated, the expression level of SERCA2a was highest in ALV-CMs (22, 23). Unlike SERCA2a, NCX displayed a different protein expression profile. NCX was most abundant in FLV-CMs but only very weakly expressed in ALV-CMs, consistent with previously published results (24). Interestingly, NCX was substantially expressed in both HES2- and H1-CMs relative to ALV-CMs but much less so in comparison to FLV-CMs.

As for RyR, immunostaining was performed. FIG. 5B shows that RyR was indeed expressed in HES2-, H1- and FLV-CMs. However, the organized, regularly spaced expression pattern as previously reported for adult human ventricular cardiomyocytes (25) was not observed. In the junctional SR membrane, RyR forms a macrocomplex with several regulatory proteins including junctin (Jn), triadin (Trd) and calsequestrin (CSQ). FIG. 5C shows that all of Jn, Trd and CSQ were expressed in ALV-CMs but not HES2- and H1-CMs. As for FLV-CMs, CSQ and Trd but not Jn were expressed, but still at levels substantially less than those of ALV-CMs. Developmentally, immature CMs are known to express significant levels of calreticulin; calreticulin decreases after birth due to post-transcriptional modification and is subsequently replaced by CSQ during SR maturation (26, 27, 28). As anticipated from these previous results, FIG. 5D shows that calreticulin was abundantly and comparably expressed in all of HES2-, H1- and FLV-CMs. Taken collectively, the results indicate that SR related proteins in human heart cells undergo substantial developmental changes.

Discussion

Characterizing the functional properties of hESC-CMs is a crucial first step for their eventual clinical applications for myocardial repair. Although recent studies have revealed several important cellular electrical properties of hESC-CMs, (5, 6, 29) their $Ca^{2+}$ handling properties are much less defined and the availability of relevant data is extremely scarce with only one published report to date (14) (the reported data have been reviewed (31)). As mentioned, proper $Ca^{2+}$ handling is crucial for the successful functional integration of hESC-derived cardiac grafts after transplantation and for ensuring their lack of arrhythmogenicity. In brief, the major findings of the present study are the following: 1) In contrast to the previous report (14), the data above data support that functional SRs (i.e. RyR and SERCA2a) are indeed expressed in hESC-CMs; thus, CICR contributes to $Ca^{2+}$ transients even at early developmental stages, like the murine ESC-CMs (13) 2). Human ESC-CMs that evoke electrically induced $Ca^{2+}$ transients consist of caffeine-responsive and -insensitive cells (with and without functional SR, respectively), probably due to the presence of differentiating CMs of different developmental stages. 3) SERCA2a is expressed in hESC-CMs but at a level substantially less than the adult counterpart; by contrast, NCX is expressed at a higher level in hESC-CMs than adult LV-CMs. 4) The SR-associated $Ca^{2+}$-handling regulatory proteins triadin, calsequestrin and junctin are expressed in adult LV- but not hESC-CMs. These findings are further discussed below i) in comparison to previously published results so as to provide a better basic understanding of the $Ca^{2+}$ handling properties of hESC-CMs, and ii) in relation to the development of novel strategies to facilitate the maturation of hESC-CMs for improving their functional efficacy for therapies.

Same as the study by Dolnikov and colleagues (14), $Ca^{2+}$ transients could be readily generated from both HES2- and H1-CMs upon electrical stimulations. Unlike the previous report, however, at least two sub-populations, caffeine-responsive and -insensitive, were present in hESC-CMs and FLV-CMs. Caffeine induces large $Ca^{2+}$ transients in ~38% of hESC-CMs, indicating that this caffeine-responsive sub-population expresses functional SRs and RyRs that are capable of loading and unloading $Ca^{2+}$. The percentage of caffeine-responsive cells is higher in FLV-CMs (~65%). The difference could be attributed to the presence of a larger population of developmentally immature hESC-CMs with un- or under-developed SR; indeed, increased SR load has been suggested to improve the efficacy of voltage-gated $Ca^{2+}$ currents as a trigger for SR $Ca^{2+}$ release for effective excitation-contraction coupling (32, 33, 34). Although ~85% and 60% of HES2- and H1-CMs, respectively, belong to the ventricular type, atrial and pacemaker derivatives are also known to be present in spontaneously contracting human embryoid bodies, (5, 6, 16) this heterogeneity of chamber-specific cells likely further contributes to the lower percentages of caffeine-sensitive hESC-CMs. Human ESC lines whose cardiac derivatives have been genetically labeled, such as that recently described by Huber et al (35), will be useful tools for distinguishing among these possibilities.

Dolnikov et al reports that neither ryanodine nor caffeine affects $Ca^{2+}$ transients of hESCs (14). This apparent difference is indeed consistent with the present results and can be readily accounted for by the caffeine-responsive population newly identified in the present study. In the above recordings, only $Ca^{2+}$ transients of caffeine-responsive but not -insensitive cells can be functionally inhibited by ryanodine. Immunostaining confirms the expression of RyR proteins in hESC-CMs. However, the expression pattern is distinct from the highly organized distribution seen in adult cardiomyocytes (25) but similar to that of FLV-CMs. Although human and murine (m) ESCs (and their cardiac derivatives) differ in many important ways, the developmental aspect of the $Ca^{2+}$-handling properties of hESCs resembles that of mESCs: RyRs are expressed in very early stages and can be caffeine-induced to lead to $Ca^{2+}$ transients for contractions (36). Of note, 18- to 24-day old hESC-CMs were investigated in the present study. According to Sartiani et al (18), these hESC-CMs can be considered as early CMs (15-40 days), whose electrophyiological properties are relatively immature. This notion is consistent with the above observation that only ~38% of the hESC-CMs expressed functional SR. Nonetheless, sarcomeres were displayed as shown by MHC, α-actinin and tropomyosin staining although much less evident and defined than those in adult CMs. Furthermore, although these cells were chronologically younger than those investigated by Dolnikov and colleagues (55 day-old H9.2-CMs), relatively more mature $Ca^{2+}$ handling properties (as gauged by their responsiveness to caffeine) were observed. Collectively, the differences between their study and this study could be attributed to the different culturing, differentiation and experimental conditions (e.g., clusters of 10-15 cells rather than the entire beating outgrowths from intact hEBs were chosen for these experiments) as well as other intrinsic differences between the different hESC lines studied (H9.2 and I3 vs. H1 and HES2 for these experiments). Based on these results, a novel strategy for driven maturation is provided.

In mESC-derived CMs, it has been suggested that spontaneous $Ca^{2+}$ transients are triggered by inositol-1,4,5-trisphosphate ($IP_3$)-mediated $Ca^{2+}$ release which are then amplified and modulated by RyR-mediated $Ca^{2+}$ release (37). $IP_3$ receptor is highly expressed in conductive CMs in either embryonic or adult hearts (38). Considering the role of $IP_3$ in automaticity and generation of arrhythmias, $IP_3$-sensitive stores may play an important role in hESC-CMs but further experiments will be required to test this notion.

Immature $Ca^{2+}$ handling properties of hESC-CMs can cause poor functional integration with the host myocardium at best, or lethal arrhythmias at worst. Thus, it is desirable to develop methods for facilitating their maturation ex vivo. Since RyR and SERCA2a are already expressed, targeted expression of the regulatory proteins that are largely absent in hESC-CMs (such as junctin, triadin, calsequestrin and phospholamban) via gene transfer or protein transfection might render their SR and $Ca^{2+}$ handling properties more mature or adult-like. Additionally, NCX is highly expressed in hESC- and FLV-CMs but not in ALV-CMs. It has been reported that NCX expression in human heart developmentally peaks at 20-week gestation, and is substantially higher than that in adult heart (24); the reduction of NCX expression may be a compensatory response to the increased SERCA activity. Thus, suppressing NCX activity in hESC-CMs can achieve the high SERCA2a:NCX ratio in adult CMs for driven maturation and for maintaining Ca homeostasis.

EXAMPLE 2

Atomic Force Microscopy (AFM) and Fluorescent Staining of Mature-CM and hESC-CM

Figure 6:
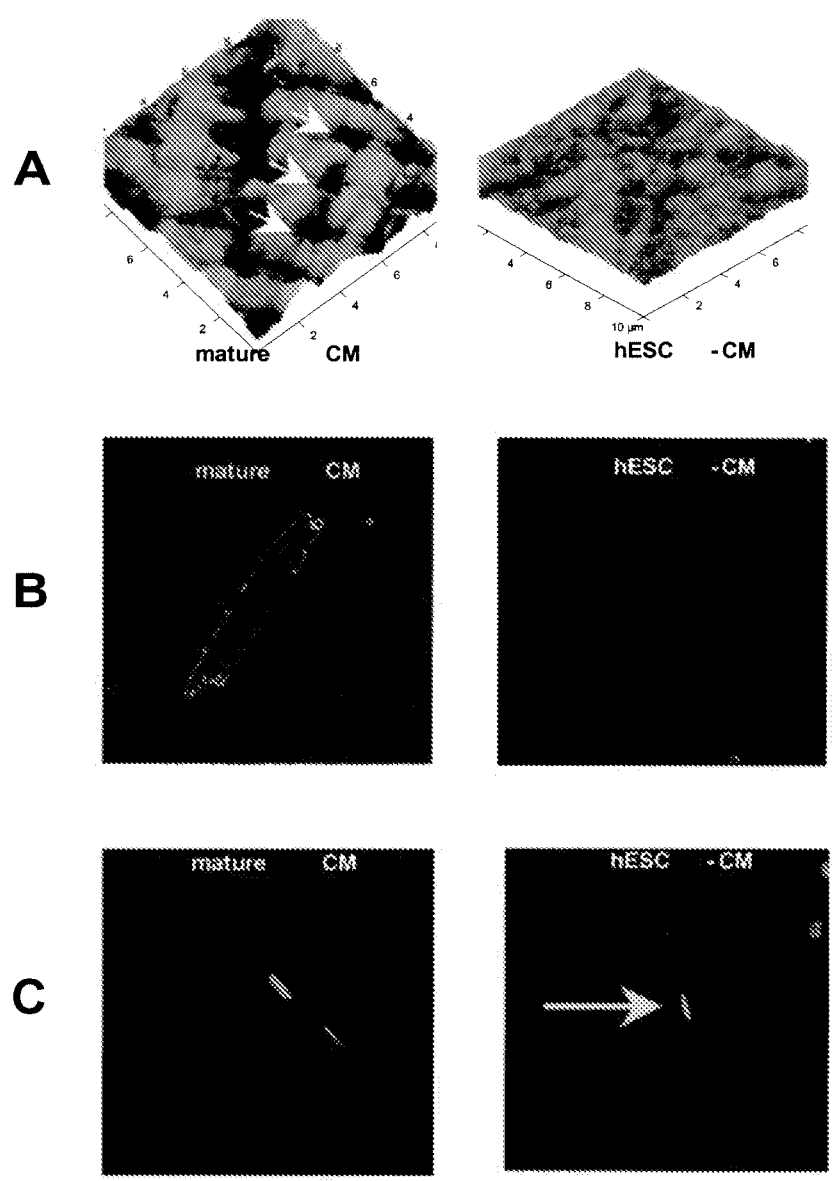
FIG. 6, panels A to C, shows the presence or absence of t-tubules and t-tubule development-associated with caveolin 3 in mature and hESC-CMs. A) AFM images of adult guinea pig CM with t-tubules (indicated by arrows) and hESC-CM missing t-tubules. B) Immunofluorescent staining of t-tubules in guinea pig CM with regular bright spots and hESC-CM shows no staining C) Caveolin 3 is present in mature but absent in hESC-CM (indicated by arrow).

The presence of t-tubules and t-tubule development-associated with caveolin 3 in mature and hESC cardomycytes were tested. Structurally, hESC-CMs lack t-tubules as shown by AFM (FIG. 6A). Fluorescent staining for t-tubules and hESC-CM shows the absence of regular bright spots in the hESC-CM indicating the absence of t-tubules (FIG. 6B). Additionally, caveolin 3, a protein involved in t-tubule biogenesis that is normally present in mature CMs, is absent in hESC-CM (FIG. 6C). Thus, it is highly desirable to facilitate the maturation of t-tubules in hESC-CM via targeted expression of the regulatory proteins so as to render the sarcoplasmic reticulum and specifically the $Ca^{2+}$ handling properties more mature or adult-like.

EXAMPLE 3

Gene Transfer

While the adenovirus- and lentivirus-mediated protocols given here are examples, unlimited examples, other relevant methods for gene/protein delivery (e.g., protein transfection, homologous recombination, extrachromosomal modifications, etc) can be similarly employed.

The full-length coding sequence of the transgene(s) of interest are cloned into the multiple-cloning site of pAdCMV-GFP-IRES (pAd-CGI) to generate the corresponding ultimate construct. Adenoviruses are generated by Cre-lox recombination of purified ψ5 viral DNA and shuttle vector DNA. The recombinant products are plaque purified, expanded, and purified by CsCl gradient, yielding concentrations on the order of $10^{10}$ PFU/ml. For transduction, adenoviral particles are added at a concentration of $\sim 2 \times 10^9$ PFU.

For transplantation experiments, lentivirus (LV)- rather than adenovirus-mediated gene transfer are employed (39). Specifically, the two-vector doxycycline (DOX)-inducible expression system (40) recently demonstrated in ESCs (41) is employed. Briefly, TR-KRAB is a tetracycline-controlled fusion protein that contains the TR fused to the Kruppel-associated box (KRAB) domain of human Kox1 (42). KRAB, a 75-amino-acid transcriptional repression module in many zinc finger-containing proteins, suppresses transcription within 3 kb from its binding site in an orientation-independent manner (42-45). When fused to the DNA-binding domain of TR, KRAB can modulate transcription from an integrated promoter juxtaposed with the tet operator (tetO) sequence (43-45). In the absence of DOX, TR-KRAB binds specifically to tetO and thereby suppresses any nearby promoter(s). By contrast, the presence of DOX will sequester TR-KRAB away from tetO to enable transgene expression (40).

In all cases, the ubiquitously active promoter EF-1α is chosen to drive transgene to avoid silencing in undifferentiated ESCs. To generate the ultimate construct, GFP of pLV-THM-GFP is replaced with the transgene of interest. The recombinant lentiviruses are produced by transient transfection of HEK293T cells as previously described (46). Briefly, the lentiviral plasmids pΔ8.91, pMD.G, and pLV-THM-Kir2.1GFP or pLV-TR-KRAB-dsRed (2:1:3 mass ratio) are co-transfected into HEK293T cells seeded at a density of $6 \times 10^6$ cells per 10-cm dish 24 h prior to transfection. The supernatant containing lentiviral particles are harvested at 24 and 48 h post-transfection and stored at −80° C. before use. LV-TR-KRAB-IRES-dsRed and LV-THM-transgene(s) are co-introduced into m- and hESCs successively in the same order as previously described (39, 47). dsRed+ and/or GFP+ cells are identified by their epifluorescence and sorted by MoFlo (Dako, Ft. Collins, Colo.). Co-transduced ESC-CMs are cultured in presence or absence of DOX (1 µg/ml, Sigma) as needed. The animals are pre-treated with DOX (5 mg/kg/day) at least 5 days before injection and continue to receive treatment after transplantation during the course of the experiment.

EXAMPLE 4

Facilitated Maturation of Human Embryonic Stem Cell-derived Cardiomyocytes in $Ca^{2+}$ Handling via Expression of Calsequestrin $Ca^{2+}$ homeostasis is dependent on $Ca^{2+}$-handling proteins such as L-type $Ca^{2+}$ ($I_{Ca,L}$) channels, RyR, SERCA and NCX. RyRs are arranged in large organized arrays (up to 200 nm in diameter with more than 100 RyRs) at the junctions between the SR and sarcolemma (i.e. t-tubules) beneath $I_{Ca,L}$ channels. These arrays constitute a large functional $Ca^{2+}$ release complex. RyRs are also coupled to other proteins at the luminal SR surface such as triadin, junctin and calsequestrin (CSQ). As the most abundant, high-capacity but low-infinity $Ca^{2+}$-binding protein in the SR, the cardiac isoform CSQ2 can store up to 20 mM $Ca^{2+}$ while buffering the free SR [$Ca^{2+}$] at ~1 mM. This allows repetitive muscle contractions without rundown. CSQ2 also coordinates the rates of SR $Ca^{2+}$ release and loading by modulating RyR activities. Indeed, the SR $Ca^{2+}$ content affects the amount of $Ca^{2+}$ released via CICR. For a given $I_{Ca,L}$ trigger, a high SR $Ca^{2+}$ load enhances the open probability of RyRs while directly providing more $Ca^{2+}$ available for release. By contrast, $I_{Ca}$ can no longer cause CICR when the SR $Ca^{2+}$ content is sufficiently low. Mechanistically, CSQ senses the levels of luminal $Ca^{2+}$ and effects RyRs via triadin and junctin. For instance, when SR $Ca^{2+}$ declines (e.g., during $Ca^{2+}$ release), the increased level of $Ca^{2+}$-free CSQ deactivates RyRs by binding via triadin and junctin;

alternatively, SR Ca$^{2+}$ reload (e.g., upon relaxation when CICR terminates) relieves the CSQ2-mediated inhibition of RyRs. Thus, CSQ2 is an important determinant of the SR load. Interestingly, CSQ can activate purified RyRs in the absence of triadin and junction. (71, 72)

Human embryonic stem cells (hESCs), isolated from the inner cell mass of blastocysts, can self-renew while maintaining their pluripotency to differentiate into all cell types (10), including cardiomyocytes (CMs) (14, 48-51). Therefore, hESCs may provide an unlimited ex vivo source of CMs for cell-based heart therapies. Although hESC-derived CMs (hESC-CMs) have been reported to improve cardiac function in several animal myocardial infarct models (52, 53), numerous hurdles need to be overcome before their clinical applications. As shown in Example 1 above, Ca$^{2+}$-handling properties are functional in hESC-CMs, but are immature relative to the adult form. Indeed, a number of crucial Ca-handling proteins are differentially expressed in hESC-, fetal and adult CMs. CSQ that is robustly expressed in adult CMs is completely absent in hESC-CMs (FIG. 5C). The effects of CSQ expression on the Ca$^{2+}$-handling properties of hESC-CMs were evaluated in the following experiments.

hESC Culturing and Differentiation

H1 cells (WiCells, Madison, Wis.) were grown on irradiated mEFs from 13.5-day embryos of CF-1 mice and propagated as previously described (3). Briefly, the culture medium consisted of 80% Dulbecco's modified Eagle's medium, 20% knockout serum replacement, 4 ng/ml basic fibroblast growth factor, 1 mmol/L glutamine, 0.1 mmol/L β-mercaptoethanol, and 1% nonessential amino acid solution (all from Invitrogen, Carlsbad, Calif.). To induce the formation of embryoid bodies (EBs), H1 cells were detached using 1 mg/mL type IV collagenase (Invitrogen) and transferred to petri dishes containing 80% Dulbecco's modified Eagle's medium, 20% fetal bovine serum defined (HyClone, Logan, UT), 1 mmol/L glutamine, and 1% nonessential amino acid stock in the absence of b-FGF. The aggregates were cultured in suspension for 7 days, followed by plating on gelatin-coated (0.1%; Sigma-Aldrich, St. Louis) 6-well plates to form H1-CMs.

Construction of Recombinant Adenoviruses

Human cardiac calsequestrin 2 (sc119365, Origene technologies, MD) was cloned and ligated into adenovirus shuttle vectors pAdCMV-IRES-GFP using primers creating Bmt and Spe I sites (pAdCMV-CSQ-IRES-GFP). IRES, internal ribosomal entry site, allows the simultaneous translation of CSQ and the fluorescence marker (GFP) with a single transcript. The truncated CSQ mutant was constructed in pAdCMV-IRES-GFP by deleting 817 bp (53 bp-869 bp) using the two EcoN I sites inside CSQ's coding sequence (Ad-CSQΔ). The resulting product after Hind III cutting was self-ligated to produce another control of pAdCMV-GFP (Ad-GFP). Adenoviruses were generated by Cre-lox recombination of purified ψ5 viral DNA and shuttle vector DNA using Cre4 cells as described previously (56). The recombinant products were plaque purified, amplified, and purified again by Vivapure Adenopack Kit (Vivascience Ltd, UK), yielding concentrations of the order of $10^9$ plaque-forming units (PFU) ml$^{-1}$.

Isolation of hESC-CMs and Adenoviral Gene Transfer

For isolating H1-CMs, beating outgrowths were microsurgically dissected from H1- derived EBs (7+14 to 7+21 days) by a glass knife, followed by incubation in collagenase II (1 mg/mL) at 37° C. for 30 min. The isolated cells were incubated with KB solution containing (mM): 85 KCl, 30 K$_2$HPO$_4$, 5 MgSO$_4$, 1 EGTA, 2 Na$_2$-ATP, 5 pyruvic acid, 5 creatine, 20 taurine, 20 d-glucose, at room temperature for 30 min. After the cells were plated on gelatin-coated glass coverslips for 1 hr at 37° C., regular culture media was added.

After 48 hours, plated H1-CMs were infected with adenoviruses for 3 hours. Recordings were performed within 24-48 hrs after infection.

Real-time PCR

Total RNA was extracted with RNeasy Mini kit (Qiagen Inc., CA). The amount of RNA was measured with a spectrophotometer and the purity was confirmed by the absorbance ratio at A260/280. Reverse transcription was done by use of QuantiTect Reverse Transcription Kit (Qiagen Inc., CA). Quantitative PCR was carried out using Platinum SYBR green qPCR SuperMix-UDG (Invitrogen, CA) and MyiQ™ Optical Module (BioRad, CA) according to the manufacturer's instructions. Primers for CSQ, RyR, junction, triadin, SERCA2a, L-type Ca$^{2+}$ channel (CAV1.2) and calreticulin were designed using Oligo Perfect Software (Invitrogen, CA).

Measurements of Cytosolic Ca$^{2+}$

A spectrofluorometric method with Fura-2/AM as the Ca$^{2+}$ indicator was used for measuring [Ca$^{2+}$]$_i$. H1-CMs were incubated with 10 μM Fura-2/AM and 0.2% pluronic F-127 for 30 min at 37° C. Fluorescent signals obtained upon excitation at 340 nm (F340) and 380 nm (F380) were recorded from cells perfused with Tyrode solution containing (mM): 140 NaCl, 5.0 KCl, 1.0 CaCl$_2$, 1.0 MaCl$_2$, 10.0 glucose and 10 HEPES (pH 7.4) unless otherwise indicated. Data were analyzed using the Ionwizard software (Version 5, IonOptix) to generate the Ca$^{2+}$ transient parameters reported in this study. The F340/F380 ratio was used to represent cytosolic [Ca$^{2+}$]$_i$. To induce cytoplasmic Ca$^{2+}$ transients, CMs were stimulated by electrically pulsing from 0.1 to 0.5 Hz or by caffeine application as indicated.

For electrical stimulations, Ca$^{2+}$ transients were recorded and analyzed after a series of depolarizations that enabled each transient to fully decay so as to establish a steady-state SR content.

L-type Ca$^{2+}$ current ($I_{ca,L}$) Measurements $I_{ca,L}$ was recorded from single H1-CMs after 24-48 hrs transduction using whole-cell patch clamp with an Axopatch 200B amplifier and the pClamp9.2 software (Axon Instruments Inc., Foster City, Calif.) in a bath solution containing (mM) 110 NaCl, 30 KCl, 1.8 CaCl$_2$, 0.5 MgCl$_2$, 5 HEPES, and 10 glucose (PH 7.4) at 37° C. Patch pipette solution contained (mM): 110 K$^+$ aspartate, 20 KCl, 1 MgCl$_2$, 0.1 Na-GTP, 5 Mg-ATP, 5 Na$_2$-phospocreatine, 1 EGTA, 10 HEPES, pH adjusted to 7.3 with KOH. To elicit Ca$^{2+}$ currents ($I_{Ca,L}$), cells were held at a −40 mV potential and pulsed from −40 mV to +60 mV with 10 mV increments for 2 s. L-type Ca$^{2+}$ currents ($I_{Ca,L}$) was defined as 5 mM nifedipine-sensitive currents.

Di-8-ANEPPS Staining of T-tubule

H1-CMs were fixed with 4% paraformaldehyde for 15 min at room temperature and then incubated with 10 μM Di-8-ANEPPS (Invitrogen, CA) for 5 min at room temperature. After washing for 10 min with PBS, the mid-planes of the cell height were imaged on a confocal laser-scanning microscope (Clsi; Nikon, Tokyo).

Statistical Analysis

All data were expressed as means±SEM. One-way ANOVA followed by Newman-Keuls multiple comparison tests or paired t test was carried out to test for differences between the mean values within the same study. A difference of P<0.05 was considered significant.

Results

Unchanged Expressions of Other Ca$^{2+}$ Handling Proteins

Figure 7:
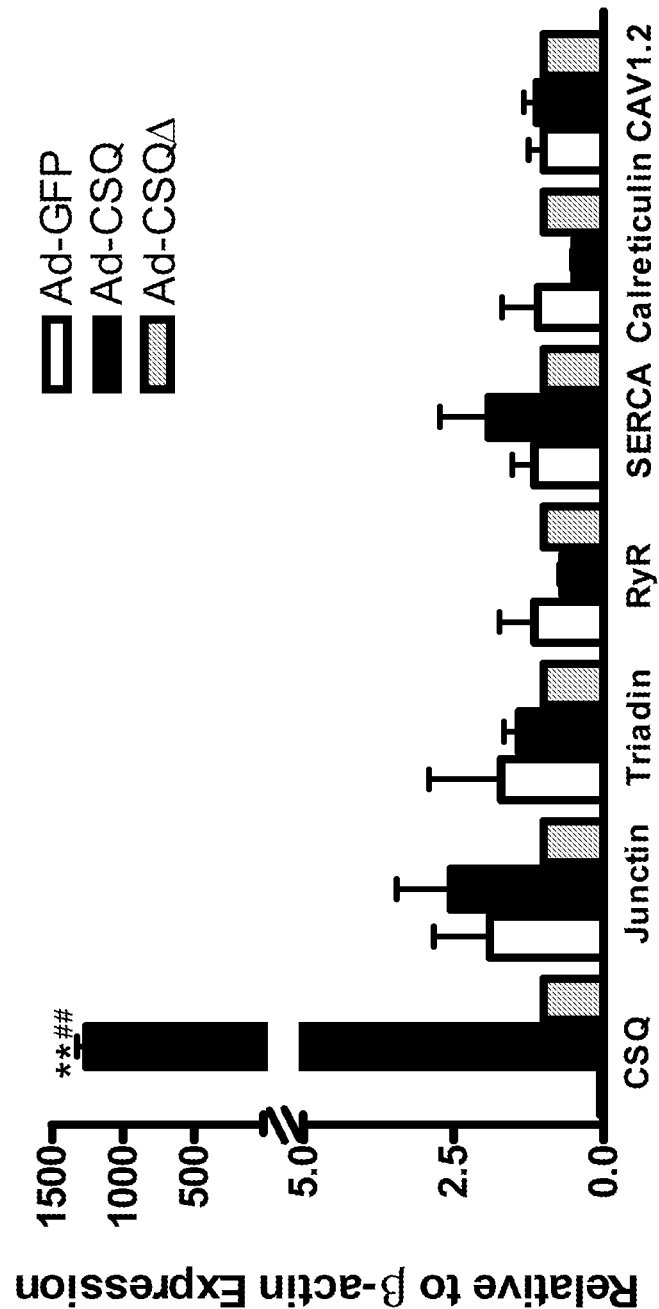
FIG. 7 shows relative expression of various $Ca^{2+}$ handling proteins by real-time PCR. CAV1.2 is an L-type $Ca^{2+}$ channel. Relative expression levels for adenoviral-derived constructs Ad-GFP and Ad-CSQ groups were normalized to those of adenoviral-derived construct Ad-CSQΔ. Values are expressed as mean±SEM; n=3. ** $P<0.01$ vs. Ad-CSQΔ; ## $P<0.01$ vs. Ad-GFP.

CSQ mRNA was significantly elevated in H1-CMs infected with pAdCMV-CSQ-IRES-GFP (Ad-CSQ) by 1258±92-fold, in comparison to both fluorescence (Ad-GFP)

and the truncated CSQ mutant (Ad-CSQΔ) controls (FIG. 7). Appearance of the fluorescence marker, GFP, was used to determine the infection rates of the H1-CMs cells in each group. The truncated CSQ mutant (Ad-CSQΔ) produced no functional CSQ, which is consistent with previous reports in which a stop codon was inserted after 71st amino acid (57).

In adult CMs, CSQ associates with triadin and junctin to regulate RyR, forming the RyR $Ca^{2+}$ release complex. Therefore, the effect of CSQ expression on the mRNA levels of these related proteins was investigated. mRNA levels of RyR, triadin and junctin were unchanged upon the expression of CSQ in Ad-CSQ group (FIG. 7). Similarly, no concomitant alterations occurred in mRNA levels of SERCA, L-type $Ca^{2+}$ channel (CAV1.2) and calreticulin. Calreticulin is another SR $Ca^{2+}$-binding protein, which decreases after birth once CSQ assumes its principle role (27). The unchanged profile of these $Ca^{2+}$ handling proteins indicates that the herein described functional alterations resulted from acute responses to the short-term addition of CSQ alone.

Increased SR $Ca^{2+}$ Content

Figure 8:
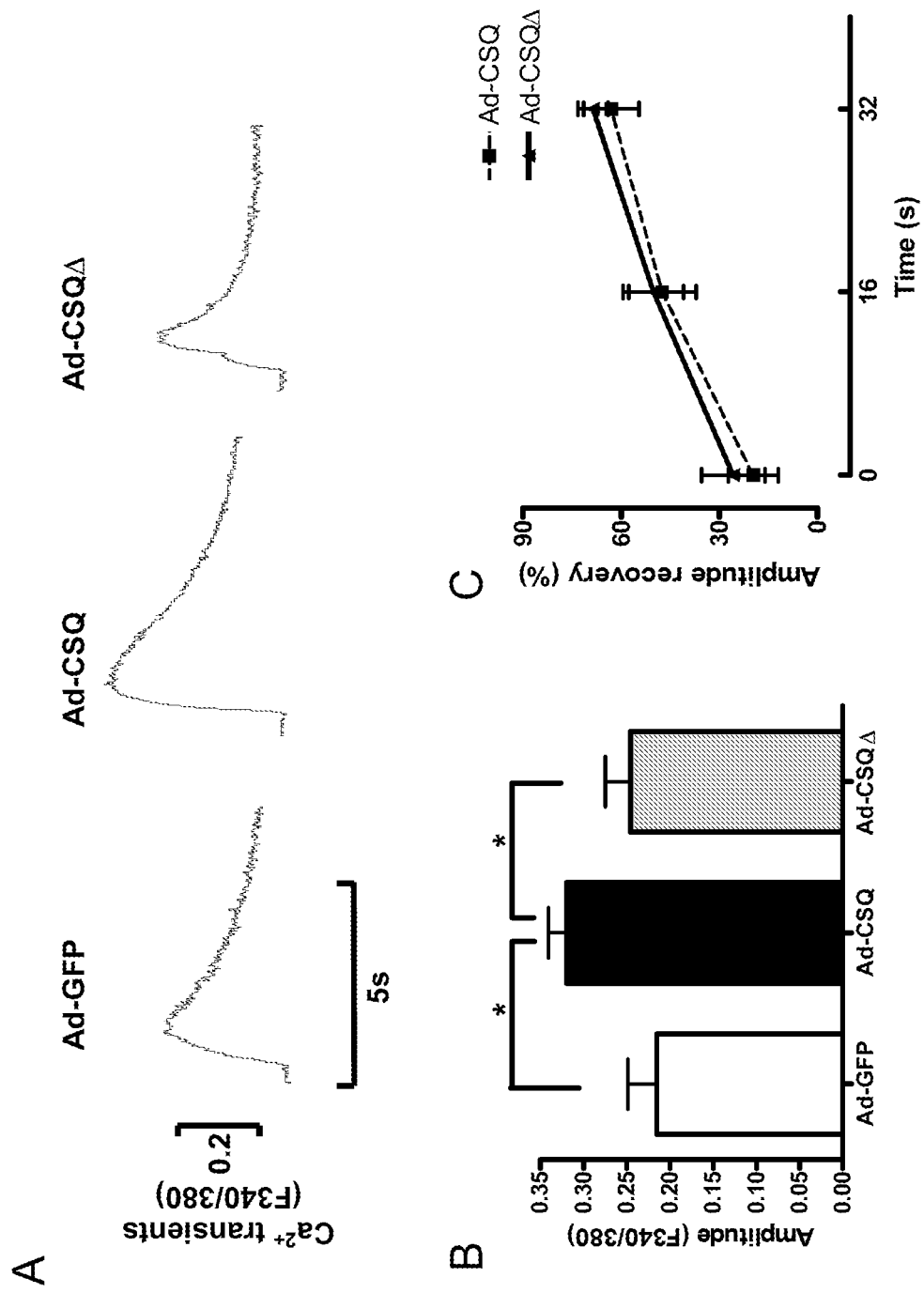

As CSQ is an important determinant of SR $Ca^{2+}$ load, application of caffeine (10 mM) was used to assess influences of CSQ expression on the total $Ca^{2+}$ storage capacity of SR. Consistent to previous reports on the presence of caffeine-sensitive $Ca^{2+}$ store in hESC-CMs (48, 58), a brief exposure to caffeine elicited a robust cytosolic $Ca^{2+}$ increase. As anticipated, the peak was significantly larger in H1-CMs expressed CSQ (FIG. 8A and FIG. 8B). This indicates a substantial increase in SR $Ca^{2+}$ content upon the higher $Ca^{2+}$ binding activity is conferred by the presence of CSQ.

Figure 11:
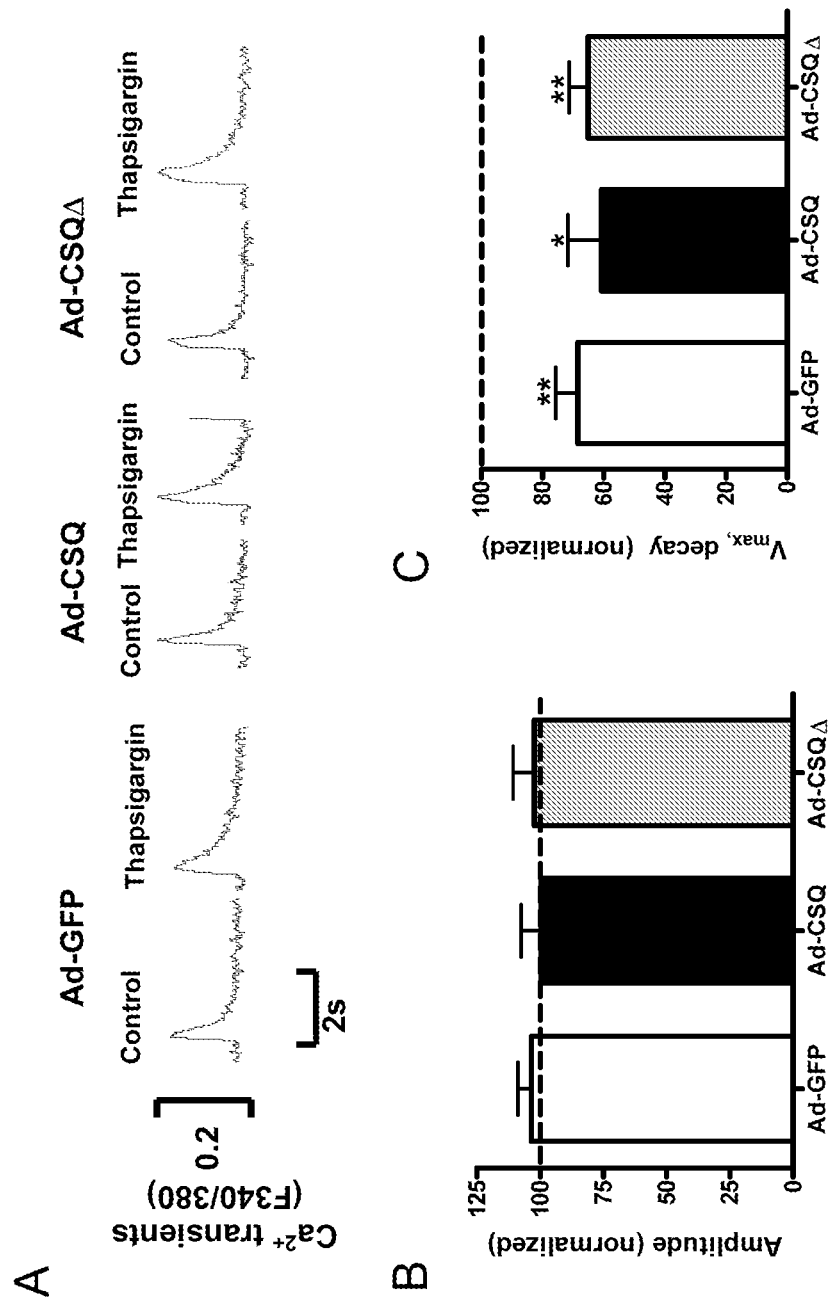
FIG. 11, panels A to C, shows the effects of thapsigargin (0.5 μM) on electrically induced $Ca^{2+}$ transients. A) representative tracings of $Ca^{2+}$ transients in Ad-GFP, Ad-CSQ and Ad-CSQΔ before and after incubation with thapsigargin for 15 min. B) amplitude and C) maximum decay velocity ($V_{max,\ decay}$) normalized to values recorded under control thapsigargin-free conditions (dashed line i.e. 100%); n=7, 6 and 6 for Ad-GFP, Ad-CSQ and Ad-CSQΔ, respectively. * $P<0.05$, ** $P<0.01$ vs. dashed line. CSQ expression does not negatively alter the pharmacology of $Ca^{2+}$ transients.

The SR $Ca^{2+}$ depletion by caffeine was followed by the reoccurrence of electrically induced $Ca^{2+}$ transients with progressively increased amplitudes as SR was recharged gradually. The recharging rate mainly depends on activity of SERCA or the functional size of SR. Although CSQ supplement led to increased SR store and unchanged SERCA expression (FIG. 7) and activity (FIG. 11), transient amplitude recovery taken at three different time points showed no significant difference between Ad-CSQ and Ad-CSQΔ (FIG. 8C).

Enhanced Magnitude and Kinetics of $Ca^{2+}$ Transients

Figure 9:
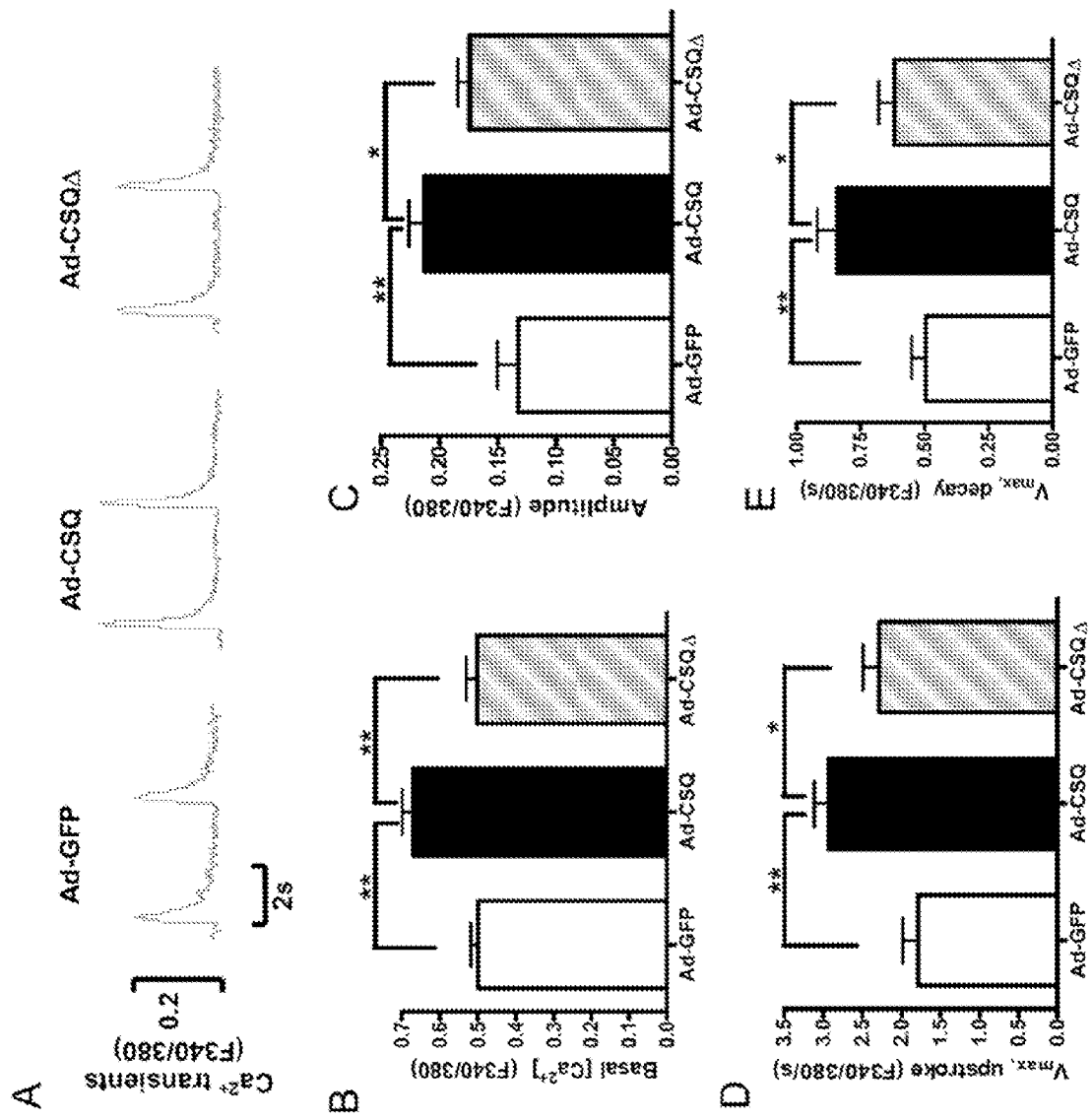

To investigate whether CSQ expression in hESC-CMs can facilitate their developments of $Ca^{2+}$ handling properties and thereby the contractile functions, electrically induced $Ca^{2+}$ transients were characterized and compared. Basal cytosolic $Ca^{2+}$ was elevated remarkably in hESC-CMs infected with Ad-CSQ compared to Ad-GFP and Ad-CSQΔ (FIG. 9B). Example 1 shows that hESC-CMs have lower cytosolic $Ca^{2+}$ than human fetal CMs. hESC-CMs infected with Ad-CSQ generated larger transients with a higher upstroke and decay velocity, indicating that CSQ expression in H1-CMs enhanced the SR $Ca^{2+}$ release, which is correlated with more forceful contraction (FIG. 9C to FIG. 9E). Taken collectively, this observation may suggest a developmental improvement of the $Ca^{2+}$ homeostasis after CSQ expression in hESC-CMs. This higher cytoplasmic $Ca^{2+}$ concentration may explain the faster $Ca^{2+}$ transient decay (FIG. 9D) since $Ca^{2+}$ extrusion via NCX possibly increased as a result.

Unchanged Effects of Ryanodine and Thapsigargin on $Ca^{2+}$ Transients

Figure 10:
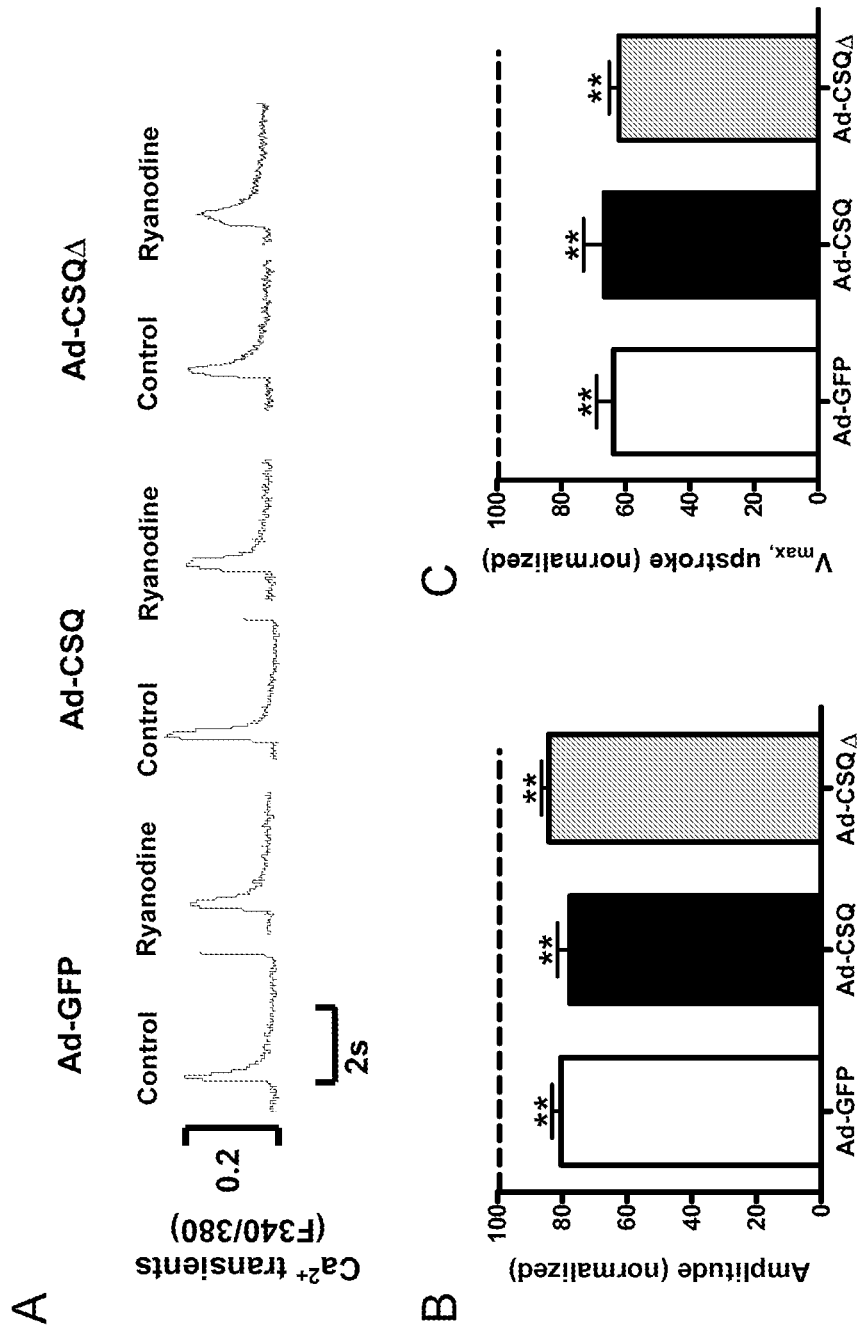
FIG. 10, panels A to C, shows the effects of ryanodine (10 μM) on electrically induced $Ca^{2+}$ transients. A) Representative tracings of $Ca^{2+}$ transients in Ad-GFP, Ad-CSQ and Ad-CSQΔ before and after incubation with ryanodine for 30 min. B) Amplitude and C) $V_{max,\ upstroke}$ after ryanodine application normalized to values recorded under control ryanodine-free conditions (dashed line i.e. 100%). n=5, 8 and 5 for Ad-GFP, Ad-CSQ and Ad-CSQΔ, respectively. ** $P<0.01$ vs. dashed line. CSQ expression does not negatively alter the pharmacology of $Ca^{2+}$ transients.

CSQ is known as an important regulator of RyR, therefore the influences of CSQ expression on RyR activity was investigated by application of its inhibitor, ryanodine. As seen in Example 1, incubation with 10 μM ryanodine for 30 minutes significantly decreased the electrically evoked $Ca^{2+}$ transient amplitude (78%, 80% and 84%) and slowed the upstroke velocity (67%, 64% and 62%) in Ad-CSQ, Ad-GFP and Ad-CSQΔ, respectively (FIG. 10). However, the inhibitory effects were identical between H1-CMs with and without CSQ expression. Therefore the improved $Ca^{2+}$ release observed in this study is not likely due to enhanced expression or function of RyR, but a delicate regulation on RyR conferred by CSQ.

Similarly, thapsigargin, a specific inhibitor of SERCA, significantly decreased the decay velocity in all three groups (61%, 69% and 65% for Ad-CSQ, Ad-GFP and Ad-CSQΔ, respectively) after 15 min incubation, confirming the existence of the functional $Ca^{2+}$ reuptake protein (SERCA) responsible for SR reload in hESC-CMs (FIG. 11C). The unchanged transient amplitude is likely due to the trans-sarcolemmal $Ca^{2+}$ cycling which partly contributes to the $Ca^{2+}$ transients in H1-CMs beyond the immature CICR mechanism (FIG. 11B). In accordance to the stable expression of SERCA (FIG. 7), the blocking effects of thapsigargin on $Ca^{2+}$ transients were the same, regardless of CSQ expression.

Unchanged L-type $Ca^{2+}$ Currents ($I_{ca,L}$)

Figure 12:
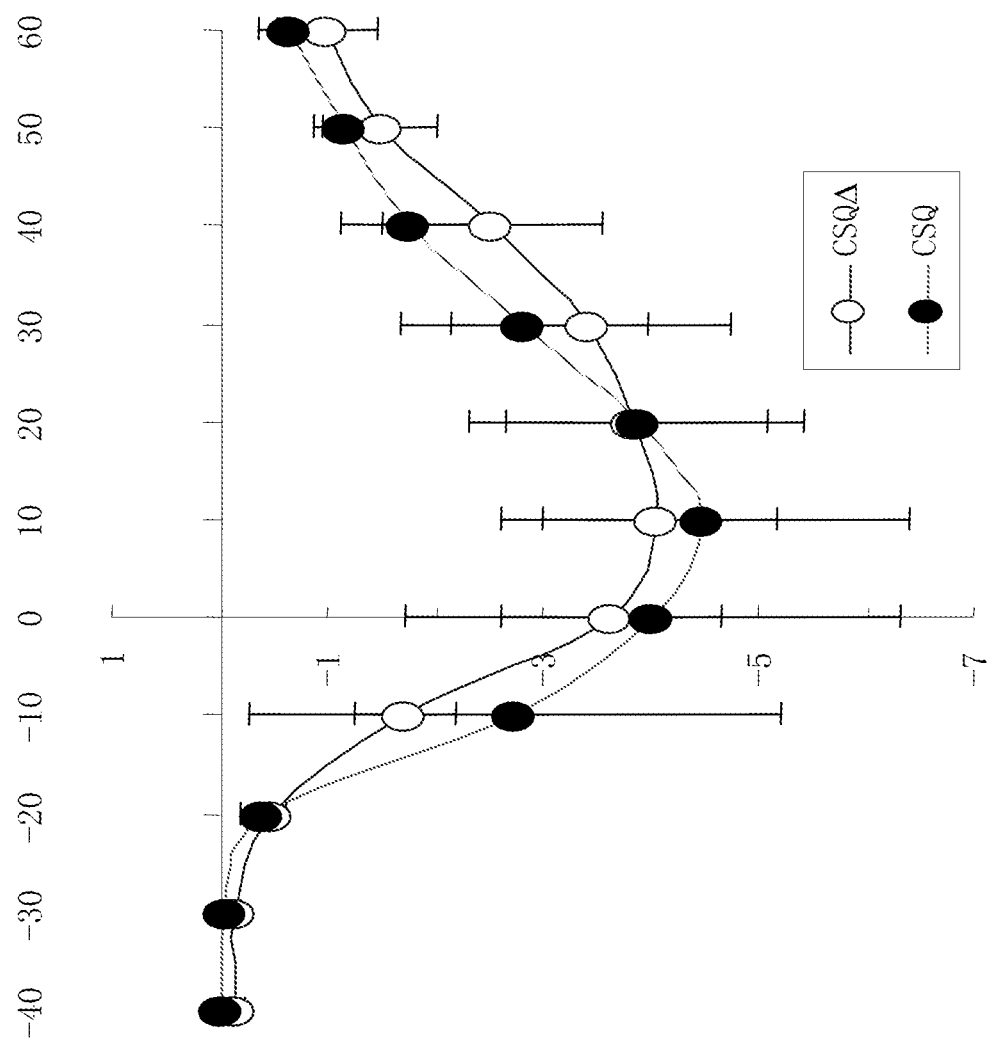
FIG. 12 shows L-type $Ca^{2+}$ currents of hESC-CMs after transduction by Ad-CSQ and Ad-CSQΔ as labelled. The X-axis indicates the membrane potential of the cells tested. Filled circles represent hESC-CMs transduced with Ad-CSQ, whereas open circles represent hESC-CMs transduced with Ad-CSQΔ. CSQ expression does not negatively affect L-type $Ca^{2+}$ currents, a crucial component of excitation-contraction coupling.

$I_{ca,L}$, the $Ca^{2+}$ trigger for SR $Ca^{2+}$ release, was recorded in Ad-CSQ and Ad-CSQΔ groups (FIG. 12). The magnitude of peak $I_{ca,L}$ was nearly identical in both groups at different membrane potentials, indicating no effect of CSQ expression on $I_{Ca,L}$. Moreover, no significant change occurred in membrane capacitance of H1-CMs with or without CSQ expression (data not shown).

No Induced T-tubules Formation

The membrane-selective dye, Di-8-ANEPPS, was used to detect the presence of t-tubules, invaginations of the surface membrane of H1-CMs. Regardless of CSQ expression, only the periphery (not the cellular mid-plane) of H1-CMs was positively stained (data not shown). Previously an organized pattern of staining was found in the center of adult CMs (59, 60). Thus the absence of organized t-tubules observed in hESC-CMs with CSQ expression, indicates that t-tubules formation was not induced by CSQ.

Discussion

Functional compatibility with the recipient adult myocytes is the basic requirement for hESC-CMs to apply for cell transplantation. Unfortunately, the functional properties related to $Ca^{2+}$ handling of hESC-CMs are demonstrated to be developing and immature compared to their adult counterparts due to the absence of either auxiliary proteins (e.g. CSQ, junctin or phospholambin) (14, 48) or organized spatial localization (t-tubules) (58). Therefore facilitated maturation of hESC-CMs towards the adult phenotype in vitro is indispensable for their future functional and structural integration with the host myocardium in vivo. For the first time, the feasibility of such genetic manipulation, i.e. expression of the absent CSQ, on the developmental profile of $Ca^{2+}$ homeostasis in hESC-CMs was assayed. These experiments show: 1) CSQ expression increased the functional SR $Ca^{2+}$ store; 2) $Ca^{2+}$ transients with larger magnitude and higher upstoke and decay kinetics were generated upon CSQ expression, which leads to more forceful contraction; 3) CSQ expression did not increase the $Ca^{2+}$ influx through the L-type $Ca^{2+}$ channel; and 4) the adenoviral CSQ gene transfer did not affect the expression of other related $Ca^{2+}$ handling proteins. These results demonstrate that expression of CSQ, a key regulatory factor on CICR, will facilitate the $Ca^{2+}$ handling of hESC-CMs towards a mature cardiomyocyte phenotype by providing precise regulations on $Ca^{2+}$ cycling.

CSQ is known as the high-capacity and low-affinity $Ca^{2+}$ buffer located in the internal SR, which confers SR in adult CMs tremendous storage capacity to maintain the repetitive contraction with minimal run-down in tension (49). The functional RyR mediated SR $Ca^{2+}$ stores are proved present in hESC-CMs (48) and its content increased over the developmental stages from 2 to 40 days post-beating (48, 58). By expressing CSQ, the SR $Ca^{2+}$ load was significantly enhanced in hESC-CMs of (14-21) +7 days old, providing a larger $Ca^{2+}$ store available for release. This is consistent with other findings on CSQ overexpression in adult CMs either with adenoviral transduction (57, 61) or from transgenic mice (62). On the other hand, SR luminal $Ca^{2+}$ is suggested to function as a regulator on RyR channel gating which occurs through either a direct $Ca^{2+}$ binding to the RyR inside the SR or via CSQ, triadin and junction (63, 64). Higher the SR $Ca^{2+}$ load, enhanced the open probability of the RyR. Therefore by adding the auxiliary protein CSQ, hESC-CMs gain not only an increased SR $Ca^{2+}$ store, but also more functionally more sensitive RyR upon the $Ca^{2+}$ influx via the L-type $Ca^{2+}$ channel.

The larger $Ca^{2+}$ transients obtained after CSQ expression in hESC-CMs were the most interesting observation. Since increased amplitude leads to stronger contraction, CSQ expression potentially enhanced the contractility of transduced hESC-CMs, which is the critical challenge to functionally mature the cells for transplantation. This favorable effect is attributed to the role of CSQ as both a buffer and luminal sensor of $Ca^{2+}$. It is established that the rate and sensitivity of $Ca^{2+}$ release depends on $Ca^{2+}$ loading, i.e., increased SR $Ca^{2+}$ load, enhanced $Ca^{2+}$ release (32, 65). Furthermore, a previous study showed that CSQ not only relayed the luminal $Ca^{2+}$ changes to RyR but also amplified the direct response of RyR to such alterations (66). The above results show that the $I_{Ca,L}$ was similar regardless of CSQ expression. Therefore, larger $Ca^{2+}$ transients were not resulted from more $Ca^{2+}$ influx trigging CICR in CSQ expressed hESC-CMs. Whether "E-C coupling" gain was increased or not needs further voltage-clamped $Ca^{2+}$ transient recording. All together, the CICR mechanism became more sensitive and effective in CSQ-expressed hESC-CMs, leading to more robust and rapid $Ca^{2+}$ transients. Consistent with a previous study, in rat adult CMs, the magnitude of $I_{Ca,L}$-induced $Ca^{2+}$ transients was increased when CSQ levels were elevated, which resulted from prolonged $Ca^{2+}$ release duration by slowing luminal $Ca^{2+}$-dependent closure of RyRs (57). Conversely, in adult CMs from transgenic mice, CSQ overexpression resulted in cardiac hypertrophy characterized as a significant decrease in cardiac contractility and amplitude of the $Ca^{2+}$ transients (62, 67). Without being bound by theory, Applicants postulate that one possible explanation is that the inhibitory effect of CSQ on the RyR opening may cause reduced SR $Ca^{2+}$ release even though a higher SR $Ca^{2+}$ store was available.

The role of CSQ, as a regulator of RyR, has been increasingly studied. Previous studies have shown that when SR luminal $Ca^{2+}$ is low, CSQ associates with RyR and inhibits its opening, while at high SR $Ca^{2+}$ content, CSQ detaches from RyR thereby increasing $Ca^{2+}$ release (49, 54). The total CSQ content can therefore potentially alter $Ca^{2+}$ release by affecting either its direct interaction with the RyR or the size of the functional $Ca^{2+}$ store inside SR. The interplay between these two actions after CSQ overexpression is unknown, whose balance may vary depending on the levels and durations (acute v.s. chronic) of CSQ increase. This may provide an explanation for the discrepancy of $Ca^{2+}$ transient changes found in different studies. It is important to point out that previous modulations on CSQ expression are increases (or decreases) above (or below) the physiological (optimal) level of CSQ in adult CMs. However, above experiments facilitated hESC-CMs to express CSQ from "none to all". Moreover, the inhibitory interaction of CSQ-RyR requires the presence of triadin and junction (55). Interestingly, CSQ activates purified RyR lacking triadin and junctin in lipid bilayer preparation (68, 69). This observation is consistent with the above results that CSQ increased the $Ca^{2+}$ transients in hESC-CMs which have not developed triadin and junction (48). Although the exact influence of CSQ-RyR interaction on SR $Ca^{2+}$ release is still in debate in adult CMs, these results shed light on a direct effect of restoring CSQ ex vivo without interferences from other auxiliary proteins. Given the significant role of CSQ on $Ca^{2+}$ homeostasis as a result of regulation on RyR release channel, these results show that expression of CSQ facilitated the $Ca^{2+}$ handling in hESC-CMs.

No significant alterations were found for other proteins involved in the $Ca^{2+}$-release cascade (RyR, junctin and triadin) upon CSQ expression in hESC-CMs. Previous studies demonstrated the abundant presence of RyR in hESC-CMs did not result in a regularly spaced pattern as reported in adult ventricular CMs (48, 58). Acute supplement of CSQ did not affect the level of RyR, which neither induced the appearance of junctin and triadin and were reported to be downregulated in transgenic mouse CMs overexpressing CSQ (62). Moreover, no compensatory alterations occurred in L-type $Ca^{2+}$ channel, SERCA and calreticulin, the fetal type of $Ca^{2+}$ buffer protein that was replaced after birth by CSQ (27). Pharmacological studies on blocking either RyR or SERCA further confirmed the functional SR $Ca^{2+}$ release and uptake channel/pump present in hESC-CMs. Consistent to the unchanged RyR/SERCA expressions, CSQ did not alter the response of hESC-CMs to the blockade on them.

It is well known that transgenic cardiac overexpression of CSQ leads to hypertrophy with increases in heart mass and cell size (62, 70), which has been used as a standard model of hypertrophy (71, 72). However, these results did not reveal any increase in cell size of CSQ-expressed hESC-CMs as reflected by membrane capacitance. Similarly, this acute CSQ supplement also failed to induce such structural development as t-tubule formation, which was absent in control hESC-CMs but critical in adult CMs to ensure spatially and temporally synchronous $Ca^{2+}$ release throughout the cell during CICR (73). The absence of t-tubules in single hESC-CMs (40-50 days) has been observed previously (unpublished data), whereas some t-tubules were found in clusters of hESC-CMs, to which the abundance, distribution and maturation pattern of the cells were far below the level in adult CMs (58).

In conclusion, expression of CSQ that is absent in hESC-CMs facilitates the $Ca^{2+}$ handling maturation by increasing the SR $Ca^{2+}$ load and conferring regulation on RyR $Ca^{2+}$ release. These results provide a strategy for designing effective cells which can be used for transplantation.

EXAMPLE 5 qPCR of Static Control and Electrically Conditioned hES2-CM Beating Clusters hES2-CM beating clusters manually dissected from hES2-EBs were plated in 0.1% gelatin-coated 6-well plates. After 2 days of recovery period, hES2 beating clusters were electrically stimulated at 2 V/cm with 5-msec pulse of 1 Hz by C-Pace Culture Pacer (Ionoptix) for 2 weeks. Medium was refreshed daily for the electrically stimulated (E-stim) and the static control (Static) groups. At the end of stimulation, the beating areas were again manually dissected and then solubilized in Trizol for mRNA extraction. qPCR was used to analyze the mRNA expression of atrial natriuretic factor (ANF), hyperpolarization-activated cyclic nucleotide-modulated channel (HCN4), inward-rectifying K⁺ channel (Kir2.1), transiently outward K⁺ channel (Kv1.4), myosin heavy chain α (MHCα) and β (MHCβ), myosin light chain-2a (MLC2a) and 2v (MLC2v). The mRNA expression was quantified using the $\Delta\Delta C_T$ method with GAPDH as the reference gene and normalized with the Static against the E-stim group. Normalization with E-stim as the calibrator group was chosen to allow for calculation of Kir2.1 expression that had no mRNA in the Static group.

Electrical-Conditioning Induces Mature, Ventricular-Like hES2-CMs

Figure 13:
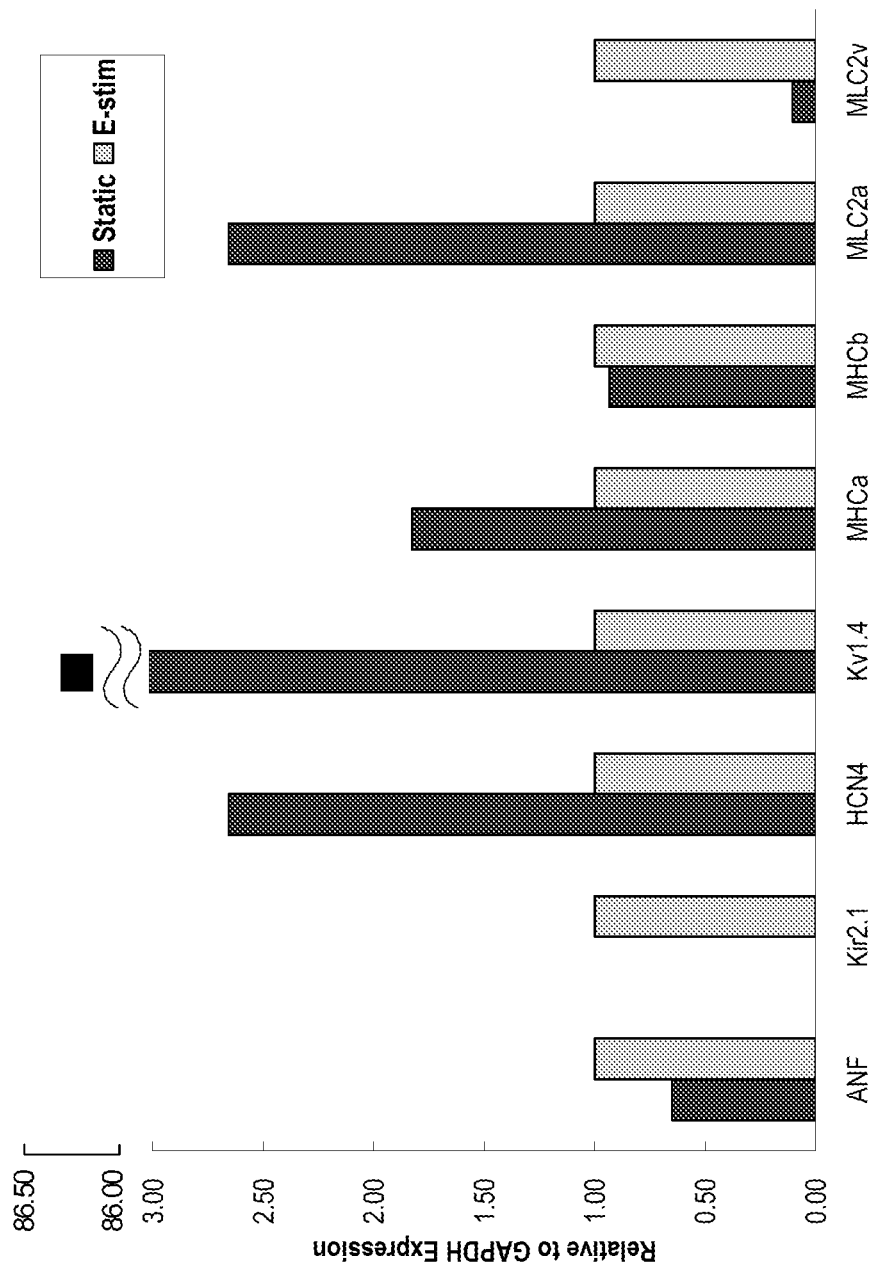
FIG. 13 shows electrical-conditioning of hESC-CMs induces a mature ventricular-like phenotype. Black bars indicate relative expression levels from static control cells, whereas gray bars indicate relative expression levels from electrical conditioned cells (E-stim). The X-axis indicates the corresponding gene assayed. The Y-axis indicated the relative mRNA levels versus mRNA levels for the GAPDH control gene. Normalization was done with the E-stim groups at to allow for calculation of Kir2.1 expression which was absent in static cells.

After 2 weeks of electrical-conditioning, the E-stim group showed significant mRNA expression increase relative to the static control group in ANF from 0.65 to 1.0, Kir2.1 from 0.0 to 1.0, and MLC2v from 0.11 to 1.0, while a significant mRNA expression decrease was shown in HCN4 from 2.66 to 1.0, Kv1.4 from 86.22 to 1.0, MHCα from 1.83 to 1.0, and MLC2a from 2.66 to 1.0 (FIG. 13). There was no significant change in MHCb between the two groups (FIG. 13). The increase in ANF, a hypertrophic marker, signifies that the electrically conditioned hES2-CMs are increasing in size to become more like their adult counterpart. The ion channel profile exhibited a dramatic increase in Kir2.1, a membrane potential stabilizer, and a decrease in HCN4, a membrane potential oscillator, which suggests a shift in hES2-CMs to become more mature with a more stable electrophysiology. A decrease in Kv1.4 is suggestive of hES2-CMs exhibiting the epicardial ventricular phenotype. The mRNA analysis of the contractile apparatus with a decrease in MHCa or the isoform with a higher actomyosin ATPase, suggests CMs transitioning to a slower contraction rate, which is also a sign of maturity since fetal hearts are known to have higher beating frequency than adult hearts. Finally, a decrease in MLC2a and increase in MLC2v both indicate that the electrically stimulated hES2-CMs were directed towards a ventricular phenotype. Overall, electrical conditioning of hES2-CMs results in a more mature and ventricular-like phenotype.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

REFERENCES

1. Li, R A, Moore J C, Tarasova Y S, et al. (2006) Human embryonic stem cell-derived cardiomyocytes: therapeutic potentials and limitations. *J Stem Cell;* 1:109-124.
2. Siu C W, Moore J C and Li R A. (2007). Human embryonic stem cell-derived cardiomyocytes for heart therapies. *Cardiovascular & Haematological Disorders-Drug Targets;* 7(2):145-152.
3. Thomson J A, Itskovitz-Eldor J, Shapiro S S, et al. (1998). Embryonic stem cell lines derived from human blastocysts. *Science;* 282(5391):1145-1147.
4. Xue T, Cho H C, Akar F G, et al. (2005). Functional integration of electrically active cardiac derivatives from genetically engineered human embryonic stem cells with quiescent recipient ventricular cardiomyocytes: insights into the development of cell-based pacemakers. *Circulation;* 111:11-20.
5. He J Q, Ma Y, Lee Y, et al. (2003). Human embryonic stem cells develop into multiple types of cardiac myocytes: action potential characterization. *Circulation Research;* 93:32-39.
6. Mummery C, Ward-van Oostwaard D, Doevendans P, et al. (2003). Differentiation of human embryonic stem cells to cardiomyocytes: role of coculture with visceral endoderm-like cells. *Circulation;* 107:2733-2740.
7. Kehat I, Kenyagin-Karsenti D, Snir M, et al. (2001). Human embryonic stem cells can differentiate into myocytes with structural and functional properties of cardiomyocytes. *The Journal of Clinical Investigation;* 108:407-414.
8. Xu C, Police S, Rao N, et al. (2002). Characterization and enrichment of cardiomyocytes derived from human embryonic stem cells. *Circulation Research;* 91:501-508.
9. Kehat I, Khimovich L, Caspi O, et al. (2004). Electromechanical integration of cardiomyocytes derived from human embryonic stem cells. *Nature Biotechnology;* 22:1282-1289.
10. Bers D M. (2002). Cardiac excitation-contraction coupling. *Nature;* 415:198-205.
11. Guatimosim S, Dilly K, Santana L F, et al. (2002). Local Ca(2+) signaling and EC coupling in heart: Ca(2+) sparks and the regulation of the [Ca(2+)](i) transient. *Journal of Molecular and Cellular Cardiology;* 34:941-950.
12. Tomaselli G F, Zipes D P. (2004). What causes sudden death in heart failure? *Circulation Research;* 95:754-763.
13. Fu J D, Yu H M, Wang R, et al. (2006). Developmental regulation of intracellular calcium transients during cardiomyocyte differentiation of mouse embryonic stem cells. *Acta Pharmacologica Sinica;* 27:901-910.
14. Dolnikov K, Shilkrut M, Zeevi-Levin N, et al. (2006). Functional properties of human embryonic stem cell-derived cardiomyocytes: intracellular Ca2+ handling and the role of sarcoplasmic reticulum in the contraction. *Stem Cells;* 24:236-245.
15. Gulbins H, Meiser B M, Reichenspurner H, et al. (2002). Cell transplantation—a potential therapy for cardiac repair in the future? *The Heart Surgery Forum;* 5:E28-34.
16. Moore J C, van Laake L W, Braam S R, et al. (2005). Human embryonic stem cells: genetic manipulation on the way to cardiac cell therapies. *Reproductive Toxicology;* 20:377-391.
17. Wang K, Xue T, Tsang S Y, et al. (2005). Electrophysiological properties of pluripotent human and mouse embryonic stem cells. *Stem Cells;* 23:1526-1534.
18. Sartiani L, Bettiol E, Stillitano F, et al. (2007). Developmental changes in cardiomyocytes differentiated from human embryonic stem cells: a molecular and electrophysiological approach. *Stem Cells;* 25:1136-1144.
19. Mitra R, Morad M, (1986). Two types of calcium channels in guinea pig ventricular myocytes. *Proceedings of The National Academy of Sciences of The United States of America;* 83:5340-5344.
20. Sutko J L, Ito K, Kenyon J L., (1985). Ryanodine: a modifier of sarcoplasmic reticulum calcium release in striated muscle. *Federation Proceedings;* 44:2984-2988.
21. Zhang Q, Yan L, Weiss H R, et al. (2002). Cyclic GMP-induced reduction in cardiac myocyte function is partially mediated by activation of the sarcoplasmic reticulum Ca(2+)-ATPase. *Pharmacology;* 64:106-112.
22. Lompre A M, Lambert F, Lakatta E G, et al. (1991). Expression of sarcoplasmic reticulum Ca(2+)-ATPase and calsequestrin genes in rat heart during ontogenic development and aging. *Circulation Research;* 69:1380-1388.
23. Komuro I, Kurabayashi M, Shibazaki Y, et al. (1989). Molecular cloning and characterization of a Ca2++Mg2+-dependent adenosine triphosphatase from rat cardiac sarcoplasmic reticulum. Regulation of its expression by pressure overload and developmental stage. *The Journal of Clinical Investigation;* 83:1102-1108.
24. Qu Y, Ghatpande A, el-Sherif N, et al. (2000). Gene expression of Na+/Ca2+ exchanger during development in human heart. *Cardiovascular Research;* 45:866-873.
25. Hatem S N, Benardeau A, Rucker-Martin C, et al. (1997). Different compartments of sarcoplasmic reticulum participate in the excitation-contraction coupling process in human atrial myocytes. *Circulation Research;* 80:345-353.
26. Mesaeli N, Nakamura K, Zvaritch E, et al. (1999). Calreticulin is essential for cardiac development. *The Journal of Cell Biology;* 144:857-868.
27. Lynch J M, Chilibeck K, Qui Y, et al. (2006). Assembling pieces of the cardiac puzzle; calreticulin and calcium-dependent pathways in cardiac development, health, and disease. *Trends in Cardiovascular Medicine;* 16:65-69.
28. Song L, Alcalai R, Arad M, et al. (2006). Calsequestrin 2 (CASQ2) mutations increase expression of calreticulin and ryanodine receptors, causing catecholaminergic polymorphic ventricular tachycardia. *The Journal of Clinical Investigation;* 117:1814-1823.
29. Satin J, Kehat I, Caspi O, et al. (2004). Mechanism of spontaneous excitability in human embryonic stem cell derived cardiomyocytes. *The Journal of Physiology;* 559:479-496.
30. Dolnikov K, Shilkrut M, Zeevi-Levin N, et al. (2005). Functional properties of human embryonic stem cell-derived cardiomyocytes. *Annals of the New York Academy of Sciences;* 1047:66-75.
31. Itzhaki I, Schiller J, Beyar R, et al. (2006). Calcium handling in embryonic stem cell-derived cardiac myocytes: of mice and men. *Annals of the New York Academy of Sciences;* 1080:207-215.
32. Bassani J W, Yuan W, Bers D M. (1995). Fractional SR Ca release is regulated by trigger Ca and SR Ca content in cardiac myocytes. *The American Journal of Physiology;* 268:C1313-1319.
33. Janczewski A M, Spurgeon H A, Stern M D, et al. (1995). Effects of sarcoplasmic reticulum Ca2+ load on the gain function of Ca2+ release by Ca2+ current in cardiac cells. *The American Journal of Physiology;* 268:H916-920.
34. Sauer H, Theben T, Hescheler J, et al, (2001). Characteristics of calcium sparks in cardiomyocytes derived from embryonic stem cells. *American Journal of Physiolog;* 281:H411-421.
35. Huber I, Itzhaki I, Caspi O, et al. (2007). Identification and selection of cardiomyocytes during human embryonic stem cell differentiation. *FASEB J;* 21(10):2551-2563.
36. Kolossov E, Fleischmann B K, Liu Q, et al. (1998). Functional characteristics of ES cell-derived cardiac precursor cells identified by tissue-specific expression of the green fluorescent protein. *The Journal of Cell Biology;* 143:2045-2056.
37. Gorza L, Schiaffino S, Volpe P. (1993). Inositol 1,4,5-trisphosphate receptor in heart: evidence for its concentration in Purkinje myocytes of the conduction system. *The Journal of Cell Biology;* 121:345-353.
38. Kapur N, Banach K. (2007). Inositol-1,4,5-trisphosphate-mediated spontaneous activity in mouse embryonic stem cell-derived cardiomyocytes. *The Journal of Physiology;* 581(Pt3):1113-1127.
39. Xue, T., Cho, H. C., Akar, F. G., Tsang, S. Y., Jones, S. P., Marban, E., Tomaselli, G. F., and Li, R. A. (2005). Functional integration of electrically active cardiac derivatives from genetically engineered human embryonic stem cells with quiescent recipient ventricular cardiomyocytes: insights into the development of cell-based pacemakers. *Circulation;* 111:11-20.
40. Wiznerowicz, M., and Trono, D. (2003). Conditional suppression of cellular genes: lentivirus vector-mediated drug-inducible RNA interference. *J Virol;* 77:8957-8961.
41. Zhou, B. Y., Ye, Z., Chen, G., Gao, Z. P., Zhang, Y. A., and Cheng, L. (2007). Inducible and reversible transgene expression in human stem cells after efficient and stable gene transfer. *Stem Cells;* 25:779-789.
42. Deuschle, U., Meyer, W. K., and Thiesen, H. J. (1995). Tetracycline-reversible silencing of eukaryotic promoters. *Mol Cell Biol;* 15:1907-1914.
43. Margolin, J. F., Friedman, J. R., Meyer, W. K., (1994). Vissing, H., Thiesen, H. J., and Rauscher, F. J., 3rd. Kruppel-associated boxes are potent transcriptional repression domains. *Proc Natl Acad Sci USA;* 91:4509-4513.
44. Moosmann, P., Georgiev, O., Thiesen, H. J., Hagmann, M., and Schaffner, W. (1997). Silencing of RNA polymerases II and III-dependent transcription by the KRAB protein domain of KOX1, a Kruppel-type zinc finger factor. *Biol Chem;* 378:669-677.
45. Senatore, B., Cafieri, A., Di Marino, I., Rosati, M., Di Nocera, P. P., and Grimaldi, G. (1999). A variety of RNA polymerases II and III-dependent promoter classes is repressed by factors containing the Kruppel-associated/finger preceding box of zinc finger proteins. *Gene;* 234:381-394.
46. Zufferey, R., Nagy, D., Mandel, R. J., Naldini, L., and Trono, D. (1997). Multiply attenuated lentiviral vector achieves efficient gene delivery in vivo. *Nat Biotechnol;* 15:871-875.
47. Moore, J. C., van Laake, L. W., Braam, S. R., Xue, T., Tsang, S. Y., Ward, D., Passier, R., Tertoolen, L. L., Li, R. A., and Mummery, C. L. (2005). Human embryonic stem cells: genetic manipulation on the way to cardiac cell therapies. *Reprod Toxicol;* 20:377-391.
48. Liu J, Fu J D, Siu C W, et al. (2007). Functional sarcoplasmic reticulum for calcium handling of human embryonic stem cell-derived cardiomyocytes: insights for driven maturation. *Stem Cells;* 25:3038-3044.
49. Beard N A, Laver D R, Dulhunty A F. (2004). Calsequestrin and the calcium release channel of skeletal and cardiac muscle. *Progress in Biophysics and Molecular Biology;* 85:33-69.
50. Campbell K P, MacLennan D H, Jorgensen A O, et al. (1983). Purification and characterization of calsequestrin from canine cardiac sarcoplasmic reticulum and identification of the 53,000 dalton glycoprotein. *The Journal of Biological Chemistry;* 258:1197-1204.
51. Szegedi C, Sarkozi S, Herzog A, et al. (1999). Calsequestrin: more than 'only' a luminal Ca2+ buffer inside the sarcoplasmic reticulum. *The Biochemical Journal;* 337 (Pt 1):19-22.
52. Boyden P A, ter Keurs H E (2001). Reverse excitation-contraction coupling: Ca2+ ions as initiators of arrhythmias. *Journal of Cardiovascular Electrophysiology;* 12:382-385.
53. Fabiato A. (1985). Time and calcium dependence of activation and inactivation of calcium-induced release of calcium from the sarcoplasmic reticulum of a skinned canine cardiac Purkinje cell. *The Journal of General Physiology;* 85:247-289.
54. Lee Y S, Keener J P. (2008). A calcium-induced calcium release mechanism mediated by calsequestrin. *Journal of Theoretical Biology;* 253 (4): 668-679.

55. Gyorke I, Hester N, Jones L R, et al. (2004). The role of calsequestrin, triadin, and junctin in conferring cardiac ryanodine receptor responsiveness to luminal calcium. *Biophysical Journal;* 86:2121-2128.
56. Hardy S, Kitamura M, Harris-Stansil T, et al. (1997). Construction of adenovirus vectors through Cre-lox recombination. *Journal of Virology;* 71:1842-1849.
57. Terentyev D, Viatchenko-Karpinski S, Gyorke I, et al. (2003). Calsequestrin determines the functional size and stability of cardiac intracellular calcium stores: Mechanism for hereditary arrhythmia. *Proceedings of the National Academy of Sciences of the United States of America;* 100:11759-11764.
58. Satin J, Itzhaki I, Rapoport S, et al. (2008). Calcium Handling in Human Embryonic Stem Cell Derived Cardiomyocytes. *Stem Cells;* 26(8)1961-1972.
59. Louch W E, Bito V, Heinzel F R, et al. (2004). Reduced synchrony of Ca2+ release with loss of t-tubules-a comparison to Ca2+ release in human failing cardiomyocytes. *Cardiovascular Research;* 62:63-73.
60. Lipp P, Huser J, Pott L, et al. (1996). Spatially non-uniform Ca2+ signals induced by the reduction of transverse tubules in citrate-loaded guinea-pig ventricular myocytes in culture. *The Journal of Physiology;* 497 (Pt 3):589-597.
61. Miller S L, Currie S, Loughrey C M, et al.(2005). Effects of calsequestrin over-expression on excitation-contraction coupling in isolated rabbit cardiomyocytes. *Cardiovascular Research;* 67:667-677.
62. Jones L R, Suzuki Y J, Wang W, et al. (1998). Regulation of Ca2+ signaling in transgenic mouse cardiac myocytes overexpressing calsequestrin. *The Journal of Clinical Investigation;* 101:1385-1393.
63. Ching L L, Williams A J, Sitsapesan R. (2000). Evidence for Ca(2+) activation and inactivation sites on the luminal side of the cardiac ryanodine receptor complex. *Circulation Research;* 87:201-206.
64. Gyorke I, Gyorke S. (1998). Regulation of the cardiac ryanodine receptor channel by luminal Ca2+ involves luminal Ca2+ sensing sites. *Biophysical Journal;* 75:2801-2810.
65. Lamb G D, Cellini M A, Stephenson D G. (2001). Different Ca2+ releasing action of caffeine and depolarisation in skeletal muscle fibres of the rat. *The Journal of Physiology;* 2001;531:715-728.
66. Beard N A, Casarotto M G, Wei L, et al. (2005). Regulation of ryanodine receptors by calsequestrin: effect of high luminal Ca2+ and phosphorylation. *Biophysical Journal;* 88:3444-3454.
67. Schmidt A G, Kadambi V J, Ball N, et al. (2000). Cardiac-specific overexpression of calsequestrin results in left ventricular hypertrophy, depressed force-frequency relation and pulsus alternans in vivo. *Journal of Molecular and Cellular Cardiology;* 32:1735-1744.
68. Beard N A, Sakowska M M, Dulhunty A F, et al. (2002). Calsequestrin is an inhibitor of skeletal muscle ryanodine receptor calcium release channels. *Biophysical Journal;* 82:310-320.
69. Herzog A, Szegedi C, Jona I, et al. (2000). Surface plasmon resonance studies prove the interaction of skeletal muscle sarcoplasmic reticular Ca(2+) release channel/ryanodine receptor with calsequestrin. *FEBS letters;* 472:73-77.
70. Sato Y, Ferguson D G, Sako H, et al. (1998). Cardiac-specific overexpression of mouse cardiac calsequestrin is associated with depressed cardiovascular function and hypertrophy in transgenic mice. *The Journal of Biological Chemistry;* 273:28470-28477.
71. Yang A, Sonin D, Jones L, et al. (2004). A beneficial role of cardiac P2x4 receptors in heart failure: rescue of the calsequestrin overexpression model of cardiomyopathy. *American Journal of Physiology;* 287:H1096-1103.
72. Cho M C, Rapacciuolo A, Koch W J, et al. (1999). Defective beta-adrenergic receptor signaling precedes the development of dilated cardiomyopathy in transgenic mice with calsequestrin overexpression. *The Journal of Biological Chemistry;* 274:22251-22256.
73. Brette F, Orchard C. (2003). T-tubule function in mammalian cardiac myocytes. *Circulation Research;* 92:1182-1192.

What is claimed is:

1. An in vitro method for increasing the function of sarcoplasmic reticulum (SR) in or improving $Ca^{2+}$ handling, of a stem cell-differentiated human cardiomyocyte comprising functionally mature sarcoplasmic reticulum (SR), the method comprising enhancing the expression of a calcium handling protein selected from calsequestrin, junctin, triadin or phospholamban in the stem cell-differentiated human cardiomyocyte, wherein the cardiomyocyte is differentiated from a stem cell in vitro and is caffeine-responsive, wherein the enhancing the expression of the calcium handling protein comprises transfecting the cardiomyocyte with a nucleotide encoding the calcium handling protein.

2. The method of claim 1, wherein the cardiomyocyte comprises a functional RyR protein.

3. The method of claim 1, wherein the cardiomyocyte comprises a functional SERCA2a protein.

* * * * *